(12) United States Patent
Takayama

(10) Patent No.: US 12,733,811 B2
(45) Date of Patent: Sep. 15, 2026

(54) DETECTION DEVICE

(71) Applicant: SEIKO EPSON CORPORATION, Tokyo (JP)

(72) Inventor: Hiromu Takayama, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 250 days.

(21) Appl. No.: 18/597,924

(22) Filed: Mar. 7, 2024

(65) Prior Publication Data

US 2024/0298897 A1 Sep. 12, 2024

(30) Foreign Application Priority Data

Mar. 8, 2023 (JP) ................................ 2023-035434

(51) Int. Cl.
*A61B 5/00* (2006.01)

(52) U.S. Cl.
CPC ........ *A61B 5/0059* (2013.01); *A61B 2503/40* (2013.01)

(58) Field of Classification Search
CPC .......................... A61B 5/0059; A61B 2503/40
See application file for complete search history.

(56) References Cited

U.S. PATENT DOCUMENTS 5,350,922 A * 9/1994 Bartz ..................... G01N 21/49 250/575
2001/0056243 A1 12/2001 Ohsaki et al.
2018/0125381 A1* 5/2018 Nakata ................... A61B 5/721
2018/0279892 A1* 10/2018 Qi ........................ A61B 5/7214
2020/0229767 A1* 7/2020 Eletr .................. A61B 5/14552
2022/0133188 A1* 5/2022 Lin ........................ A61B 5/445 600/323
2023/0172499 A1* 6/2023 Marriott ............... A61B 5/7203 600/323

FOREIGN PATENT DOCUMENTS

JP 2001353133 12/2001

* cited by examiner

*Primary Examiner* — Michelle M Iacoletti
*Assistant Examiner* — Jarreas Underwood
(74) *Attorney, Agent, or Firm* — JCIPRNET

(57) ABSTRACT

A detection device including a substrate, a first light emitting unit that emits first light, a first light receiving unit that receives the first light, a first optical member that transmits the first light and covers the first light emitting unit at the substrate, a second optical member that transmits the first light and covers the first light receiving unit at the substrate, and an accommodating member that is provided at the substrate and formed with a first opening accommodating the first light emitting unit and the first optical member and a second opening accommodating the first light receiving unit and the second optical member, wherein at least one of the first optical member and the second optical member protrudes from an opening formed in the accommodating member.

19 Claims, 13 Drawing Sheets

DETECTION DEVICE

The present application is based on, and claims priority from JP Application Serial Number 2023-035434, filed Mar. 8, 2023, the disclosure of which is hereby incorporated by reference herein in its entirety.

BACKGROUND

1. Technical Field

The present disclosure relates to a detection device.

2. Related Art

Research and development have been performed on detection devices that detect biological information such as a pulse wave, a pulse, and oxygen saturation using a non-invasive method.

In this regard, there is known a detection device that includes a detection unit including a light emitting element and a light receiving element, and a detection device body including a circuit unit coupled to the detection unit via a signal line, is used by attaching the detection unit to a back side of a wrist or a back side of a forearm part of a person, and detects a pulse wave based on a change over time in an amount of received light of light reflected by hemoglobin contained in blood vessels of the person in the light emitted from the light emitting element (see JP-A-2001-353133).

Here, the detection device described in JP-A-2001-353133 further includes a light transmitting plate having a convexly curved surface. This is to improve adhesion between the detection unit and a surface of the skin of the person and to increase the amount of received light of the light reflected by hemoglobin contained in the blood vessels of the person in the light emitted from the light emitting element. However, due to a size of the light transmitting plate itself, an increase in the number of components accompanying the light transmitting plate, or the like, it is sometimes difficult to achieve reduction in size of the detection device. That is, it is sometimes difficult to achieve reduction in size of the detection device while inhibiting a decrease in the amount of received light.

SUMMARY

In order to solve the above problems, one aspect of the present disclosure is a detection device including a substrate, a first light emitting unit that emits first light and is provided at the substrate, a first light receiving unit that receives the first light, is parallel to the substrate when viewed in a first direction parallel to the substrate, and is provided at the substrate side by side with the first light emitting unit in a second direction orthogonal to the first direction, a first optical member that transmits the first light and covers the first light emitting unit at the substrate, a second optical member that transmits the first light and covers the first light receiving unit at the substrate, and an accommodating member that is provided at the substrate and formed with a first opening accommodating the first light emitting unit and the first optical member and a second opening accommodating the first light receiving unit and the second optical member, wherein at least one of the first optical member and the second optical member protrudes from an opening formed in the accommodating member in a third direction intersecting the first direction and the second direction.

DESCRIPTION OF EMBODIMENTS

Overview of Present Disclosure

Figure 1:
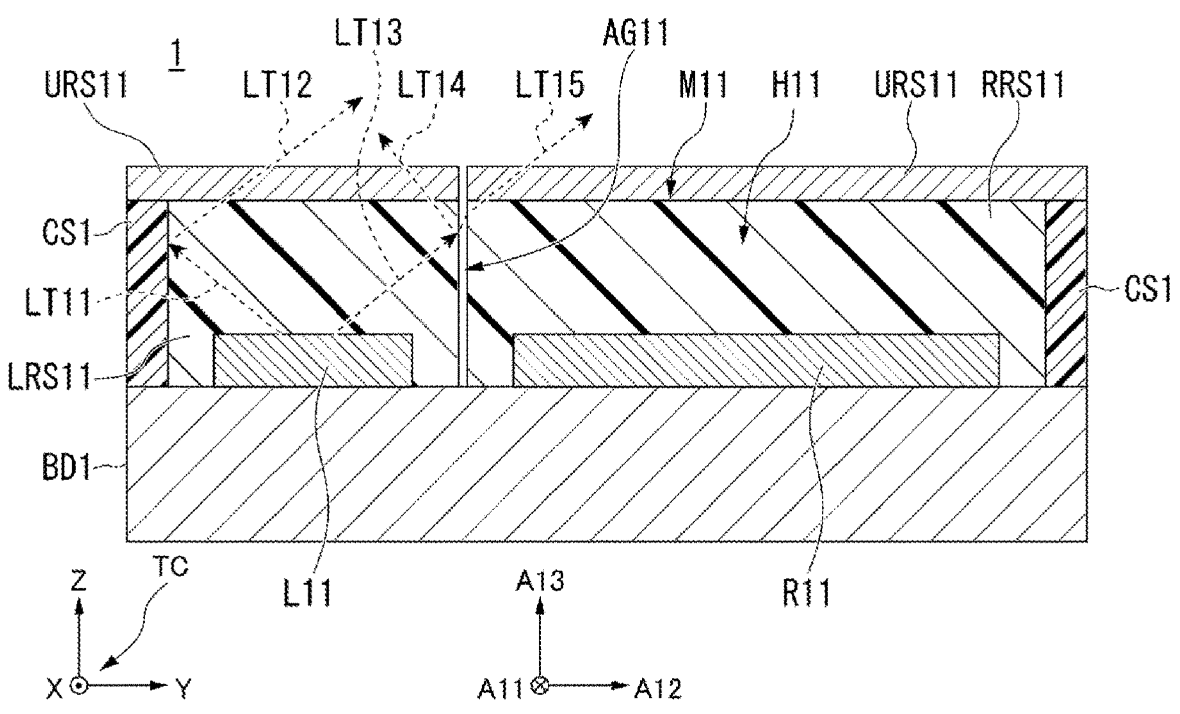
FIG. 1 is a cross-sectional view showing a first configuration example of a detection device 1.

An overview of the present disclosure will be described below. In the present disclosure, a configuration of a detection device that emits light toward the inside of a living body and detects biological information based on a change over time in an amount of light reflected from within the living body will be described. More specifically, in the present disclosure, a configuration of a detection device that can achieve reduction in size while inhibiting a decrease in an amount of received light of light reflected from within a living body will be described. Such a configuration can be realized by, for example, each of the following three first to third embodiments described below, or a combination of some or all of these three embodiments. Thus, in the following description, each of these three embodiments will be described in detail. Also, each of these three embodiments or a combination of some or all of these three embodiments may be combined with other configurations as long as functions of detection devices described below are not impaired.

First Embodiment

The first embodiment will be described below with reference to the drawings.

Overview of Detection Device of First Embodiment.

First, an overview of a detection device according to the first embodiment will be described.

The detection device according to the first embodiment includes a substrate, a first light emitting unit, a first light receiving unit, a first optical member, a second optical member, and an accommodating member. The first light emitting unit emits first light and is provided at the substrate. The first light receiving unit receives the first light and is provided at the substrate side by side with the first light emitting unit in a second direction when viewed in a first direction parallel to the substrate. Here, the second direction is parallel to the substrate and orthogonal to the first direction. The first optical member transmits the first light and covers the first light emitting unit at the substrate. The second optical member transmits the first light and covers the first light receiving unit at the substrate. The accommodating member is provided at the substrate and has an opening formed in which the first light emitting unit, the first optical member, the first light receiving unit, and the second optical member are accommodated. In addition, at least a part between the first optical member and the second optical member in the second direction is a gap. Thus, the detection device can increase an amount of light received by the first light receiving unit by bringing the first light emitting unit and the first light receiving unit closer to each other, and can reduce a size thereof in the second direction, as compared with a case in which a resin, a metal, or the like is disposed instead of the gap. That is, the detection device can achieve reduction in size while inhibiting reduction in the amount of light received by the light receiving unit.

A configuration of the detection device according to the first embodiment will be described in detail.

Configuration of Detection Device of First Embodiment

A configuration of the detection device according to the first embodiment will be described below using a detection device 1 as an example. In the first embodiment, for convenience of description, a user of the detection device 1 will be described as a first user. In addition, in the first embodiment, for convenience of description, when the detection device 1 is viewed while facing in a certain direction, it will be described as the detection device 1 being viewed in that direction.

FIG. 1 is a cross-sectional view showing a first configuration example of the detection device 1. Here, a three-dimensional coordinate system TC is a three-dimensional Cartesian coordinate system indicating directions in the drawings in which the three-dimensional coordinate system TC is drawn. In the present disclosure, for convenience of description, an X axis in the three-dimensional coordinate system TC will be simply described as an X axis. Also, in the present disclosure, for convenience of description, a Y axis in the three-dimensional coordinate system TC will be simply described as a Y axis. In addition, in the following description, for convenience of description, a Z axis in the three-dimensional coordinate system TC will be simply described as a Z axis. Further, in the present disclosure, for convenience of description, a positive direction of the Z axis will be described as up or upward, and a negative direction of the Z axis will be described as down or downward.

The detection device 1 is a device that detects biological information using a non-invasive method. In the first embodiment, as an example, a case in which the detection device 1 is a device that detects biological information of a person will be described. In this case, the detection device 1 detects a pulse wave, a pulse, oxygen saturation, and the like as the biological information and is provided, for example, in vital equipment such as a smart watch, an active tracker, or a smart ring. Also, the detection device 1 may be configured to detect biological information of an animal other than a human, or may be configured to detect biological information of a plant.

Specifically, the detection device 1 is pressed against the skin of the person and emits light in a predetermined wavelength band toward the skin. In addition, the detection device 1 receives the reflected light of the light emitted toward the skin and detects a pulse, oxygen saturation, and the like based on a change over time in the amount of received light of the received reflected light. Here, a substance that reflects the light emitted by the detection device 1 is, for example, hemoglobin or the like in capillary vessels, but is not limited thereto. For example, the detection device 1 uses light in a green wavelength band in the case of detecting a pulse. The green wavelength band is 500 to 570 [nm]. For example, the detection device 1 uses light in a red wavelength band, light in an infrared wavelength band, or the like in the case of detecting oxygen saturation. The red wavelength band is 630 to 680 [nm], and the infrared light wavelength band is 850 to 1000 [nm]. In the present disclosure, for convenience of description, the light in the green wavelength band will be described as green light. Also, in the present disclosure, for convenience of description, the light in the red wavelength band will be described as red light. In addition, in the present disclosure, for convenience of description, the light in the infrared light wavelength band will be described as infrared light.

The detection device 1 includes, for example, a substrate BD1, a first light emitting unit L11, a first light receiving unit R11, a first light emitting side optical member LRS11, a first light receiving side optical member RRS11, an accommodating member CS1, and a coat member URS11. In addition, the detection device 1 also includes other members such as a processor that acquires data indicating an amount of light received by the first light receiving unit R11 and performs various types of processing based on the acquired data. The various types of processing include, for example, processing of calculating a pulse, oxygen saturation, and the like based on a change over time in the amount of received light indicated by the data. However, in the present disclosure, descriptions of these other members will be omitted. For this reason, these other members will also be omitted in each figure. Also, the detection device 1 may have a configuration in which the coat member URS11 is not provided.

The substrate BD1 may be any substrate that can be used for a substrate of the detection device 1. The substrate BD1 is a base using, for example, a phenol resin, a polyimide resin, a fluorine resin, or an epoxy resin. The substrate BD1 is provided with the first light emitting unit L11, the first light receiving unit R11, the first light emitting side optical member LRS11, the first light receiving side optical member RRS11, and the accommodating member CS1. In the first embodiment, for convenience of description, one of two surfaces of the substrate BD1 on the positive direction side of the Z axis in each figure will be described as an upper surface of the substrate BD1, and a surface thereof in the negative direction of the Z axis in each figure will be described as a lower surface of the substrate BD1. In addition, in the following description, as an example, a case in which each of the first light emitting unit L11, the first light receiving unit R11, the first light emitting side optical member LRS11, the first light receiving side optical member RRS11, and the accommodating member CS1 is provided at the upper surface of the substrate BD1 will be described.

The first light emitting unit L11 is a light emitting element, a light emitting device, or the like that emits light in a predetermined first wavelength band as the first light. The first light emitting unit L11 is, for example, a light emitting diode (LED), but may instead be another light emitting element such as an organic light emitting diode (OLED), a micro (u) LED, a vertical cavity surface emitting laser (VCSEL), or the like, or another light emitting device. In the first embodiment, a case in which the first wavelength band is the green wavelength band will be described as an example. In this case, the first light emitting unit L11 emits the green light as the first light.

The first light emitting unit L11 is provided at the upper surface of the substrate BD1. In addition, in the first embodiment, in each figure used to describe the first embodiment, in order to prevent the figures from becoming complicated, members for coupling a transmission path at the substrate BD1 to the first light emitting unit L11 are omitted. Here, the members are, for example, wire bonding, coupling terminals and the like, but are not limited thereto. The first light emitting unit L11 is an example of the first light emitting unit.

The first light receiving unit R11 is a light receiving element, a light receiving device, or the like that receives the first light emitted by the first light emitting unit L11. Also, the first light receiving unit R11 may have a configuration that can receive the first light and cannot receive light in a wavelength band different from the first wavelength band. The configuration that cannot receive light in a wavelength band different from the first wavelength band is realized by, for example, a band-pass filter or the like. In the first embodiment, as an example, a case in which the first light receiving unit R11 can receive the first light and can receive light in a wavelength band different from the first wavelength band will be described.

When viewed in a predetermined first direction A11 with respect to the substrate BD1, the first light receiving unit R11 is provided at the upper surface of the substrate BD1 side by side with the first light emitting unit L11 in a second direction A12. Here, the first direction A11 may be any direction as long as it is parallel to the substrate BD1. In addition, the second direction A12 is parallel to the substrate BD1 and is orthogonal to the first direction A11.

In each figure used to describe the first embodiment, as an example, a state in which the first direction A11 coincides with a negative direction of the X axis is shown. In addition, in each figure, as an example, a state in which the second direction A12 coincides with a positive direction of the Y axis is shown. For this reason, the cross-sectional view shown in FIG. 1 is a cross-sectional view of the detection device 1 along a virtual plane orthogonal to the first direction A11 so that the first light emitting unit L11 and the first light receiving unit R11 can be seen when viewed in the first direction A11. Also, in each figure, in order to prevent the figures from being complicated, members for coupling the transmission path at the substrate BD1 to the first light receiving unit R11 are omitted. Here, the members are, for example, wire bonding, coupling terminals and the like, but are not limited thereto. The first light receiving unit R11 is an example of the first light receiving unit.

The first light emitting side optical member LRS11 transmits the first light. In addition, the first light emitting side optical member LRS11 may be configured to transmit the first light and transmit light in a wavelength band different from the first wavelength band, or may be configured to transmit the first light and not to transmit light in a wavelength band different from the first wavelength band. In the first embodiment, as an example, a case in which the first light emitting side optical member LRS11 transmits the first light and transmits light in a wavelength band different from the first wavelength band will be described. The first light emitting side optical member LRS11 is made of a material that has a refractive index of about 1.4 or more and transmits the first light, for example, a resin that transmits light, such as a transparent epoxy resin or a transparent acrylic resin, but is not limited thereto. Also, a refractive index of the transparent epoxy resin is about 1.52. Further, a refractive index of the transparent acrylic resin is about 1.45.

The first light emitting side optical member LRS11 covers the first light emitting unit L11 at the substrate BD1. In other words, the first light emitting side optical member LRS11 and the substrate BD1 surround and enclose the first light emitting unit L11. In the first embodiment, as an example, a case in which the first light emitting side optical member LRS11 is provided at the upper surface of the substrate BD1 so that no gap is generated between itself and the first light emitting unit L11 will be described. In this case, there is no gap between the first light emitting side optical member LRS11 and the first light emitting unit L11 except for a gap unintentionally formed in a manufacturing process. Thus, the detection device 1 can inhibit refraction of the first light emitted from the first light emitting unit L11 between the first light emitting side optical member LRS11 and the substrate BD1. As a result, an optical design of the detection device 1 can be simplified.

In addition, since the first light emitting unit L11 is covered with the first light emitting side optical member LRS11, the detection device 1 can inhibit erroneous touching of the first user at the first light emitting unit L11 by the first user and exposure of the first light emitting unit L11 to dust, water, or the like. As a result, the detection device 1 can inhibit occurrence of problems in the first light emitting unit L11. Also, the detection device 1 may have a configuration in which a gap is formed in a part of a space between the first light emitting side optical member LRS11 and the first light emitting unit L11. The first light emitting side optical member LRS11 is an example of the first optical member.

The first light receiving side optical member RRS11 transmits the first light. Also, the first light receiving side optical member RRS11 may be configured to transmit the first light and transmit light in a wavelength band different from the first wavelength band, or may be configured to transmit the first light and not to transmit light in a wavelength band different from the first wavelength band. In the first embodiment, as an example, a case in which the first light receiving side optical member RRS11 transmits the first light and transmits light in a wavelength band different from the first wavelength band will be described. The first light receiving side optical member RRS11 is made of a material that has a refractive index of about 1.4 or more and transmits the first light, for example, a resin that transmits light, such as a transparent epoxy resin or a transparent acrylic resin, but is not limited thereto. In the first embodiment, as an example, a case in which the resin forming the first light receiving side optical member RRS11 is the same resin as the resin forming the first light emitting side optical member LRS11 will be described.

The first light receiving side optical member RRS11 covers the first light receiving unit R11 at the substrate BD1. In other words, the first light receiving side optical member RRS11 and the substrate BD1 surround and enclose the first light receiving unit R11. In the following description, as an example, a case in which the first light receiving side optical member RRS11 is provided at the upper surface of the substrate BD1 so that no gap is generated between itself and the first light receiving unit R11 will be described. In this case, there is no gap between the first light receiving side optical member RRS11 and the first light receiving unit R11 except for a gap unintentionally formed in the manufacturing process. Thus, the detection device 1 can inhibit refraction of the first light incident on the first light receiving side optical member RRS11 between the first light receiving side optical member RRS11 and the substrate BD1.

As a result, the optical design of the detection device 1 can be simplified. In addition, since the first light receiving unit R11 is covered with the first light receiving side optical member RRS11, the detection device 1 can inhibit erroneous touching of the first user at the first light receiving unit R11 and exposure of the first light receiving unit R11 to dust, water, or the like. As a result, the detection device 1 can inhibit occurrence of problems in the first light receiving unit R11. Also, the detection device 1 may have a configuration in which a gap is formed in a part of a space between the first light receiving side optical member RRS11 and the first light receiving unit R11. The first light receiving side optical member RRS11 is an example of the second optical member.

The accommodating member CS1 is provided at the upper surface of the substrate BD1. The accommodating member CS1 is a member that forms an outer shape of the detection device 1 together with each of the substrate BD1 and the coat member URS11. In the following description, in order to simplify the description, as an example, a case in which an outer shape of the accommodating member CS1 is rectangular parallelepiped as a whole, except for various openings formed in the accommodating member CS1, distortions due to manufacturing errors, and the like, will be described. In this case, an upper surface of the accommodating member CS1 is a surface parallel to the substrate BD1. Also, the upper surface of the accommodating member CS1 may be a surface that is not parallel to the substrate BD1. Further, a height of the upper surface of the accommodating member CS1 from the substrate BD1 is determined to be higher than a height of the first light emitting unit L11 from the substrate BD1.

The accommodating member CS1 is made of, for example, an opaque resin with a high light reflectance, a transparent resin mixed with metal powder, a metal, or the like. In the first embodiment, as an example, a case in which the accommodating member CS1 is made of a white epoxy resin that does not substantially transmit visible light and infrared light will be described. Also, in the present disclosure, for convenience of description, the white epoxy resin will be described as a white resin.

Figure 2:
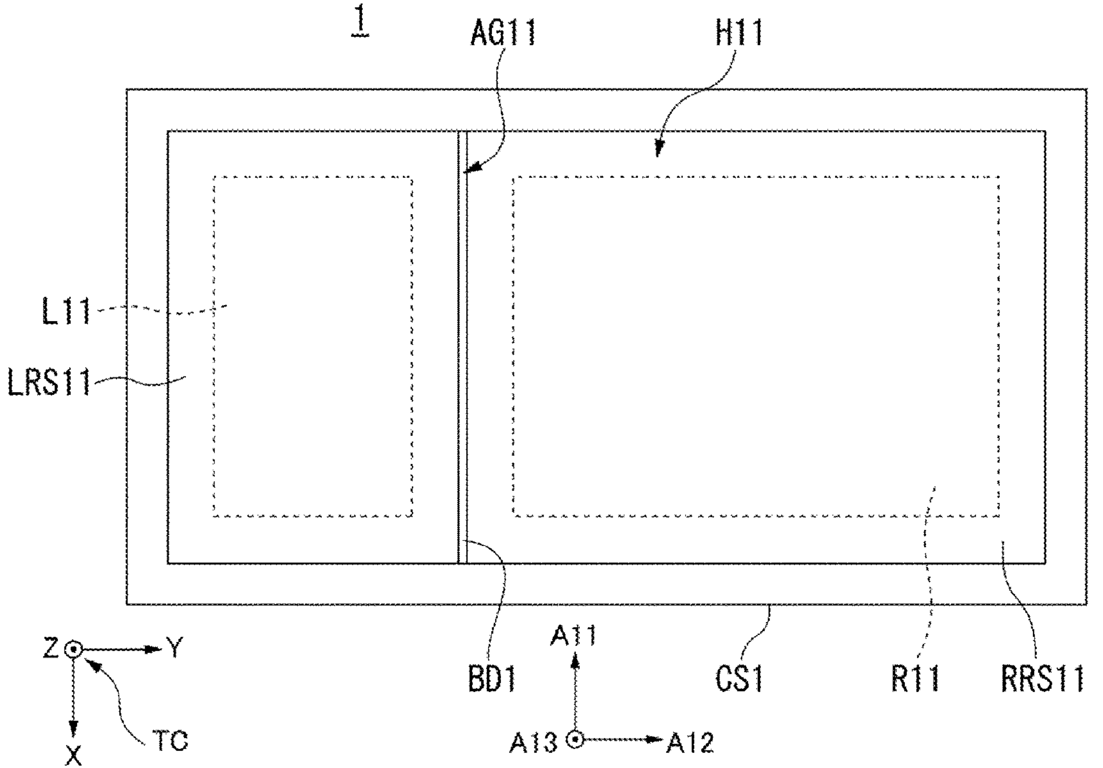
FIG. 2 is a top view of the detection device 1 shown in FIG. 1.
Figure 3:
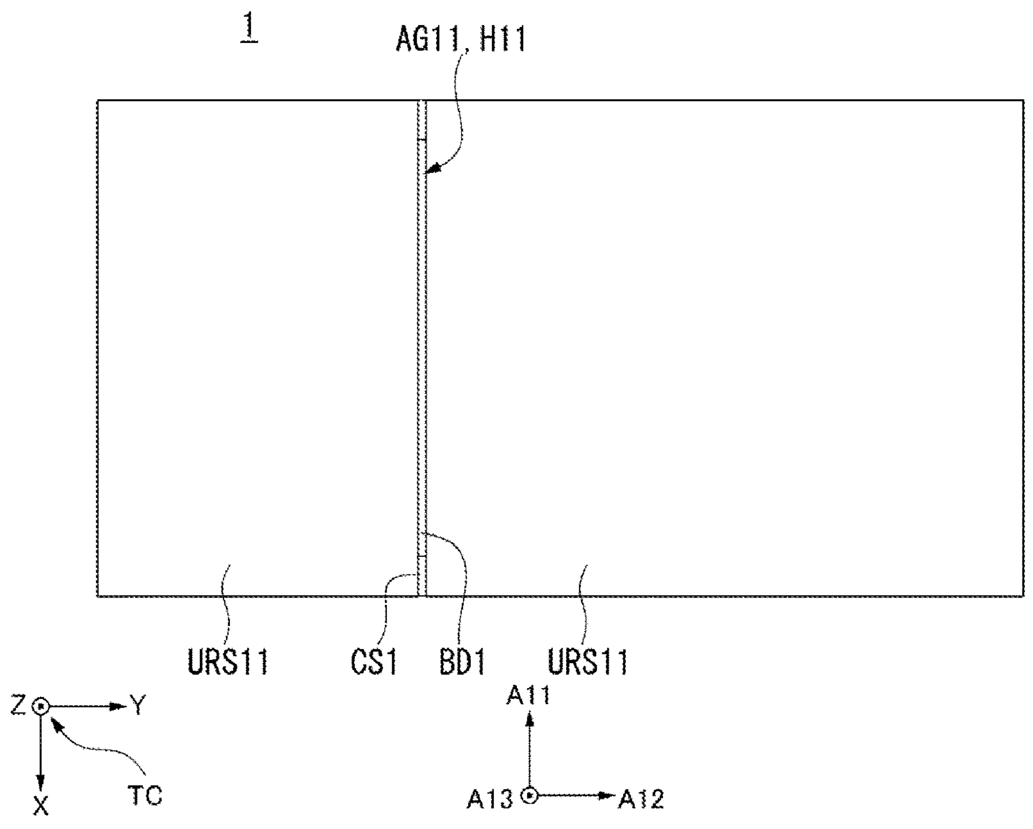
FIG. 3 is a top view of the detection device 1 when a coat member URS11 is not omitted.

Here, a first opening H11 is formed in the accommodating member CS1. FIG. 2 is a top view of the detection device 1 shown in FIG. 1. However, in FIG. 2, in order to clearly show the shape of the accommodating member CS1, the coat member URS11 that is a member covering the upper surface of the detection device 1 is omitted. Also, FIG. 3 is a top view of the detection device 1 when the coat member URS11 is not omitted.

The first opening H11 is a hole that penetrates the accommodating member CS1 in a third direction A13 intersecting the substrate BD1. In the first embodiment, as an example, a case in which the third direction A13 is a direction from the substrate BD1 toward the first light emitting unit L11 of two directions orthogonal to the substrate BD1 will be described. In this case, the third direction A13 is orthogonal to the first direction A11 and the second direction A12 and coincides with the positive direction of the Z axis in each figure used to describe the first embodiment.

In addition, the first opening H11 is a hole at the upper surface of the substrate BD1, in which the first light emitting unit L11, the first light emitting side optical member LRS11, the first light receiving unit R11, and the first light receiving side optical member RRS11 are accommodated. In the example shown in FIGS. 1 and 2, a shape of a contour of the first opening H11 is rectangular when viewed in the first direction A11. Further, in the example, the shape of the contour of the first opening H11 is rectangular when viewed in the third direction A13. That is, the shape of the first opening H11 is a rectangular parallelepiped shape. Also, instead of the rectangular parallelepiped shape, the shape of the first opening H11 may be another shape that can accommodate the first light emitting unit L11, the first light emitting side optical member LRS11, the first light receiving unit R11, and the first light receiving side optical member RRS11 at the upper surface of the substrate BD1. The other shape is, for example, a trapezoid or the like, but is not limited thereto.

The coat member URS11 is a member provided in at least a part of a first surface M11 on a side opposite to a surface in contact with the substrate BD1 among surfaces of the first light receiving side optical member RRS11. The coat member URS11 is a member that makes transmittance of the first light that is incident on the first surface M11 at an angle less than a first angle higher than transmittance of the first light that is incident on the first surface M11 at an angle equal to or greater than the first angle. The coat member URS11 is, for example, an anti-reflection (AR) coating, but instead of this, may be another member that can make the transmittance of the first light that is incident on the first surface M11 at an angle less than the first angle higher than the transmittance of the first light that is incident on the first surface M11 at an angle equal to or greater than the first angle. The first angle is, for example, an angle of 30° or more and 60° or less and is preferably an angle of 42° or more. In the first embodiment, as an example, as shown in FIG. 1, a case in which the coat member URS11 is provided at all of an upper surface of the first light emitting side optical member LRS11 and the upper surface of the accommodating member CS1 in addition to the whole surface of the first surface M11 will be described. In this case, the coat member URS11 covers at least a part of the upper surface of the detection device 1 and forms the upper surface of the detection device 1. Also, the coat member URS11 may have a configuration that does not cover a part of or the whole upper surface of the first light emitting side optical member LRS11. Further, the coat member URS11 may have a configuration that does not cover a part of or the whole upper surface of the accommodating member CS1.

Here, as shown in FIGS. 1 and 2, in the first opening H11 included in the detection device 1, a space between the first light emitting side optical member LRS11 and the first light receiving side optical member RRS11 is a gap AG11. That is, in the second direction A12, the space between the first light emitting side optical member LRS11 and the first light receiving side optical member RRS11 is the gap AG11. In other words, in the first opening H11, the gap AG11 is formed between the first light emitting side optical member LRS11 and the first light receiving side optical member RRS11. In other words, in the first opening H11, there is the gap AG11 formed between the first light emitting side optical member LRS11 and the first light receiving side optical member RRS11. In addition, in the example shown in FIG. 1, a part of the gap AG11 overlaps each of the first light emitting unit L11 and the first light receiving unit R11 in the second direction A12, that is, in a negative direction of the Y axis. More specifically, the lowermost region of a region included in the gap AG11 overlaps each of the first light emitting unit L11 and the first light receiving unit R11. In other words, in that case, the lowermost wall surface of wall surfaces forming the gap AG11 is located below upper surfaces of the first light emitting unit L11 and the first light receiving unit R11.

Further, in this example, an upper side of the gap AG11 is coupled to a region outside the detection device 1. The gap AG11 can be formed, for example, using the following forming method. First, a manufacturer of the detection device 1 provides each of the first light emitting unit L11 and the first light receiving unit R11 at the upper surface of the substrate BD1 by die bonding and wire bonding. After that, using a mold for hardening a resin into a rectangular parallelepiped shape, the manufacturer fills and hardens the resin at the upper surface of the substrate BD1 to cover both the first light emitting unit L11 and the first light receiving unit R11. In this case, a height of the resin at the substrate BD1 is higher than a height of higher one of the first light emitting unit L11 and the first light receiving unit R11 by 0.2 [mm] or more. The resin is a resin that forms each of the first light emitting side optical member LRS11 and the first light receiving side optical member RRS11.

Next, the manufacturer deposits the coat member URS11 at an upper surface of the resin filled at the upper surface of the substrate BD1. Then, the manufacturer cuts the resin filled at the upper surface of the substrate BD1 into two resin parts of the resin covering the first light emitting unit L11 and the resin covering the first light receiving unit R11. The resin covering the first light emitting unit L11 of the two resin parts thus cut is the first light emitting side optical member LRS11.

On the other hand, the resin covering the first light receiving unit R11 of the two resin parts is the first light receiving side optical member RRS11. Also, the manufacturer may cut the resin filled at the upper surface of the substrate BD1 together with the coat member URS11, or may cut only the resin from its side surface. In the example shown in FIGS. 1 to 3, the coat member URS11 is cut into two pieces. That is, in this example, the manufacturer cuts the resin together with the coat member URS11. When the manufacturer cuts only the resin from its side surface, the coat member URS11 provided at the upper surface of the first light emitting side optical member LRS11 and the coat member URS11 provided at the upper surface of the first light receiving side optical member RRS11 may be coupled to each other. Further, in cutting the resin, a configuration in which the manufacturer cuts a part of the upper surface of the substrate BD1 together with the resin may be adopted. In this case, a recessed portion is formed at the upper surface of the substrate BD1, and a space above a lower surface of the formed recessed portion becomes the gap AG11. That is, the gap AG11 overlaps the recessed portion of the substrate BD1. In addition, in the first opening H11, a part of the space between the first light emitting side optical member LRS11 and the first light receiving side optical member RRS11 may be coupled.

Next, the manufacturer pours, for example, the white resin onto the upper surface of the substrate BD1 and hardens it as the accommodating member CS1. In this case, the manufacturer performs masking so that the white resin does not enter the gap AG11. Finally, the manufacturer deposits the coat member URS11 at the upper surface of the accommodating member CS1 formed at the upper surface of the substrate BD1 to complete the detection device 1. Thus, the manufacturer can manufacture the detection device 1 having the configuration in which the gap AG11 as shown in FIG. 1 is formed. Also, a thickness of a wall surface of the accommodating member CS1 is, for example, 0.3 [mm], but is not limited thereto. Further, a width of the gap AG11 in the second direction A12 is 0.05 [mm], but is not limited thereto.

In the detection device 1 configured as described above, the first light emitted from the first light emitting unit L11 is reflected by each of the accommodating member CS1 and the gap AG11. For example, the first light emitted from the first light emitting unit L11 in the direction indicated by arrow LT11 shown in FIG. 1 is an example of the first light emitted from the first light emitting unit L11 toward the accommodating member CS1. The first light emitted from the first light emitting unit L11 in the direction indicated by arrow LT11 is reflected by the accommodating member CS1 and travels in the direction indicated by arrow LT12. In this case, since the first light emitted from the first light emitting unit L11 in the direction indicated by arrow LT11 is incident on the first surface M11 at an angle equal to or greater than the first angle, the first light is transmitted through the coat member URS11 provided in the detection device 1. As a result, the first light is not substantially reflected by the upper surface of the first light emitting side optical member LRS11 and exits to the outside of the detection device 1. That is, the detection device 1 can inhibit the first light from being reflected by the upper surface and becoming stray light in the first light emitting side optical member LRS11. In other words, by including the coat member URS11, the detection device 1 can increase an amount of light entering the skin of the person.

On the other hand, for example, the first light emitted from the first light emitting unit L11 in the direction indicated by arrow LT13 shown in FIG. 1 is an example of the first light emitted from the first light emitting unit L11 toward the first light receiving side optical member RRS11. Some of the first light emitted from the first light emitting unit L11 in the direction indicated by arrow LT13 is reflected at an interface between the first light emitting side optical member LRS11 and the gap AG11, travels in the direction indicated by arrow LT14, and exits to the outside of the detection device 1. Thus, the detection device 1 can inhibit an amount of the first light that becomes stray light incident on the first light receiving side optical member RRS11 without entering the skin of the person.

Also, in the first light emitted from the first light emitting unit L11 in the direction indicated by arrow LT13, the first light transmitted without being reflected at the interface between the first light emitting side optical member LRS11 and the gap AG11 is refracted at each of the interface between the first light emitting side optical member LRS11 and the gap AG11 and an interface between the first light receiving side optical member RRS11 and the gap AG11, and then travels along arrow LT15 shown in FIG. 1 toward the coat member URS11 provided at the upper surface of the first light receiving side optical member RRS11. The first light incident on the coat member URS11 is incident on the first surface M11 at an angle equal to or greater than the first angle and is transmitted through the coat member URS11. That is, the first light is not reflected by the upper surface of the first light receiving side optical member RRS11 and exits to the outside of the detection device 1. Thus, the detection device 1 can inhibit the first light from becoming stray light in the first light receiving side optical member RRS11.

As described above, since the detection device 1 includes the coat member URS11 and the gap AG11 is formed, the amount of the first light emitted from the first light emitting unit L11 that enters the skin of the person can be increased, and the amount of the first light that becomes stray light entering the first light receiving side optical member RRS11 can be inhibited. This leads to inhibiting a decrease in the amount of light received by the first light receiving unit R11, which is useful.

Also, the detection device 1 has the gap AG11 formed between the first light emitting side optical member LRS11 and the first light receiving side optical member RRS11, and thus, as compared with a case in which a resin, a metal, or the like is disposed instead of the gap AG11, the amount of light received by the first light receiving unit R11 can be increased by bringing the first light emitting unit L11 and the first light receiving unit R11 closer together, and its size in the second direction A12 can be reduced. That is, the detection device 1 can achieve reduction in its size while inhibiting reduction in the amount of light received by the first light receiving unit R11. In addition, even when the detection device 1 does not include the coat member URS11, the first light incident on the first light receiving side optical member RRS11 from the first light emitting side optical member LRS11 is reflected by the interface between the first light emitting side optical member LRS11 and the gap AG11, and thus it is possible to inhibit the first light from becoming stray light entering the first light receiving side optical member RRS11 without entering the skin of the person. For this reason, even in that case, the detection device 1 can achieve reduction in its size while inhibiting reduction in the amount of light received by the first light receiving unit R11. Further, in the detection device 1, the gap AG11 is formed between the first light emitting side optical member LRS11 and the first light receiving side optical member RRS11, and thus, as compared with the case in which a resin, a metal, or the like is disposed instead of the gap AG11, it is possible to reduce costs such as material costs for using a resin, a metal, or the like.

Figure 4:
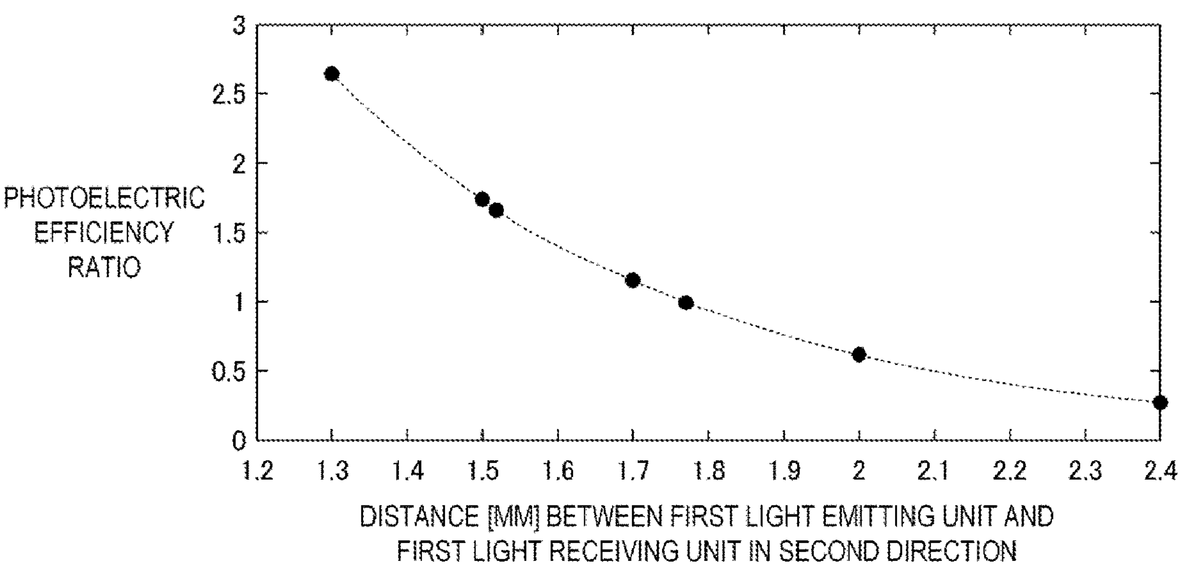
FIG. 4 is a diagram showing an example of a change in a photoelectric efficiency ratio when a distance between a first light emitting unit L11 and a first light receiving unit R11 in a second direction A12 is changed.

Here, FIG. 4 is a diagram showing an example of a change in a photoelectric efficiency ratio when a distance between the first light emitting unit L11 and the first light receiving unit R11 in the second direction A12 is changed. The photoelectric efficiency ratio is a ratio of second photoelectric efficiency to first photoelectric efficiency. The first photoelectric efficiency is photoelectric efficiency in the detection device 1 when the white resin is disposed instead of the gap AG11. The second photoelectric efficiency is photoelectric efficiency in the detection device 1 shown in FIG. 1. In addition, the photoelectric efficiency is a ratio of an amount of the first light received by the first light emitting unit L11, which was reflected in the skin of the person, to an amount of the first light emitted by the first light emitting unit L11.

Also, the graph shown in FIG. 4 is an example of results of an experiment performed in advance by the applicant. The horizontal axis of the graph indicates the distance between the first light emitting unit L11 and the first light receiving unit R11 in the second direction A12. The vertical axis of the graph indicates the photoelectric efficiency ratio. Referring to FIG. 4, it can be seen that as the distance between the first light emitting unit L11 and the first light receiving unit R11 in the second direction A12 decreases, the photoelectric ratio increases. For example, the graph shows that, by setting the distance between the first light emitting unit L11 and the first light receiving unit R11 in the second direction A12 to about 1.43 [mm], the photoelectric efficiency of the detection device 1 shown in FIG. 1 can be set to be about twice the photoelectric efficiency of the detection device 1 when the white resin is disposed instead of the gap AG11.

This means that, when the gap AG11 is formed in the detection device 1 as shown in FIG. 1, the distance between the first light emitting unit L11 and the first light receiving unit R11 in the second direction A12 can be made shorter than that in the detection device 1 of the case in which the white resin is disposed instead of the gap AG11, and as a result, photoelectric efficiency can be improved. Further, each of the above-described reflection of the first light by the gap AG11 and transmission of the first light by the coat member URS11 also contribute to such an increase in the photoelectric efficiency.

Figure 5:
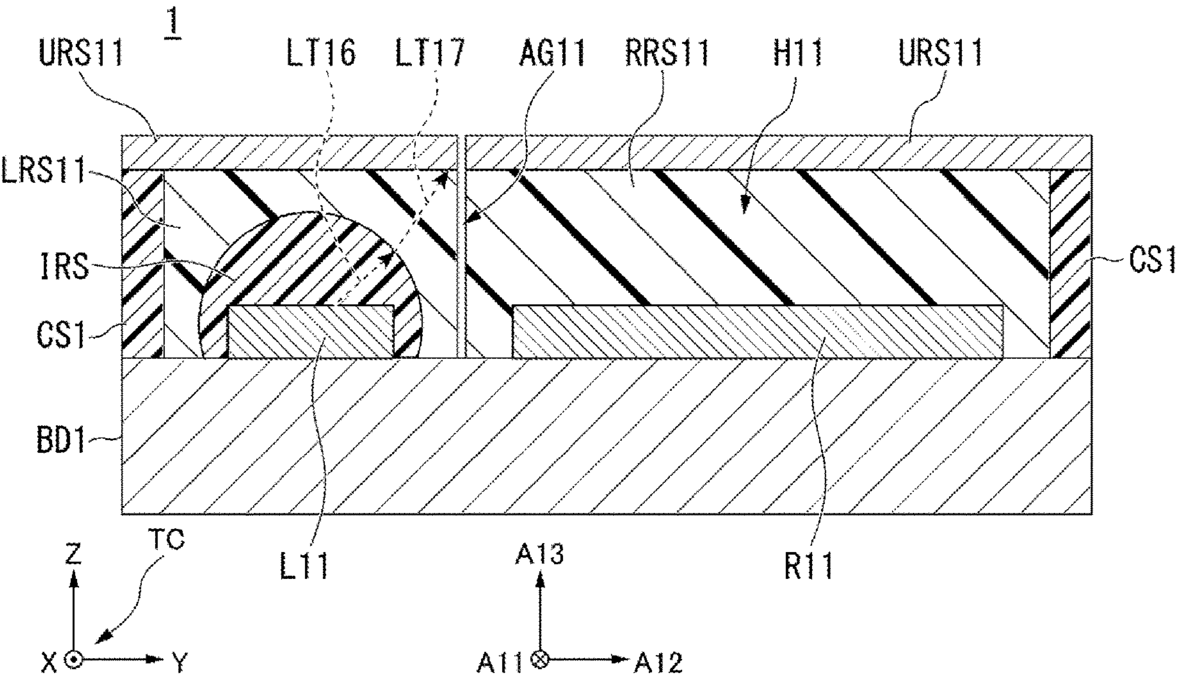
FIG. 5 is a cross-sectional view showing a second configuration example of the detection device 1.
Figure 6:
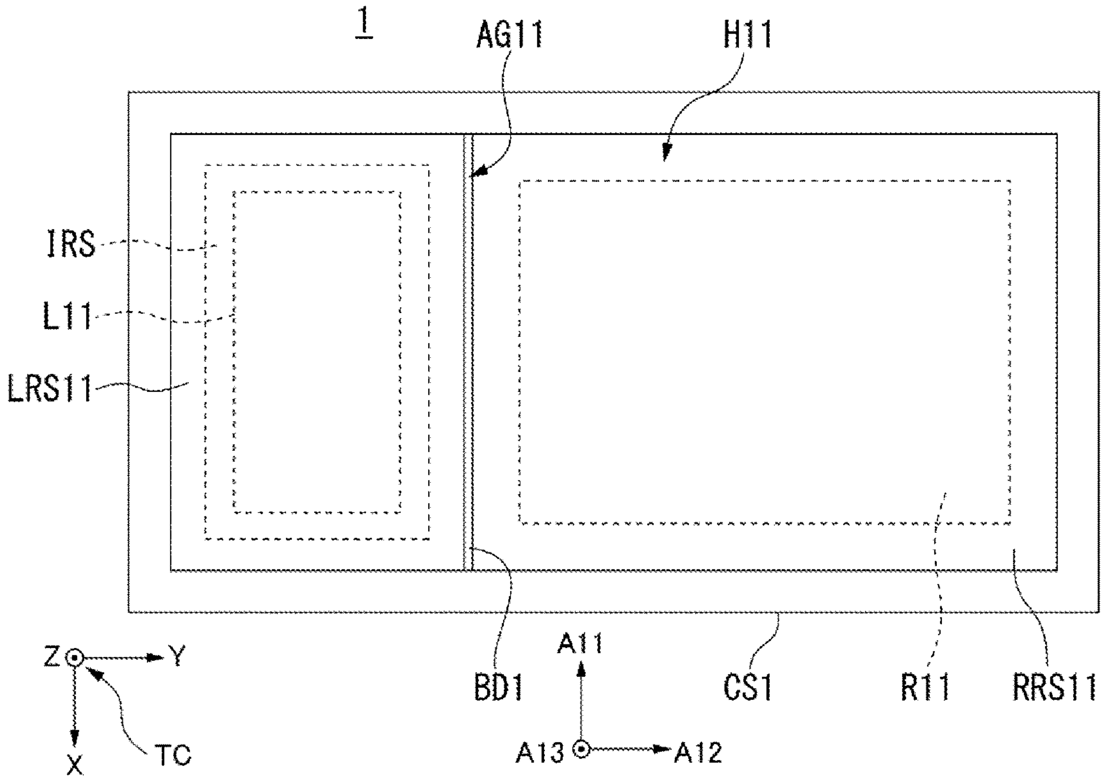
FIG. 6 is a top view of the detection device 1 shown in FIG. 5.

Also, the detection device 1 according to the first embodiment may be configured to include an optical member IRS as shown in FIGS. 5 and 6. FIG. 5 is a cross-sectional view showing a second configuration example of the detection device 1. The cross-sectional view shown in FIG. 5 is also a cross-sectional view of the detection device 1 along a virtual plane orthogonal to the first direction A11 so that the first light emitting unit L11 and the first light receiving unit R11 can be seen when viewed in the first direction A11. FIG. 6 is a top view of the detection device 1 shown in FIG. 5. However, in FIG. 6, in order to clearly show a positional relationship between the optical member IRS and the first light emitting side optical member LRS11, the coat member URS11 is omitted.

The optical member IRS is an optical member that transmits the first light and has a refraction index greater than a refraction index of the first light emitting side optical member LRS11 by 0.05 or more. The optical member IRS may be configured to transmit the first light and transmit light in a wavelength band different from the first wavelength band, or may be configured to transmit the first light and not to transmit light in a wavelength band different from the first wavelength band. In the following description, as an example, a case in which the optical member IRS transmits the first light and transmits light in a wavelength band different from the first wavelength band will be described. The optical member IRS is made of, for example, a transparent resin having a refraction index greater than the refraction index of the first light emitting side optical member LRS11 by 0.05 or more, but is not limited thereto. Further, the refractive index of the optical member IRS is more preferably 1.65 or more.

The optical member IRS is interposed between the first light emitting side optical member LRS11 and the first light emitting unit L11 and covers the first light emitting unit L11 at the substrate BD1. For this reason, when the detection device 1 includes the optical member IRS, as shown in FIGS. 5 and 6, the first light emitting side optical member LRS11 covers the first light emitting unit L11 by covering the optical member IRS at the substrate BD1. That is, for example, the manufacturer of the detection device 1 fills and hardens the resin forming the optical member IRS at the upper surface of the substrate BD1 before the resins forming each of the first light emitting side optical member LRS11 and the first light receiving side optical member RRS11 at the upper surface of the substrate BD1. In the following description, as an example, a case in which the optical member IRS is provided at the upper surface of the substrate BD1 so that no gap is generated between the optical member IRS and the first light emitting unit L11 will be described. In this case, there is no gap between the optical member IRS and the first light emitting unit L11 except for a gap unintentionally formed in the manufacturing process. Thus, the detection device 1 can inhibit refraction of the first light emitted from the first light emitting unit L11 between the optical member IRS and the substrate BD1. As a result, the optical design of the detection device 1 can be simplified. Also, the optical member IRS is an example of a fifth optical member.

Among surfaces of the optical member IRS, a surface on a side opposite to the substrate BD1 may include a surface having a positive gradient in the third direction Al3. In the example shown in FIGS. 5 and 6, a shape of the optical member IRS is a dome shape that covers the first light emitting unit L11. For this reason, among the surfaces of the optical member IRS, the surface on the side opposite to the substrate BD1 includes a curved surface having the above-described positive gradient in the third direction A13.

The first light emitted from the first light emitting unit L11 in the direction indicated by arrow LT16 shown in FIG. 5 is an example of the first light emitted from the first light emitting unit L11 toward the first light receiving side optical member RRS11. Here, the first light emitting unit L11 is covered with the dome-shaped optical member IRS. Also, the refraction index of the optical member IRS is greater than the refraction index of the first light emitting side optical member LRS11. For these reasons, the first light emitted from the first light emitting unit L11 in the direction indicated by arrow LT16 is refracted at an interface between the optical member IRS and the first light emitting side optical member LRS11 and is refracted in the direction indicated by arrow LT17. The direction indicated by arrow LT17 is a direction separating from the first light receiving unit R11. Also, the direction separating from the first light receiving unit R11 may be referred to as a direction closer to the third direction A13 than a traveling direction of the first light before the refraction.

In the example shown in FIG. 5, the direction indicated by arrow LT17 is a direction separating from the first light receiving unit R11 and a direction toward the coat member URS11 provided at the upper surface of the first light emitting side optical member LRS11. In addition, the direction indicated by arrow LT17 is a direction that is closer to the third direction A13 than the direction indicated by arrow LT16. For this reason, the first light traveling in the direction indicated by arrow LT17 is not substantially reflected at the upper surface of the first light emitting side optical member LRS11 and exits to the outside of the detection device 1.

That is, by including the optical member IRS, the detection device 1 can more reliably inhibit the first light from becoming stray light in the first light emitting side optical member LRS11 without entering the skin of the person, and as a result, can increase the amount of light entering the skin of the person. This leads to improving a signal (S)/noise (N) ratio in pulse detection by the detection device 1, which is useful. Also, instead of the dome shape, the shape of the optical member IRS may be another shape such as a triangular pyramid shape or a quadrangular pyramid shape as long as the shape can refract the first light emitted from the first light emitting unit L11 toward the first light receiving side optical member RRS11 at the interface between the first light emitting side optical member LRS11 and the optical member IRS in a direction separating from the first light receiving unit R11 when viewed in the first direction A11.

Figure 7:
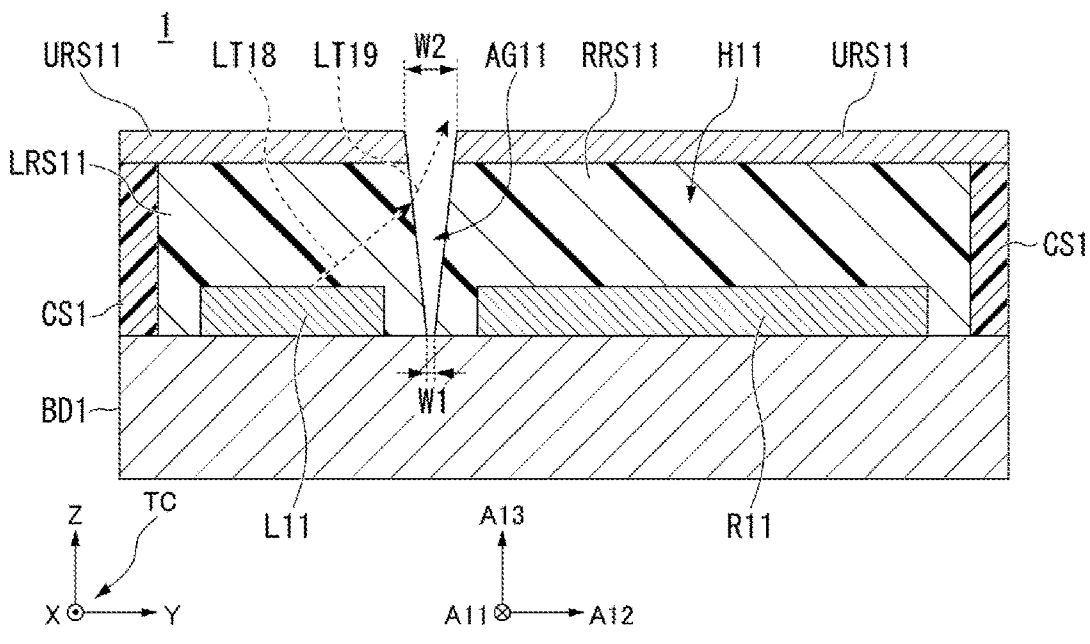
FIG. 7 is a cross-sectional view showing a third configuration example of the detection device 1.

In addition, as shown in FIG. 7, the detection device 1 according to the first embodiment may have a configuration in which a length of the gap AG11 in the second direction A12 increases as a distance from the substrate BD1 increases in the direction intersecting the substrate BD1. FIG. 7 is a cross-sectional view showing a third configuration example of the detection device 1. Further, the cross-sectional view shown in FIG. 7 is also a cross-sectional view of the detection device 1 along a virtual plane orthogonal to the first direction A11 so that the first light emitting unit L11 and the first light receiving unit R11 can be seen when viewed in the first direction A11.

In the example shown in FIG. 7, the length of the gap AG11 in the second direction A12 increases as the distance from the substrate BD1 increases in the third direction A13. For example, in this example, a width W2 is longer than a width W1. The width W2 shown in FIG. 7 indicates an example of a length of the uppermost portion of the gap AG11 in the second direction A12, that is, a length of the gap AG11 in the second direction A12 at a portion farthest from the substrate BD1. The width W1 shown in FIG. 7 indicates an example of a length of the lowermost portion of the gap AG11 in the second direction A12, that is, a length of the gap AG11 in the second direction A12 at a portion closest to the substrate BD1.

The first light emitted from the first light emitting unit L11 in the direction indicated by arrow LT18 shown in FIG. 7 is an example of the first light emitted from the first light emitting unit L11 toward the first light receiving side optical member RRS11. The first light emitted from the first light emitting unit L11 in the direction indicated by arrow LT18 is refracted by the interface between the first light emitting side optical member LRS11 and the gap AG11 in the direction indicated by arrow LT19 before it reaches the first light receiving side optical member RRS11. The direction indicated by arrow LT19 is a direction separating from the first light receiving unit R21. Also, as described above, the direction separating from the first light receiving unit R21 may be referred to as a direction closer to the third direction A13 than the traveling direction of the first light before the refraction.

In the example shown in FIG. 7, the direction separating from the first light receiving unit R11 is indicated by arrow LT19. In addition, in this example, the direction indicated by arrow LT19 is a direction toward the outside of the detection device 1 through the gap AG11 and is a direction closer to the third direction A13 than the direction indicated by arrow LT18. For this reason, the first light traveling in the direction indicated by arrow LT19 is emitted to the outside of the detection device 1 without being incident on the first light receiving side optical member RRS11. That is, since the configuration of the gap AG11 is as shown in FIG. 7, the detection device 1 can more reliably inhibit the first light from becoming stray light in the first light receiving side optical member RRS11. As a result, the detection device 1 can increase the amount of the first light entering the skin of the person. This leads to improvement in a S/N ratio in pulse detection by the detection device 1, which is useful.

Figure 8:
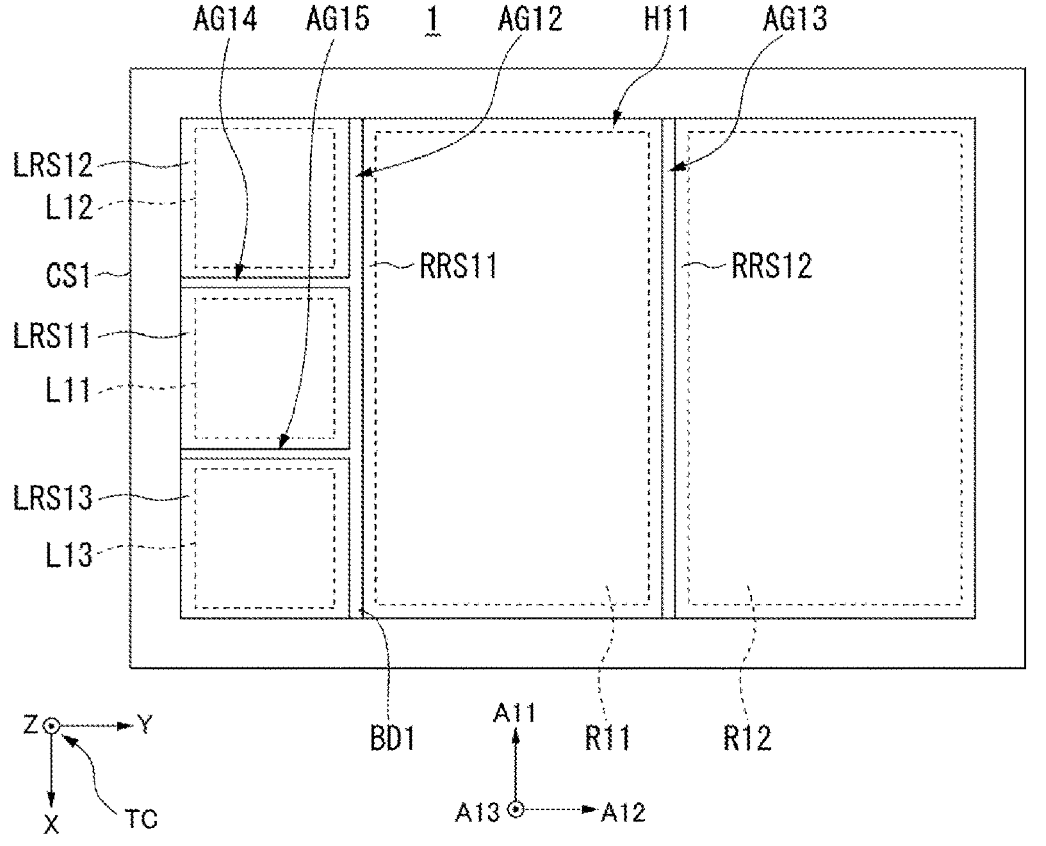
FIG. 8 is a top view showing a fourth configuration example of the detection device 1.

Also, as shown in FIG. 8, the detection device 1 according to the first embodiment may be configured to include the substrate BD1, the first light emitting unit L11, a second light emitting unit L12, a third light emitting unit L13, the first light receiving unit R11, a second light receiving unit R12, the first light emitting side optical member LRS11, a second light emitting side optical member LRS12, a third light emitting side optical member LRS13, the first light receiving side optical member RRS11, a second light receiving side optical member RRS12, the accommodating member CS1, and the coat member URS11. FIG. 8 is a top view showing a fourth configuration example of the detection device 1. However, in FIG. 8, in order to clearly show the positional relationship among the first light emitting side optical member LRS11, the first light receiving side optical member RRS11, the second light emitting side optical member LRS12, the third light emitting side optical member LRS13, and the second light receiving side optical member RRS12, the coat member URS11 is omitted.

The second light emitting unit L12 is provided at the upper surface of the substrate side BD1 side by side with the first light emitting unit L11 in the first direction A11. In the example shown in FIG. 8, the second light emitting unit L12 is provided to be adjacent to the first light emitting unit L11 in the first direction A11. The second light emitting unit L12 is a light emitting element, a light emitting device, or the like that emits light in a predetermined second wavelength band as second light. The second light emitting unit L12 is, for example, an LED, but instead of this, it may be another light emitting element or another light emitting device such as an OLED, a uLED, or a VCSEL. In the first embodiment, as an example, a case in which the second wavelength band is a red wavelength band will be described. In this case, the second light emitting unit L12 emits red light as the second light. Also, in the first embodiment, in each figure in which the second light emitting unit L12 is drawn, in order to prevent the figures from becoming complicated, members for coupling the transmission path at the substrate BD1 to the second light emitting unit L12 are omitted. Here, the members are, for example, wire bonding, coupling terminals and the like, but are not limited thereto. The second light emitting unit L12 is an example of a second light emitting unit.

The third light emitting unit L13 is provided at the upper surface of the substrate side BD1 side by side with the first light emitting unit L11 in the first direction A11. In the example shown in FIG. 8, the third light emitting unit L13 is provided to be adjacent to the first light emitting unit L11 in a direction opposite to the first direction A11. That is, in the example, the first light emitting unit L11 is interposed between the second light emitting unit L12 and the third light emitting unit L13 in the first direction A11. The third light emitting unit L13 is a light emitting element, a light emitting device, or the like that emits light in a predetermined third wavelength band as third light. The third light emitting unit L13 is, for example, an LED, but instead of this, it may be another light emitting element or another light emitting device such as an OLED, a uLED, or a VCSEL. In the first embodiment, as an example, a case in which the third wavelength band is an infrared wavelength band will be described. In this case, the third light emitting unit L13 emits infrared light as the third light. Also, in the first embodiment, in each figure in which the third light emitting unit L13 is drawn, in order to prevent the figures from becoming complicated, members for coupling the transmission path at the substrate BD1 to the third light emitting unit L13 are omitted. Here, the members are, for example, wire bonding, coupling terminals, and the like, but are not limited thereto. The third light emitting unit L13 is an example of a third light emitting unit.

The second light receiving unit R12 is provided at the substrate BD1 side by side with the first light receiving unit R11 in the second direction A12. In the example shown in FIG. 8, the second light receiving unit R12 is provided to be adjacent to the first light receiving unit R11 in the second direction A12. The second light receiving unit R12 is a light receiving element, a light receiving device, or the like that receives each of the second light emitted by the second light emitting unit L12 and the third light emitted by the third light emitting unit L13.

Also, the second light receiving unit R12 may have a configuration that can receive the second light and the third light and can receive light in a wavelength band different from each of the second wavelength band and the third wavelength band, or may have a configuration that can receive the second light and the third light but cannot receive light in a wavelength band different from each of the second wavelength band and the third wavelength band. The configuration that cannot receive light in a wavelength band different from the second wavelength band and the third wavelength band is realized by, for example, a band-pass filter or the like. In the first embodiment, as an example, a case in which the second light receiving unit R12 can receive the second light and the third light and can receive light in a wavelength band different from the second wavelength band and the third wavelength band will be described. Also, in the first embodiment, in each figure in which the second light receiving unit R12 is drawn, in order to prevent the figures from becoming complicated, members for coupling the transmission path at the substrate BD1 to the second light receiving unit R12 are omitted. Here, the members are, for example, wire bonding, coupling terminals, and the like, but are not limited thereto. The second light receiving unit R12 is an example of a second light receiving unit.

The second light emitting side optical member LRS12 transmits the second light. Also, the second light emitting side optical member LRS12 may be configured to transmit the second light and transmit light in a wavelength band different from the second wavelength band, or may be configured to transmit the second light and not to transmit light in a wavelength band different from the second wavelength band. In the first embodiment, as an example, a case in which the second light emitting side optical member LRS12 transmits the second light and transmits light in a wavelength band different from the second wavelength band will be described. The second light emitting side optical member LRS12 is made of, for example, a resin that transmits light, such as a transparent epoxy resin or a transparent acrylic resin, but is not limited thereto. In the first embodiment, as an example, a case in which the resin forming the second light emitting side optical member LRS12 is the same resin as the resin forming the first light emitting side optical member LRS11 will be described.

The second light emitting side optical member LRS12 covers the second light emitting unit L12 at the substrate BD1. In other words, the second light emitting side optical member LRS12 and the substrate BD1 surround and enclose the second light emitting unit L12. In the first embodiment, as an example, a case in which the second light emitting side optical member LRS12 is provided at the upper surface of the substrate BD1 so that no gap is generated between the second light emitting side optical member LRS12 and the second light emitting unit L12 will be described.

In this case, there is no gap between the second light emitting side optical member LRS12 and the second light emitting unit L12 except for a gap unintentionally formed in the manufacturing process. Thus, the detection device 1 can inhibit refraction of the second light emitted from the second light emitting unit L12 between the second light emitting side optical member LRS12 and the substrate BD1. As a result, the optical design of the detection device 1 can be simplified. In addition, since the second light emitting unit L12 is covered with the second light emitting side optical member LRS12, the detection device 1 can inhibit erroneous touching of the first user at the second light emitting unit L12 and exposure of the second light emitting unit L12 to dust, water, or the like. As a result, the detection device 1 can inhibit occurrence of problems in the second light emitting unit L12. Also, the detection device 1 may have a configuration in which a gap is formed in a part of a space between the second light emitting side optical member LRS12 and the second light emitting unit L12. The second light emitting side optical member LRS12 is an example of a third optical member.

The third light emitting side optical member LRS13 transmits the third light. Also, the third light emitting side optical member LRS13 may be configured to transmit the third light and transmit light in a wavelength band different from the third wavelength band, or may be configured to transmit the third light and not to transmit light in a wavelength band different from the third wavelength band. In the first embodiment, as an example, a case in which the third light emitting side optical member LRS13 transmits the third light and transmits light in a wavelength band different from the third wavelength band will be described. The third light emitting side optical member LRS13 is made of, for example, a resin that transmits light, such as a transparent epoxy resin or a transparent acrylic resin, but is not limited thereto. In the first embodiment, as an example, a case in which the resin forming the third light emitting side optical member LRS13 is the same resin as the resin forming the first light emitting side optical member LRS11 will be described.

The third light emitting side optical member LRS13 covers the third light emitting unit L13 at the substrate BD1. In other words, the third light emitting side optical member LRS13 and the substrate BD1 surround and enclose the third light emitting unit L13. In the first embodiment, as an example, a case in which the third light emitting side optical member LRS13 is provided at the upper surface of the substrate BD1 so that no gap is generated between the third light emitting side optical member LRS13 and the third light emitting unit L13 will be described. In this case, there is no gap between the third light emitting side optical member LRS13 and the third light emission unit L13 except for a gap unintentionally formed in the manufacturing process.

Thus, the detection device 1 can inhibit refraction of the third light emitted from the third light emitting unit L13 between the third light emitting side optical member LRS13 and the substrate BD1. As a result, the optical design of the detection device 1 can be simplified. In addition, since the third light emitting unit L13 is covered with the third light emitting side optical member LRS13, the detection device 1 can inhibit erroneous touching of the first user at the third light emitting unit L13 and exposure of the third light emitting unit L13 to dust, water, or the like. As a result, the detection device 1 can inhibit occurrence of problems in the third light emitting unit L13. Also, the detection device 1 may have a configuration in which a gap is formed in a part of a space between the third light emitting side optical member LRS13 and the third light emitting unit L13. The third light emitting side optical member LRS13 is an example of a third optical member.

The second light receiving side optical member RRS12 transmits the second light and the third light. Also, the second light receiving side optical member RRS12 may be configured to transmit the second light and the third light and transmit light in a wavelength band different from the second wavelength band and the third wavelength band, or may be configured to transmit the second light and the third light and not to transmit light in a wavelength band different from the second wavelength band and the third wavelength band. In the first embodiment, as an example, a case in which the second light receiving side optical member RRS12 transmits the second light and the third light and transmits light in a wavelength band different from the second wavelength band and the third wavelength band will be described. The second light receiving side optical member RRS12 is made of, for example, a resin that transmits light, such as a transparent epoxy resin or a transparent acrylic resin, but is not limited thereto. In the first embodiment, as an example, a case in which the resin forming the second light receiving side optical member RRS12 is the same resin as the resin forming the first light emitting side optical member LRS11 will be described.

The second light receiving side optical member RRS12 covers the second light receiving unit R12 at the substrate BD1. In other words, the second light receiving side optical member RRS12 and the substrate BD1 surround and enclose the second light receiving unit R12. In the first embodiment, as an example, a case in which the second light receiving side optical member RRS12 is provided at the upper surface of the substrate BD1 so that no gap is generated between itself and the second light receiving unit R12 will be described.

In this case, there is no gap between the second light receiving side optical member RRS12 and the second light receiving unit R12 except for a gap unintentionally formed in the manufacturing process. Thus, the detection device 1 can inhibit refraction of the second light and the third light, which are incident on the second light receiving side optical member RRS12, between the second light receiving side optical member RRS12 and the substrate BD1. As a result, the optical design of the detection device 1 can be simplified. In addition, since the second light receiving unit R12 is covered with the second light receiving side optical member RRS12, the detection device 1 can inhibit erroneous touching of the first user at the second light receiving unit R12 and exposure of the second light receiving unit R12 to dust, water, or the like. As a result, the detection device 1 can inhibit occurrence of problems in the second light receiving unit R12. Also, the detection device 1 may have a configuration in which a gap is formed in a part of a space between the second light receiving side optical member RRS12 and the second light receiving unit R12. The second light receiving side optical member RRS12 is an example of a fourth optical member.

In the detection device 1 shown in FIG. 8, the coat member URS11 is provided at the upper surfaces of each of the first light emitting side optical member LRS11, the second light emitting side optical member LRS12, the third light emitting side optical member LRS13, the first light receiving side optical member RRS11, the second light receiving side optical member RRS12, and the accommodating member CS1. In addition, a part or all of the coat member URS11 provided at these upper surfaces may be coupled to each other or may be separated from each other. Also, in the detection device 1, the coat member URS11 may have a configuration in which it is not provided at a part of or the whole upper surface of the first light emitting side optical member LRS11. Also, in the detection device 1, the coat member URS11 may have a configuration in which it is not provided at a part of or the whole upper surface of the second light emitting side optical member LRS12. Also, in the detection device 1, the coat member URS11 may have a configuration in which it is not provided at a part of or the whole upper surface of the third light emitting side optical member LRS13. Also, in the detection device 1, the coat member URS11 may have a configuration in which it is not provided at a part of or the whole upper surface of the first light receiving side optical member RRS11. Also, in the detection device 1, the coat member URS11 may have a configuration in which it is not provided at a part of or the whole upper surface of the second light receiving side optical member RRS12. Also, in the detection device 1, the coat member URS11 may have a configuration in which it is not provided at a part of or the whole upper surface of the accommodating member CS1.

As described above, the detection device 1 shown in FIG. 8 emits green light using the first light emitting unit L11, emits red light using the second light emitting unit L12, and emits infrared light using the third light emitting unit L13. At least some of the green light emitted by the first light emitting unit L11 is reflected in the skin of the person. Here, the green light has a shorter mean free path in the skin of the person than the red light and the infrared light. For this reason, the reflected light of the green light is more easily received by the first light receiving unit R11 closer to the first light emitting unit L11 than the second light receiving unit R12.

On the other hand, at least some of the red light emitted by the second light emitting unit L12 is also reflected in the skin of the person. However, the red light has a longer mean free path in the skin of the person than the green light. For this reason, the reflected light of the red light is more likely to be received by the second light receiving unit R12 farther from the second light emitting unit L12 than the first light receiving unit R11. Similarly, at least some of the infrared light emitted by the third light emitting unit L13 is also reflected in the skin of the person. However, the infrared light has a longer mean free path in the skin of the person than the green light. For this reason, the reflected light of the infrared light is more likely to be received by the second light receiving unit R12 farther from the third light emitting unit L13 than the first light receiving unit R11.

Due to such circumstances, the detection device 1 detects an amount of the green light using the first light receiving unit R11 and detects amounts of the red light and the infrared light using the second light receiving unit R12. Thus, the detection device 1 can detect both the pulse of the person and the oxygen saturation of the person. In addition, the red light and the infrared light received by the first light receiving unit R11 become noise in the detection of the green light by the first light receiving unit R11. Also, the green light received by the second light receiving unit R12 becomes noise in the detection of the red light and the infrared light by the second light receiving unit R12.

Here, as shown in FIG. 8, a space between three optical members, that is, the first light emitting side optical member LRS11, the second light emitting side optical member LRS12, and the third light emitting side optical member LRS13, and the first light receiving side optical member RRS11 in the first opening H11 included in the detection device 1 is a gap AG12. In other words, in the first opening H11, the gap AG12 is formed between the three optical members and the first light receiving side optical member RRS11. In other words, in the first opening H11, there is the gap AG12 formed between the three optical members and the first light receiving side optical member RRS11.

Thus, as compared with a case in which a resin, a metal, or the like is disposed instead of the gap AG12, the detection device 1 can increase the amount of light received by the two light receiving units by bringing the three light emitting units, that is, the first light emitting unit L11, the second light emitting unit L12, and the third light emitting unit L13, and the two light receiving units, that is, the first light receiving unit R11 and the second light receiving unit R12, closer to each other, and can reduce its size in the second direction A12. That is, the detection device 1 can achieve reduction in size while inhibiting a decrease in the amount of light received by the two light receiving units. Also, the gap AG12 can be formed by, for example, the same forming method as that of the gap AG11.

In addition, when there is the gap AG12 in the first opening H11, the detection device 1 can inhibit three light beams of the first light emitted from the first light emitting unit L11, the second light emitted from the second light emitting unit L12, and the third light emitted from the third light emitting unit L13 from becoming stray light incident on the first light receiving side optical member RRS11 without entering the skin of the person. The reason for this is the same as the reason why the first light can be inhibited from becoming stray light due to being reflected by the interface between the first light emitting side optical member LRS11 and the gap AG11.

Also, as shown in FIG. 8, a space between the first light receiving side optical member RRS11 and the second light receiving side optical member RRS12 in the first opening H11 included in the detection device 1 is a gap AG13. In other words, in the first opening H11, the gap AG13 is formed between the first light receiving side optical member RRS11 and the second light receiving side optical member RRS12. In other words, in the first opening H11, there is the gap AG13 formed between the first light receiving side optical member RRS11 and the second light receiving side optical member RRS12. Thus, as compared with the case in which a resin, a metal, or the like is disposed instead of the gap A13, the detection device 1 can reduce its size in the second direction A12 by bringing the first light receiving side optical member RRS11 and the second light receiving side optical member RRS12 closer to each other. That is, since the gap AG13 is formed, the detection device 1 can detect both the pulse and the oxygen saturation of the person while inhibiting an increase in the size in the second direction A12. Also, the gap AG13 can be formed by, for example, the same forming method as that of the gap AG11.

In the green light reflected in the skin of the person and incident on the first light receiving side optical member RRS11, at least some of the green light passing through the first light receiving side optical member RRS11 and incident on the second light receiving side optical member RRS12 is reflected at each of an interface between the first light receiving side optical member RRS11 and the gap AG13 and an interface between the second light receiving side optical member RRS12 and the gap AG13. For this reason, since the gap AG13 is formed, the detection device 1 can inhibit the first light from becoming stray light incident on the second light receiving side optical member RRS12. Similarly, in the red light reflected in the skin of the person and incident on the second light receiving side optical member RRS12, at least some of the red light passing through the second light receiving side optical member RRS12 and incident on the first light receiving side optical member RRS11 is reflected at each of the interface between the second light receiving side optical member RRS12 and the gap AG13 and the interface between the first light receiving side optical member RRS11 and the gap AG13. For this reason, since the gap AG13 is formed, the detection device 1 can inhibit the second light from becoming stray light incident on the first light receiving side optical member RRS11.

In addition, in the infrared light reflected in the skin of the person and incident on the second light receiving side optical member RRS12, at least some of the infrared light passing through the second light receiving side optical member RRS12 and incident on the first light receiving side optical member RRS11 is reflected at each of the interface between the second light receiving side optical member RRS12 and the gap AG13 and the interface between the first light receiving side optical member RRS11 and the gap AG13. For this reason, since the gap AG13 is formed, the detection device 1 can inhibit the third light from becoming stray light incident on the first light receiving side optical member RRS11.

Also, the detection device 1 may have a configuration in which the gap AG13 is not formed. In this case, the first light receiving side optical member RRS11 and the second light receiving side optical member RRS12 are integrally formed.

Also, as shown in FIG. 8, a space between the first light emitting side optical member LRS11 and the second light emitting side optical member LRS12 in the first opening H11 included in the detection device 1 is a gap AG14. In other words, in the first opening H11, the gap AG14 is formed between the first light emitting side optical member LRS11 and the second light emitting side optical member LRS12. In other words, in the first opening H11, there is the gap AG14 formed between the first light emitting side optical member LRS11 and the second light emitting side optical member LRS12. Thus, as compared with the case in which a resin, a metal, or the like is disposed instead of the gap AG14, the detection device 1 can reduce its size in the first direction A11 by bringing the first light emitting unit L11 and the second light emitting unit L12 closer to each other. Also, the gap AG14 can be formed by, for example, the same forming method as that of the gap AG11.

Figure 9:
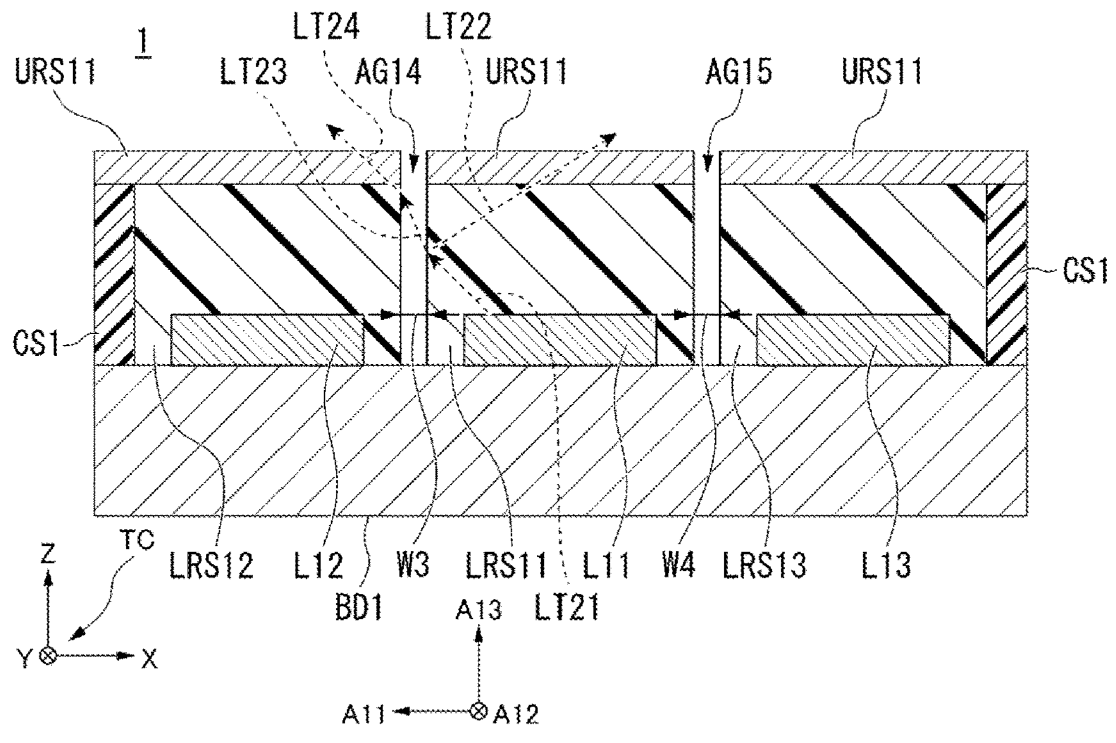
FIG. 9 is a cross-sectional view of the detection device 1 shown in FIG. 8.

In the first light emitted from the first light emitting unit L11, at least some of the first light passing through the first light emitting side optical member LRS11 and incident on the second light emitting side optical member LRS12 is reflected at each of an interface between the first light emitting side optical member LRS11 and the gap AG14 and an interface between the second light emitting side optical member LRS12 and the gap AG14. As shown in FIG. 9, the first light reflected in this way passes through the coat member URS11 and exits to the outside of the detection device 1. FIG. 9 is a cross-sectional view of the detection device 1 shown in FIG. 8. However, the cross-sectional view shown in FIG. 9 is a cross-sectional view of the detection device 1 along a virtual plane orthogonal to the second direction A12 so that each of the first light emitting unit L11, the second light emitting unit L12, and the third light emitting unit L13 can be seen when viewed in the second direction A12.

For example, the first light emitted from the first light emitting unit L11 in the direction indicated by arrow LT21 shown in FIG. 9 is an example of the first light emitted from the first light emitting unit L11 toward the second light emitting side optical member LRS12. At least some of the first light emitted from the first light emitting unit L11 in the direction indicated by arrow LT21 is reflected at the interface between the first light emitting side optical member LRS11 and the gap AG14 and travels in the direction indicated by arrow LT22. In this case, since the first light is incident on the first surface M11 at an angle equal to or greater than the first angle, it is transmitted through the coat member URS11 provided in the detection device 1. As a result, the first light exits to the outside of the detection device 1. Thus, the detection device 1 can increase an amount of a component of the first light traveling upward from the first light emitting side optical member LRS11. In other words, the detection device 1 can increase the amount of the first light received by the first light receiving unit R11.

Also, as shown in FIG. 8, a space between the first light emitting side optical member LRS11 and the third light emitting side optical member LRS13 in the first opening H11 included in the detection device 1 is a gap AG15. In other words, in the first opening H11, the gap AG15 is formed between the first light emitting side optical member LRS11 and the third light emitting side optical member LRS13. In other words, in the first opening H11, there is the gap AG15 formed between the first light emitting side optical member LRS11 and the third light emitting side optical member LRS13. Thus, as compared with the case in which a resin, a metal, or the like is disposed instead of the gap AG15, the detection device 1 can reduce its size in the first direction A11 by bringing the first light emitting unit L11 and the third light emitting unit L13 closer to each other. Also, the gap AG15 can be formed by, for example, the same forming method as that of the gap AG11.

In the first light emitted from the first light emitting unit L11, at least some of the first light passing through the first light emitting side optical member LRS11 and incident on the third light emitting side optical member LRS13 is reflected at each of an interface between the first light emitting side optical member LRS11 and the gap AG15 and an interface between the third light emitting side optical member LRS13 and the gap AG15. Similarly to the first light emitted in the direction indicated by arrow LT21, the first light reflected in this way passes through the coat member URS11 and exits to the outside of the detection device 1. Thus, the detection device 1 can increase the amount of the component of the first light traveling upward from the first light emitting side optical member LRS11. As a result, the detection device 1 can increase the amount of the first light received by the first light receiving unit R11.

Further, a width W3 shown in FIG. 9 is an example of a width of the gap AG14 in the first direction A11. Also, a width W4 shown in FIG. 9 is an example of a width of the gap AG15 in the first direction A11. The width W4 may be the same length as the width W3 or may be different from the width W3. In the following description, as an example, a case in which the width W4 is the same length as the width W3 will be described.

Here, an amount of the component that becomes stray light in the first light emitted from the first light emitting unit L11 increases as the width of the gap AG14 in the first direction A11 decreases. In other words, the amount of the component that becomes stray light in the first light emitted from the first light emitting unit L11 decreases as the width of the gap AG14 in the first direction A11 increases. This also applies to the gap AG15. That is, the amount of the component that becomes stray light in the first light emitted from the first light emitting unit L11 decreases as the width of the gap AG15 in the first direction A11 increases.

For example, there is a high possibility that some of the first light emitted from the first light emitting unit L11 in the direction indicated by arrow LT21 shown in FIG. 9 may not be received by the first light receiving unit R11 even when some of the first light is reflected in the skin of the person. This is because some of the first light emitted from the first light emitting unit L11 in the direction indicated by arrow LT21 shown in FIG. 9 is not reflected in the gap AG14, but is transmitted toward the second light emitting side optical member LRS12. That is, some of the first light emitted from the first light emitting unit L11 in the direction indicated by arrow LT21 is an example of the component that becomes stray light in the first light emitted from the first light emitting unit L11. In the example shown in FIG. 9, the first light transmitted in this way travels, for example, in the direction indicated by arrow LT23 and is incident on the second light emitting side optical member LRS12. After that, the first light incident on the second light emitting side optical member LRS12 travels, for example, in the direction indicated by arrow LT24, passes through the coat member URS11 provided at the upper surface of the second light emitting side optical member LRS12, and exits to the outside of the detection device 1. As an angle between the first light traveling toward the outside of the detection device 1 and the substrate BD1 decreases, the first light is more likely to be reflected in a direction different from the direction toward the first light receiving unit R11.

Figure 10:
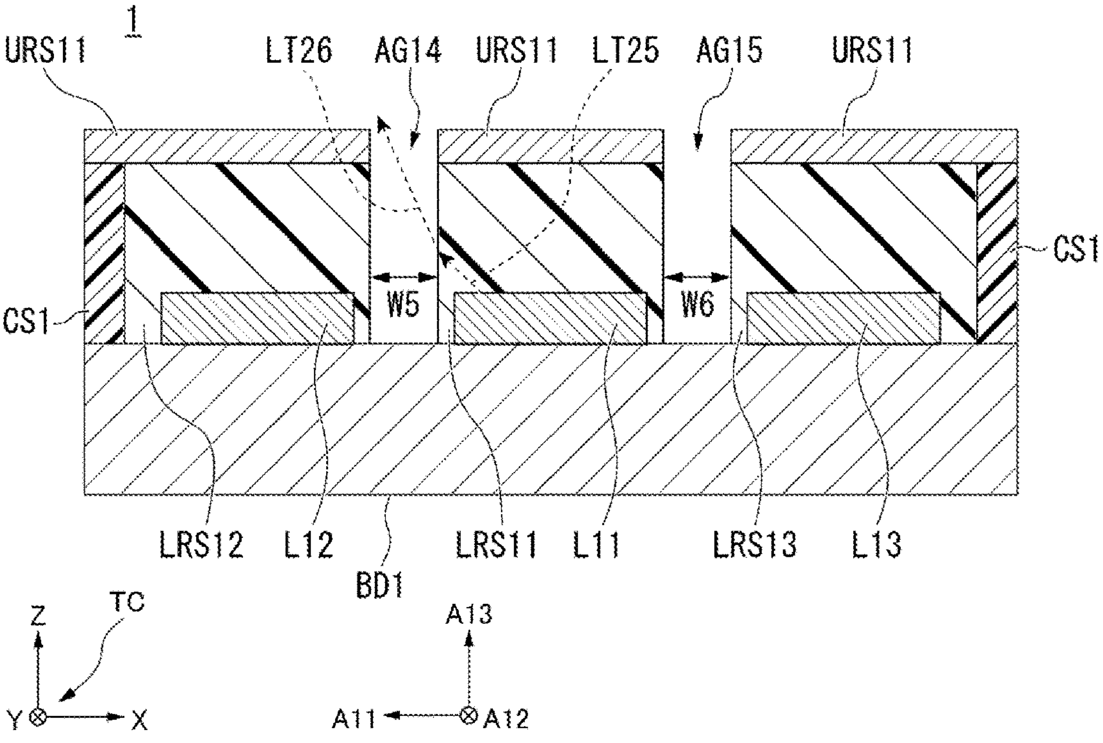
FIG. 10 is a cross-sectional view showing another example of the detection device 1 shown in FIG. 8.

Thus, as shown in FIG. 10, by setting the width of the gap AG14 in the first direction A11 to a width W5 that is longer than the width W3, the detection device 1 can increase the amount of the first light received by the first light receiving unit R11. Similarly, as shown in FIG. 10, by setting the width of the gap AG15 in the first direction A11 to a width W6 that is longer than the width W4, the detection device 1 can increase the amount of the first light received by the first light receiving unit R11.

FIG. 10 is a cross-sectional view showing another example of the detection device 1 shown in FIG. 8. However, the cross-sectional view shown in FIG. 10 is a cross-sectional view of the detection device 1 along a virtual plane orthogonal to the second direction A12 so that each of the first light emitting unit L11, the second light emitting unit L12, and the third light emitting unit L13 can be seen when viewed in the second direction A12. The width W5 shown in FIG. 10 is an example of the width of the gap AG14 in the first direction A11 of the detection device 1 shown in FIG. 10. The width W6 shown in FIG. 10 is an example of the width of the gap AG15 in the first direction A11 of the detection device 1 shown in FIG. 10. Also, the width W6 may be the same length as the width W5, or may be different from the width W5. In the following description, as an example, a case in which the width W6 is the same length as the width W5 will be described.

The width W5 is a width longer than the width W3 shown in FIG. 9. This can be realized, for example, by shortening a distance between the first light emitting unit L11 and an end portion on a side closer to the second light emitting unit L12 among end portions of the first light emitting side optical member LRS11 when viewed in the second direction A12. In addition, this can be realized, for example, by shortening the distance between the second light emitting unit L12 and an end portion on a side closer to the first light emitting unit L11 among end portions of the second light emitting side optical member LRS12 when viewed in the second direction A12. In the example shown in FIG. 10, by shortening both of these two distances as compared with the example shown in FIG. 9, the width of the gap AG14 in the first direction A11 can be set to the width W5 longer than the width W3. In this case, the amount of the component that becomes stray light in the first light emitted from the first light emitting unit L11 is reduced. This is because some of the first light emitted from the first light emitting unit L11 in the direction indicated by arrow LT25 shown in FIG. 10 is transmitted through the gap AG14 without being reflected, passes through the gap AG14, and exits to the outside of the detection device 1. Here, the direction indicated by arrow LT25 is the same as the direction indicated by arrow LT21 shown in FIG. 9.

For example, some of the first light emitted from the first light emitting unit L11 in the direction indicated by arrow LT25 is not reflected by the gap AG14, but travels in the direction indicated by arrow LT26, passes through the gap AG14, and exits to the outside of the detection device 1. An angle between the first light traveling in the direction indicated by arrow LT26 and the substrate BD1 is greater than an angle between the first light traveling in the direction indicated by arrow LT24 shown in FIG. 9 and the substrate BD1. For this reason, the first light traveling in the direction indicated by arrow LT26 is more likely to be reflected in the direction toward the first light receiving unit R11 than the first light traveling in the direction indicated by arrow LT24 shown in FIG. 9. That is, as the width of the gap AG14 in the first direction A11 increases, the detection device 1 can reduce the amount of the component that becomes stray light in the first light emitted from the first light emitting unit L11. This also applies to the gap AG15. That is, as the width of the gap AG15 in the first direction A11 increases, the detection device 1 can reduce the amount of the component that becomes stray light in the first light emitted from the first light emitting unit L11.

As described above, there is a motivation to increase each width of the gap AG14 and the gap AG15 in the first direction A11 for reducing the amount of the component that becomes stray light in the first light emitted from the first light emitting unit L11. On the other hand, from the motive of reducing a size of the detection device 1 in the second direction A12, a width of the gap AG12 between the first light receiving side optical member RRS11 and the second light receiving side optical member RRS12 in the second direction A12 is desirably narrower. From this, by making each width of the gap AG14 and the gap AG15 in the first direction A11 greater than the width of the gap AG12 in the second direction A12, the detection device 1 can reduce the amount of the component that becomes stray light in the first light emitted from the first light emitting unit L11 while inhibiting an increase in the size in the second direction A12.

Figure 11:
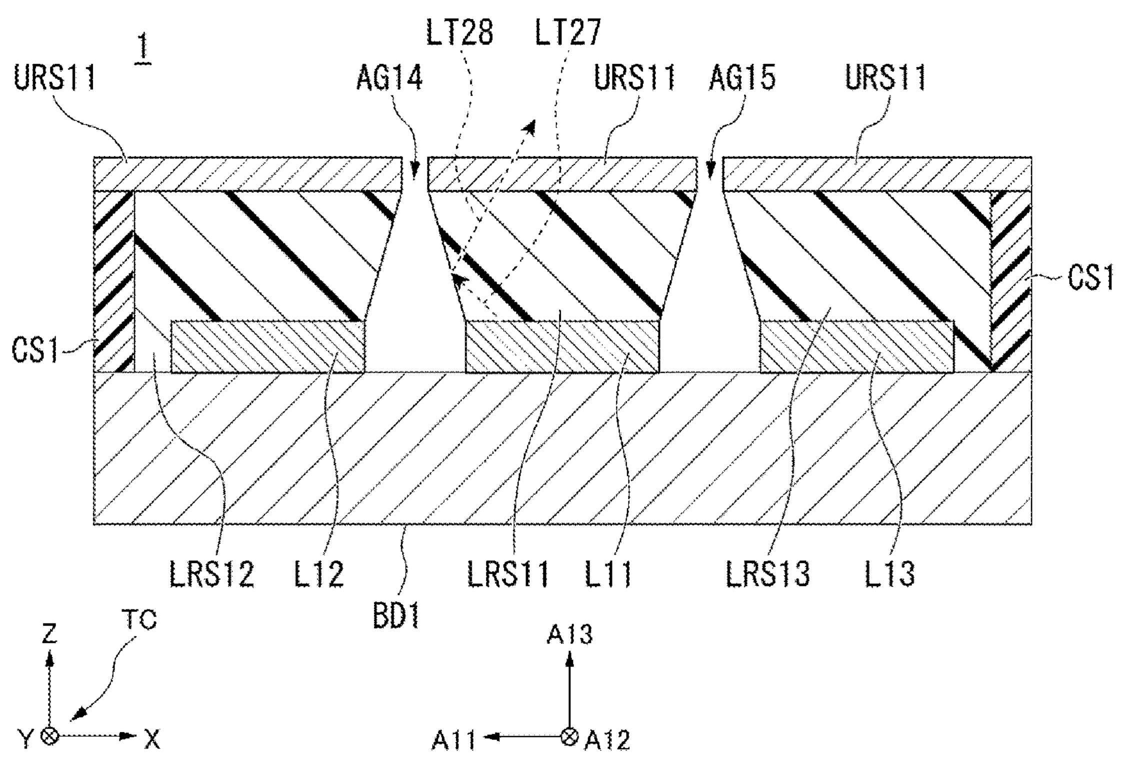
FIG. 11 is a cross-sectional view showing an example of the detection device 1 when shapes of both a gap AG14 and a gap AG15 are trapezoidal.

In addition, as shown in FIG. 11, the amount of the component that becomes stray light in the first light emitted from the first light emitting unit L11 can be further reduced by making a shape of at least one of the gap AG14 and the gap AG15 trapezoidal when viewed in the second direction A12. FIG. 11 is a cross-sectional view showing an example of the detection device 1 when shapes of both the gap AG14 and the gap AG15 are trapezoidal. However, the cross-sectional view shown in FIG. 11 is a cross-sectional view of the detection device 1 along a virtual plane orthogonal to the second direction A12 so that each of the first light emitting unit L11, the second light emitting unit L12, and the third light emitting unit L13 can be seen when viewed in the second direction A12. In the example shown in FIG. 11, the shape of the gap AG14 when viewed in the second direction A12 is a trapezoid whose width becomes narrower from the lowermost portion to the upper most portion. In this case, some of the first light emitted from the first light emitting unit L11 in the direction indicated by arrow LT27 shown in FIG. 11 is reflected by the gap AG14 and travels substantially directly above the first light emitting unit L11.

In the example shown in FIG. 11, the first light reflected in this way travels, for example, in the direction indicated by arrow LT28, passes through the coat member URS11, and exits to the outside of the detection device 1. In addition, an angle between arrow LT28 and the direction of gravity decreases as an angle between a wall surface on the positive direction side of the X axis among wall surfaces forming the gap AG14 and the direction of gravity increases when viewed in the second direction A12. That is, in the detection device 1, the angle between the direction of gravity and the wall surface on the positive direction side of the X axis among the wall surfaces forming the gap AG14 is increased when viewed in the second direction A12, and thus the first light reflected by the wall surface is likely to travel substantially directly above the first light emitting unit L11. This means that the first light is more likely to travel toward the first light receiving unit R11 after being reflected in the skin of the person. That is, by making the shape of the gap AG14 trapezoidal when viewed in the second direction A12, the detection device 1 can more reliably reduce the amount of the component that becomes stray light in the first light emitted from the first light emitting unit L11. This situation also applies to the gap AG15.

As described above, the detection device 1 according to the first embodiment includes the substrate BD1, the first light emitting unit L11, the first light receiving unit R11, the first light emitting side optical member LRS11, the first light receiving side optical member RRS11, and the accommodating member CS1. The first light emitting unit L11 emits the first light and is provided at the substrate BD1. The first light receiving unit R11 receives the first light and is provided at the substrate BD1 side by side with the first light emitting unit L11 in the second direction A12 when viewed in the first direction A11 parallel to the substrate BD1. Here, the second direction A12 is a direction parallel to the substrate BD1 and orthogonal to the first direction A11. The first light emitting side optical member LRS11 transmits the first light and covers the first light emitting unit L11 at the substrate BD1. The first light receiving side optical member RRS11 transmits the first light and covers the first light receiving unit R11 at the substrate BD1. The accommodating member CS1 is provided at the substrate BD1, and the first opening L11 in which the first light emitting unit L11, the first light emitting side optical member LRS11, the first light receiving unit R11, and the first light receiving side optical member RRS11 are accommodated is formed therein. In addition, in the second direction, at least a part between the first light emitting side optical member LRS11 and the first light receiving side optical member RRS11 is the gap AG11. Thus, as compared with the case in which a resin, a metal, or the like is disposed instead of the gap AG11, the detection device 1 can increase the amount of light received by the first light receiving unit R11 by bringing the first light emitting unit L11 and the first light receiving unit R11 closer together and can also reduce the size in the second direction A12. That is, the detection device 1 can achieve reduction in size while inhibiting a decrease in the amount of light received by the first light receiving unit R11.

Second Embodiment

A second embodiment will be described below with reference to the drawings.

Overview of Detection Device of Second Embodiment

First, an overview of a detection device according to the second embodiment will be described.

The detection device according to the second embodiment includes a substrate, a first light emitting unit, a first light receiving unit, a first optical member, a second optical member, and an accommodating member. The first light emitting unit emits first light and is provided at the substrate. The first light receiving unit receives the first light and is provided at the substrate side by side with the first light emitting unit in a second direction when viewed in a first direction parallel to the substrate. Here, the second direction is parallel to the substrate and orthogonal to the first direction. The first optical member transmits the first light and covers the first light emitting unit at the substrate. The second optical member transmits the first light and covers the first light receiving unit at the substrate. The accommodating member is provided at the substrate, and a first opening in which the first light emitting unit and the first optical member are accommodated and a second opening in which the first light receiving unit and the second optical member are accommodated are formed therein. In addition, at least one of the first optical member and the second optical member protrudes from an opening formed in the accommodating member in a third direction intersecting the first direction and the second direction.

Thus, the detection device can increase an amount of light received by the first light receiving unit by improving adhesion between itself and the skin of a person and can reduce its size in the third direction as compared with a case in which a lens for condensing the first light emitted from the first light emitting unit, a lens for condensing reflected light of the first light toward the first light receiving unit, a member for attaching these lenses to the detection device 1, and the like are provided. That is, the detection device can achieve reduction in size while inhibiting a decrease in the amount of light received by the light receiving unit.

In the following description, a configuration of the detection device according to the second embodiment will be described in detail.

Configuration of Detection Device of Second Embodiment

The configuration of the detection device according to the second embodiment will be described below using a detection device 2 as an example. In the following description, for convenience of description, a user of the detection device 2 will be described as a second user. In addition, in the second embodiment, for convenience of description, when the detection device 2 is viewed while facing in a certain direction, it will be described as the detection device 2 being viewed in that direction. Also, the configuration of the detection device 2 according to the second embodiment may be combined with the configuration of the detection device 1 according to the first embodiment in any manner.

Figure 12:
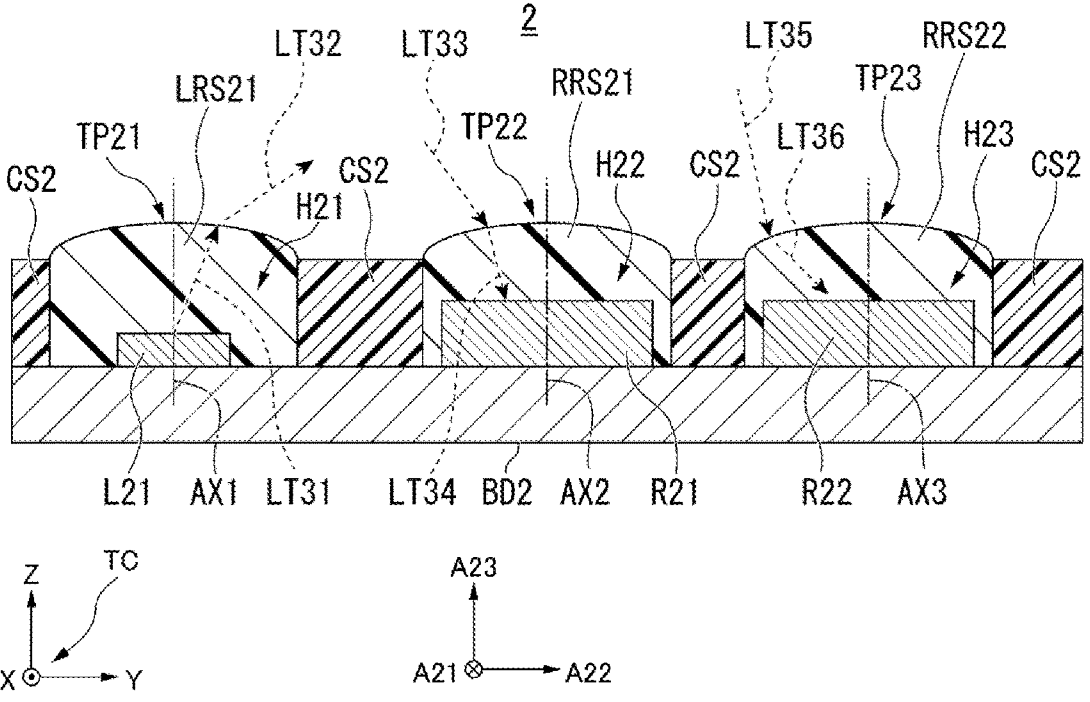
FIG. 12 is a cross-sectional view showing a first configuration example of a detection device 2.
Figure 13:
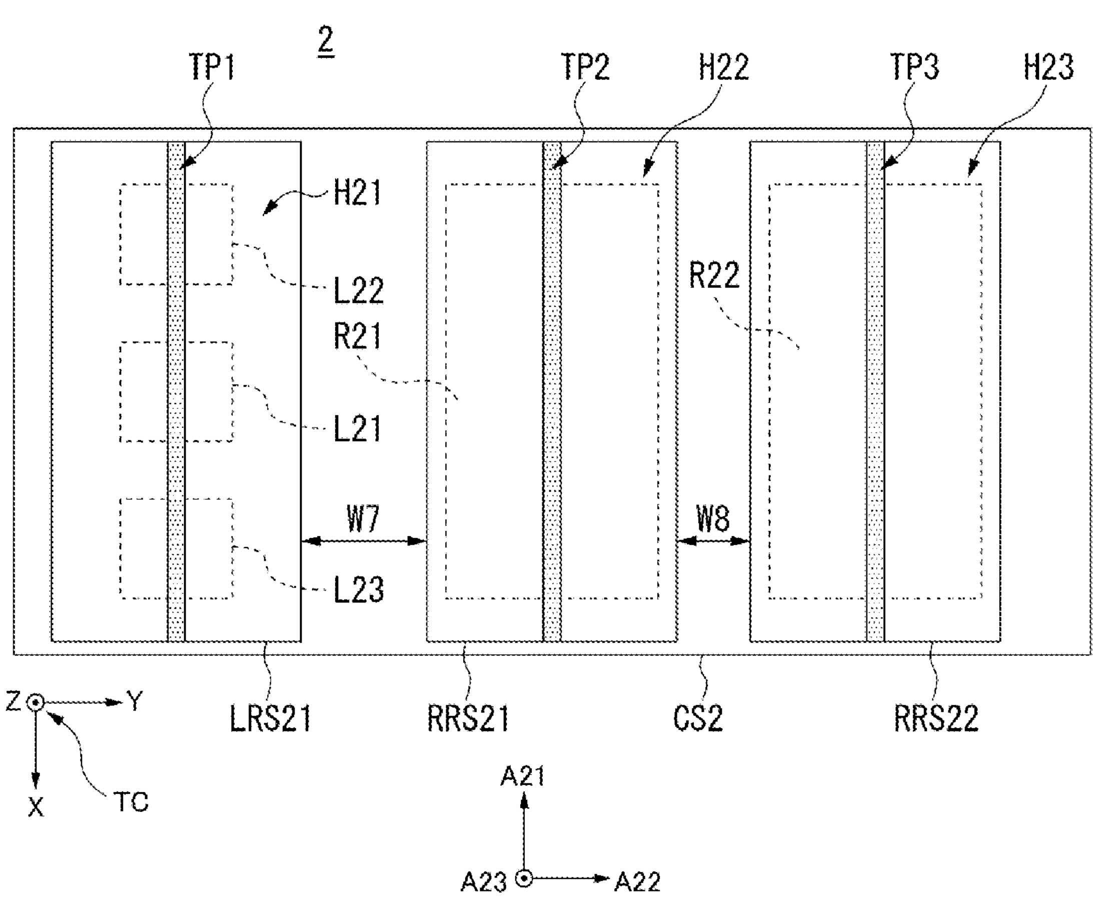
FIG. 13 is a top view of the detection device 2 shown in FIG. 12.

FIG. 12 is a cross-sectional view showing a first configuration example of the detection device 2. Also, FIG. 13 is a top view of the detection device 2 shown in FIG. 12.

The detection device 2 is a device that detects biological information using a non-invasive method. In the following description, as an example, a case in which the detection device 2 is a device that detects biological information of a person will be described. In this case, the detection device 2 detects a pulse wave, a pulse, oxygen saturation, and the like as the biological information and is provided, for example, in vital equipment such as a smart watch, an active tracker, a smart ring, or the like. Also, the detection device 2 may be configured to detect biological information of an animal other than a human or may be configured to detect biological information of a plant.

Specifically, the detection device 2 is pressed against the skin of the person and emits light in a predetermined wavelength band toward the skin. Then, the detection device 2 receives reflected light of the light emitted toward the skin and detects a pulse, oxygen saturation, and the like based on a change over time in an amount of received light of the reflected light. Here, a substance that reflects the light emitted by the detection device 2 is, for example, hemoglobin or the like in capillary blood vessels, but is not limited thereto. For example, the detection device 2 uses green light in the case of detecting a pulse of a person. For example, the detection device 2 uses red light, infrared light, or the like in the case of detecting oxygen saturation of a person.

The detection device 2 includes, for example, a substrate BD2, a first light emitting unit L21, a second light emitting unit L22, a third light emitting unit L23, a first light receiving unit R21, a second light receiving unit R22, a first light emitting side optical member LRS21, a first light receiving side optical member RRS21, a second light receiving side optical member RRS22, and an accommodating member CS2. In addition, the detection device 2 also includes other members such as a processor that acquires data indicating an amount of light received by the first light receiving unit R11 and performs various types of processing based on the acquired data. The various types of processing include, for example, processing of calculating a pulse, oxygen saturation, and the like based on a change over time in the amount of received light indicated by the data. However, in the present disclosure, descriptions of these other members will be omitted. For this reason, these other members will also be omitted in each figure.

Further, the detection device 2 may not include one or both of the second light emitting unit L22 and the third light emitting unit L23. Here, when the detection device 2 does not include both the second light emitting unit L22 and the third light emitting unit L23, the detection device 2 does not include both the second light receiving unit R22 and the second light receiving side optical member RRS22. Also, the detection device 2 may not include both the first light receiving unit R21 and the first light receiving side optical member RRS21 but may include both the second light receiving unit R22 and the second light receiving side optical member RRS22. Also, the detection device 2 may not include both the second light receiving unit R22 and the second light receiving side optical member RRS22, but may include both the first light receiving unit R21 and the first light receiving side optical member RRS21.

The substrate BD2 may be any substrate as long as it can be used for a substrate of the detection device 2. The substrate BD2 is provided with the first light emitting unit L21, the second light emitting unit L22, the third light emitting unit L23, the first light receiving unit R21, the second light receiving unit R22, the first light emitting side optical member LRS21, the first light receiving side optical member RRS21, the second light receiving side optical member RRS22, and the accommodating member CS2. In the following description, for convenience of description, a surface of two surfaces of the substrate BD2 on the positive direction side of the Z axis in each figure will be described as an upper surface of the substrate BD2, and a surface thereof on the negative direction side of the Z axis in each figure will be described as a lower surface of the substrate BD2. Also, in the following description, as an example, a case in which the substrate BD2 is provided with the first light emitting unit L21, the second light emitting unit L22, the third light emitting unit L23, the first light receiving unit R21, the second light receiving unit R22, the first light emitting side optical member LRS21, the first light receiving side optical member RRS21, the second light receiving side optical member RRS22, and the accommodating member CS2 at the upper surface of the substrate BD2.

A configuration of the first light emitting unit L21 is similar to the configuration of the first light emitting unit L11 according to the first embodiment. For this reason, in the second embodiment, a detailed description of the configuration of the first light emitting unit L21 will be omitted. However, also in the second embodiment, a case in which a first wavelength band is a green wavelength band will be described as an example. In this case, the first light emitting unit L21 emits green light as the first light. The first light emitting unit L21 is an example of the first light emitting unit.

A configuration of the second light emitting unit L22 is similar to the configuration of the second light emitting unit L12 according to the first embodiment. For this reason, in the second embodiment, a detailed description of the configuration of the second light emitting unit L22 will be omitted. The second light emitting unit L22 is provided at the upper surface of the substrate BD2 side by side with the first light emitting unit L21 in a predetermined first direction A21 with respect to the substrate BD2. Here, the first direction A21 may be any direction as long as it is a direction parallel to the substrate BD2. In each figure used to describe the second embodiment, as an example, a state in which the first direction A21 coincides with the negative direction of the X axis is shown. In addition, in the example shown in FIGS. 12 and 13, the second light emitting unit L22 is provided to be adjacent to the first light emitting unit L21 in the first direction A21. The second light emitting unit L22 is an example of a second light emitting unit.

A configuration of the third light emitting unit L23 is similar to the configuration of the third light emitting unit L13 according to the first embodiment. For this reason, in the second embodiment, a detailed description of the configuration of the third light emitting unit L23 will be omitted. The second light emitting unit L22 is provided at the upper surface of the substrate BD2 side by side with the first light emitting unit L21 in the first direction A21. In the example shown in FIGS. 12 and 13, the second light emitting unit L22 is provided to be adjacent to the first light emitting unit L21 in a direction opposite to the first direction A21. That is, in the example, the first light emitting unit L21 is provided between the second light emitting unit L22 and the third light emitting unit L23 in the first direction A21. The third light emitting unit L23 is an example of the second light emitting unit.

Further, in the second embodiment, in order to simplify the description, a case in which the first to the third light emitting units L21 to L23 have the same shape and the first to the third light emitting units L21 to L23 overlap one another when viewed in the first direction A21 will be described.

A configuration of the first light receiving unit R21 is similar to the configuration of the first light receiving unit R11 according to the first embodiment. For this reason, in the second embodiment, a detailed description of the configuration of the first light receiving unit R21 will be omitted. When viewed in the first direction A21, the first light receiving unit R21 is provided at the upper surface of the substrate BD2 side by side with the first light emitting unit L21 in a second direction A22. The second direction A22 is a direction parallel to the substrate BD2 and orthogonal to the first direction A21. In each figure used to describe the second embodiment, as an example, a state in which the second direction A22 coincides with the positive direction of the Y axis is shown. For this reason, the cross-sectional view shown in FIG. 12 is a cross-sectional view of the detection device 2 along a virtual plane orthogonal to the first direction A21 so that the first light emitting unit L21, the first light receiving unit R21, and the second light receiving unit R22 can be seen when viewed in the first direction A21. Also, in the second embodiment, in each figure, in order to prevent the figures from becoming complicated, members for coupling a transmission path at the substrate BD2 to the first light receiving unit R21 are omitted. Here, the members are, for example, wire bonding, coupling terminals, and the like, but are not limited thereto. The first light receiving unit R21 is an example of the first light receiving unit.

A configuration of the second light receiving unit R22 is similar to the configuration of the second light receiving unit R12 according to the first embodiment. For this reason, in the second embodiment, a detailed description of the configuration of the second light receiving unit R22 will be omitted. When viewed in the first direction A21, the second light receiving unit R22 is provided at the upper surface of the substrate BD2 side by side with the first light receiving unit R21 in the second direction A22. In the example shown in FIGS. 12 and 13, the second light receiving unit R22 is provided to be adjacent to the first light receiving unit R21 in the second direction A22. That is, in the example, the first light receiving unit R21 is interposed between the first light emitting unit L21 and the second light receiving unit R22 in the second direction A22. Also, in the second embodiment, in each figure, in order to prevent the figures from becoming complicated, members for coupling the transmission path at the substrate BD2 to the second light receiving unit R22 are omitted. Here, the members are, for example, wire bonding, coupling terminals, and the like, but are not limited thereto. The second light receiving unit R22 is an example of a second light receiving unit.

The first light emitting side optical member LRS21 transmits each of the first light, a second light, and a third light. Also, the first light emitting side optical member LRS21 may be configured to transmit each of the first light, the second light, and the third light and transmit light in a wavelength band different from each of a first wavelength band, a second wavelength band, and a third wavelength band, or may be configured to transmit each of the first light, the second light, and the third light and not to transmit light in a wavelength band different from each of the first wavelength band, the second wavelength band, and the third wavelength band. In the first embodiment, as an example, a case in which the first light emitting side optical member LRS21 transmits each of the first light, the second light, and the third light, and transmits light in a wavelength band different from each of the first wavelength band, the second wavelength band, and the third wavelength band will be described. The first light emitting side optical member LRS21 is made of, for example, a resin that transmits light, such as a transparent epoxy resin or a transparent acrylic resin, but is not limited thereto. In the second embodiment, as an example, a case in which the resin forming the first light emitting side optical member LRS21 is the same resin as the resin forming the first light emitting side optical member LRS11 described in the first embodiment will be described.

The first light emitting side optical member LRS21 covers all of the first light emitting unit L21, the second light emitting unit L22, and the third light emitting unit L23 at the substrate BD2. In other words, the first light emitting side optical member LRS21 and the substrate BD2 surround and enclose three light emitting units of the first light emitting unit L21, the second light emitting unit L22, and the third light emitting unit L23. In the second embodiment, as an example, a case in which the first light emitting side optical member LRS21 is provided at the upper surface of the substrate BD2 so that no gap is generated between the first light emitting side optical member LRS21 and the three light emitting units will be described. In this case, there is no gap between the first light emitting side optical member LRS21 and the three light emitting units except for a gap unintentionally formed in a manufacturing process.

Thus, the detection device 2 can inhibit refraction of the light emitted from the three light emitting units between the first light emitting side optical member LRS21 and the substrate BD2. As a result, an optical design of the detection device 2 can be simplified. In addition, since the three light emitting units are covered with the first light emitting side optical member LRS21, the detection device 2 can inhibit erroneous touching of the second user at the three light emitting units and exposure of the three light emitting units to dust, water, or the like. As a result, the detection device 2 can inhibit occurrence of problems in the three light emitting units. Also, the detection device 2 may have a configuration in which a gap is formed in a part of a space between the first light emitting side optical member LRS21 and the three light emitting units. The first light emitting side optical member LRS21 is an example of the first optical member.

The first light receiving side optical member RRS21 transmits the first light. Also, the first light receiving side optical member RRS11 may be configured to transmit the first light and transmit light in a wavelength band different from the first wavelength band, or may be configured to transmit the first light and not to transmit light in a wavelength band different from the first wavelength band. In the second embodiment, as an example, a case in which the first light receiving side optical member RRS21 transmits the first light and transmits light in a wavelength band different from the first wavelength band will be described. The first light receiving side optical member RRS11 is made of a material that has a refractive index of about 1.4 or more and transmits the first light, for example, a resin that transmits light, such as a transparent epoxy resin or a transparent acrylic resin, but is not limited thereto. In the second embodiment, as an example, a case in which the resin forming the first light receiving side optical member RRS21 is the same resin as the resin forming the first light emitting side optical member LRS11 described in the first embodiment will be described.

The first light receiving side optical member RRS21 covers the first light receiving unit R21 at the substrate BD2. In other words, the first light receiving side optical member RRS21 and the substrate BD2 surround and enclose the first light receiving unit R21. In the second embodiment, as an example, a case in which the first light receiving side optical member RRS21 is provided at the upper surface of the substrate BD2 so that no gap is generated between the first light receiving side optical member RRS21 and the first light receiving unit R21 will be described.

In this case, there is no gap between the first light receiving side optical member RRS21 and the first light receiving unit R21 except for a gap unintentionally formed in the manufacturing process. Thus, the detection device 2 can inhibit refraction of the first light incident on the first light receiving side optical member RRS21 between the first light receiving side optical member RRS21 and the substrate BD2. As a result, the optical design of the detection device 2 can be simplified. In addition, since the first light receiving unit R21 is covered with the first light receiving side optical member RRS21, the detection device 2 can inhibit erroneous touching of the second user at the first light receiving unit R21 and exposure of the first light receiving unit R21 to dust, water, or the like. As a result, the detection device 2 can inhibit occurrence of problems in the first light receiving unit R21. Also, the detection device 2 may have a configuration in which a gap is formed in a part of a space between the first light receiving side optical member RRS21 and the first light receiving unit R21.

Further, in the detection device 2, a length of the first light receiving side optical member RRS21 in the first direction A21 may be the same as the length of the first light emitting side optical member LRS21 in the first direction A21, or may be different from the length of the first light emitting side optical member LRS21 in the first direction A21. The first light receiving side optical member RRS21 is an example of the second optical member.

The second light receiving side optical member RRS22 transmits each of the second light and the third light. Also, the second light receiving side optical member RRS22 may be configured to transmit each of the second light and the third light and transmit light in a wavelength band different from each of the second wavelength band and the third wavelength band, or may be configured to transmit each of the second light and the third light and not to transmit light in a wavelength band different from each of the second wavelength band and the third wavelength band. In the second embodiment, as an example, a case in which the second light receiving side optical member RRS22 transmits each of the second light and the third light and transmits light in a wavelength band different from each of the second wavelength band and the third wavelength band will be described. The second light receiving side optical member RRS22 is made of a material that has a refractive index of about 1.4 or more and transmits each of the second light and the third light, for example, a resin that transmits light, such as a transparent epoxy resin or a transparent acrylic resin, but is not limited thereto. In the second embodiment, as an example, a case in which the resin forming the second light receiving side optical member RRS22 is the same resin as the resin forming the first light emitting side optical member LRS11 described in the first embodiment will be described.

The second light receiving side optical member RRS22 covers the second light receiving unit R22 at the substrate BD2. In other words, the second light receiving side optical member RRS22 and the substrate BD2 surround and enclose the second light receiving unit R22. In the following description, as an example, a case in which the second light receiving side optical member RRS22 is provided at the upper surface of the substrate BD2 so that no gap is generated between the second light receiving side optical member RRS22 and the second light receiving unit R22 will be described. In this case, there is no gap between the second light receiving side optical member RRS22 and the second light receiving unit R22 except for a gap unintentionally formed in the manufacturing process. Thus, the detection device 2 can inhibit refraction of each of the second light and the third light incident on the second light receiving side optical member RRS22 between the second light receiving side optical member RRS22 and the substrate BD2. As a result, the optical design of the detection device 2 can be simplified. In addition, since the second light receiving unit R22 is covered with the second light receiving side optical member RRS22, the detection device 2 can inhibit erroneous touching of the second user at the second light receiving unit R22 and exposure of the second light receiving unit R22 to dust, water, or the like. As a result, the detection device 2 can inhibit occurrence of problems in the second light receiving unit R22. Also, the detection device 2 may have a configuration in which a gap is formed in a part of the space between the second light receiving side optical member RRS22 and the second light receiving unit R22.

Further, in the detection device 2, a length of the second light receiving side optical member RRS22 in the first direction A21 may be the same as the length of the first light emitting side optical member LRS21 in the first direction A21, or may be different from the length of the first light emitting side optical member LRS21 in the first direction A21. The second light receiving side optical member RRS22 is an example of a fourth optical member.

The accommodating member CS2 is provided at the upper surface of the substrate BD2. The accommodating member CS2 is a member that forms an outer shape of the detection device 2 together with the substrate BD2. In the following description, in order to simplify the description, as an example, a case in which an outer shape of the accommodating member CS2 is a rectangular parallelepiped shape as a whole except for various openings formed in the accommodating member CS2, distortions due to manufacturing errors, and the like will be described. In this case, an upper surface of the accommodating member CS2 is a surface parallel to the substrate BD2. Also, the upper surface of the accommodating member CS2 may be a surface that is not parallel to the substrate BD2. Further, a height of the upper surface of the accommodating member CS2 from the substrate BD2 is determined to be higher than a height of any of the first light emitting unit L21, the second light emitting unit L22, and the third light emitting unit L23 from the substrate BD1.

The accommodating member CS2 is made of, for example, an opaque resin with a high light reflectance, a transparent resin mixed with metal powder, a metal, or the like. In the second embodiment, as an example, a case in which the accommodating member CS2 is made of a white resin will be described.

Here, a first opening H21, a second opening H22, and a third opening H23 are formed in the accommodating member CS2.

Each of the first to the third openings H21 to H23 is a hole that penetrates the accommodating member CS2 in a third direction A23 intersecting the first direction A21 and the second direction A22. In the following description, as an example, a case in which the third direction A23 is a direction from the substrate BD2 toward the first light emitting unit L21 among two directions orthogonal to both the first direction A21 and the second direction A22 will be described. In this case, the third direction A23 is orthogonal to the first direction A21 and the second direction A22, and coincides with the positive direction of the Z axis in each figure used to describe the second embodiment. Also, in this case, the upper surface of the accommodating member CS2 is orthogonal to the third direction A23.

The first opening H21 is a hole in which the first light emitting unit L21, the second light emitting unit L22, the third light emitting unit L23, and the first light emitting side optical member LRS21 are accommodated at the upper surface of the substrate BD2. In the example shown in FIGS.

12 and 13, a shape of a contour of the first opening H21 is a rectangular shape when viewed in the first direction A21. Further, in the example, the shape of the contour of the first opening H21 is a rectangular shape when viewed in the third direction A23. That is, the shape of the first opening H21 is a rectangular parallelepiped shape. Also, instead of the rectangular parallelepiped shape, the shape of the first opening H21 may be another shape that can accommodate the first light emitting unit L21, the second light emitting unit L22, the third light emitting unit L23, and the first light emitting side optical member LRS21 at the upper surface of the substrate BD2. The other shape is, for example, a trapezoid, but is not limited thereto.

The second opening H22 is a hole in which the first light receiving unit R21 and the first light receiving side optical member RRS21 are accommodated at the upper surface of the substrate BD2. In the example shown in FIGS. 12 and 13, a shape of a contour of the second opening H22 is a rectangular shape when viewed in the first direction A21. Further, in the example, the shape of the contour of the second opening H22 is a rectangular shape when viewed in the third direction A23. That is, the shape of the second opening H22 is a rectangular parallelepiped shape. Also, instead of the rectangular parallelepiped shape, the shape of the second opening H22 may be another shape that can accommodate the first light receiving unit R21 and the first light receiving side optical member RRS21 at the upper surface of the substrate BD2. The other shape is, for example, a trapezoid, but is not limited thereto. Further, as described above, in the detection device 2, the length of the first light receiving side optical member RRS21 in the first direction A21 may be the same as the length of the first light emitting side optical member LRS21 in the first direction A21, or may be different from the length of the first light emitting side optical member LRS21 in the first direction A21. For this reason, in the detection device 2, a length of the second opening H22 in the first direction A21 may be the same as the length of the first opening H21 in the first direction A21, or may be different from the length of the first opening H21 in the first direction A21.

The third opening H23 is a hole in which the second light receiving unit R22 and the second light receiving side optical member RRS22 are accommodated at the upper surface of the substrate BD2. In the example shown in FIGS. 12 and 13, a shape of a contour of the third opening H23 is a rectangular shape when viewed in the first direction A21. Further, in the example, the shape of the contour of the third opening H23 is a rectangular shape when viewed in the third direction A23. That is, the shape of the third opening H23 is a rectangular parallelepiped shape. Also, instead of the rectangular parallelepiped shape, the shape of the third opening H23 may be another shape that can accommodate the second light receiving unit R22 and the second light receiving side optical member RRS22 at the upper surface of the substrate BD2. The other shape is, for example, a trapezoid, but is not limited thereto. In addition, as described above, in the detection device 2, the length of the second light receiving side optical member RRS22 in the first direction A21 may be the same as the length of the first light emitting side optical member LRS21 in the first direction A21, or may be different from the length of the first light emitting side optical member LRS21 in the first direction A21. For this reason, in the detection device 2, a length of the third opening H23 in the first direction A21 may be the same as the length of the first opening H21 in the first direction A21, or may be different from the length of the first opening H21 in the first direction A21.

Here, each of the first light emitting side optical member LRS21, the first light receiving side optical member RRS21, and the second light receiving side optical member RRS22 protrudes in the third direction A23 from an opening formed in the accommodating member CS2.

More specifically, the first light emitting side optical member LRS21 protrudes in the third direction A23 from the first opening H21 formed in the accommodating member CS2. In addition, a surface of the first light emitting side optical member LRS21 in the third direction A23 includes a curved surface having a positive gradient in the third direction A23. In the second embodiment, for convenience of description, the surface of the first light emitting side optical member LRS21 in the third direction A23 will be described as an upper surface of the first light emitting side optical member LRS21.

In the example shown in FIGS. 12 and 13, when viewed in the first direction A21, the first light emitting side optical member LRS21 is divided into a first light emitting side non-protruding region that overlaps the accommodating member CS2 and a first light emitting side protruding region that does not overlap the accommodating member CS2. In addition, in that case, a shape of the first light emitting side non-protruding region is a rectangular shape. In other words, in that case, a shape of the region that overlaps the first opening H21 among regions included in the first light emitting side optical member LRS21 is a rectangular shape. That is, in the detection device 2, the first opening H21 is completely filled with the resin forming the first light emitting side optical member LRS21 except for a gap unintentionally formed in the manufacturing process. For this reason, a contour of a cross-section of the first light emitting side optical member LRS21 along a virtual plane including the upper surface of the accommodating member CS2 coincides with a shape of an inner edge of the first opening H21 when viewed in the third direction A23. Thus, the detection device 2 can inhibit refraction of the light in the first opening H21, and as a result, can inhibit generation of stray light.

On the other hand, in that case, the first light emitting side protruding region has an upwardly convex dome shape. Also, a shape of the first light emitting side optical member LRS21 is a rectangular shape when viewed in the third direction A23. Further, the upper surface of the first light emitting side optical member LRS21 has a portion having the highest height from the accommodating member CS2 in the third direction A23 as a first vertex portion TP1. In addition, a height of the upper surface of the first light emitting side optical member LRS21 from the substrate BD2 increases from an end portion of the upper surface toward the first vertex portion TP1. In the example shown in FIG. 12, the upper surface of the first light emitting side optical member LRS21 further has a gradient that gradually becomes gentler from the end portion of the upper surface toward the first vertex portion TP1. The first vertex portion TP1 may be a point-like portion, a linearly extending portion, a band-like extending portion, or a planarly extending portion.

In the example shown in FIGS. 12 and 13, the first vertex portion TP1 extends in a band shape in the first direction A21 to couple both ends of the first light emitting side optical member LRS21 in the first direction A21. In addition, in the example, when viewed in the first direction A21, the first vertex portion TP1 overlaps a first virtual line segment AX1 that passes through a center of a surface in the third direction A23 among surfaces included in the first light emitting unit L21 and extends in the third direction A23.

Such a first light emitting side optical member LRS21 can refract some of the light emitted from each of the first light emitting unit L21, the second light emitting unit L22, and the third light emitting unit L23 in a direction approaching the first light receiving unit R21 at the upper surface of the first light emitting side optical member LRS21. The direction approaching the first light receiving unit R21 may be rephrased as a direction closer to the second direction A22 than a traveling direction of the first light before refraction. For example, the first light emitted from the first light emitting unit L21 in the direction indicated by arrow LT31 shown in FIG. 12 is refracted at the upper surface of the first light emitting side optical member LRS21 and travels in the direction indicated by arrow LT32. The direction indicated by arrow LT32 is an example of a direction closer to the first light receiving unit R21 than the direction indicated by arrow LT31 and is an example of a direction closer to the second direction A22 than the traveling direction of the first light before refraction.

Thus, the detection device 2 can reflect the first light emitted from the first light emitting unit L21 in a skin part at a position close to the first light receiving unit R21 in the skin of the person. This also applies to each of the second light emitted from the second light emitting unit L22 and the third light emitted from the third light emitting unit L23. As a result, the detection device 2 can increase an amount of light received by the first light receiving unit R21 in the first light reflected in the skin of the person. In addition, the detection device 2 can increase an amount of light received by the second light receiving unit R22 in the second light and the third light reflected in the skin of the person. In addition, such an increase in the amount of received light leads to a decrease in an amount of a component that becomes stray light in the light emitted from each of the first light emitting unit L21, the second light emitting unit L22, and the third light emitting unit L23. As a result, the detection device 2 can reduce noise in detecting each of a pulse and oxygen saturation and can improve a S/N ratio in detecting these.

Also, the first light receiving side optical member RRS21 protrudes from the second opening H22 formed in the accommodating member CS2 in the third direction A23. In addition, the surface in the third direction A23 among the surfaces included in the first light receiving side optical member RRS21 includes a curved surface having a positive gradient in the third direction A23. In the second embodiment, for convenience of description, the surface in the third direction A23 among the surfaces included in the first light receiving side optical member RRS21 will be described as an upper surface of the first light receiving side optical member RRS21.

In the example shown in FIGS. 12 and 13, when viewed in the first direction A21, the first light receiving side optical member RRS21 is divided into a first light receiving side non-protruding region that overlaps the accommodating member CS2 and a first light receiving side protruding region that does not overlap the accommodating member CS2. In addition, in that case, a shape of the first light receiving side optical member RRS21 is a rectangular shape. In other words, in that case, a shape of a region that overlaps the second opening H22 among regions included in the first light receiving side optical member RRS21 is a rectangular shape. That is, in the detection device 2, the second opening H22 is completely filled with the resin forming the first light receiving side optical member RRS21 except for a gap unintentionally formed in the manufacturing process. For this reason, a contour of a cross-section of the first light receiving side optical member RRS21 along a virtual plane including the upper surface of the accommodating member CS2 coincides with a shape of an inner edge of the second opening H22 when viewed in the third direction A23. Thus, the detection device 2 can inhibit occurrence of refraction of light in the second opening H22, and as a result, can inhibit generation of stray light.

On the other hand, in that case, the first light receiving side protruding region has an upwardly convex dome shape. Also, the shape of the first light receiving side optical member RRS21 is a rectangular shape when viewed in the third direction A23. Further, the upper surface of the first light receiving side optical member RRS21 has a portion having the highest height from the accommodating member CS2 in the third direction A23 as a second vertex portion TP2. In addition, a height of the upper surface of the first light receiving side optical member RRS21 from the substrate BD2 increases from an end portion of the upper surface toward the second vertex portion TP2. In the example shown in FIG. 12, the upper surface of the first light receiving side optical member RRS21 further has a gradient that gradually becomes gentler from the end portion of the upper surface toward the second vertex portion TP2. The second vertex portion TP2 may be a point-like portion, a linearly extending portion, a band-like extending portion, or a planarly extending portion.

In the example shown in FIGS. 12 and 13, the second vertex portion TP2 extends in a band shape in the first direction A21 to couple both ends of the first light receiving side optical member RRS21 in the first direction A21. Also, in the example, when viewed in the first direction A21, the second vertex portion TP2 overlaps a second virtual line segment AX2 that passes through a center of a surface in the third direction A23 among surfaces included in the first light receiving unit R21 and extends in the third direction A23. Such a first light receiving side optical member RRS21 can refract some of light incident on the first light receiving side optical member RRS21 at the upper surface of the first light receiving side optical member RRS21 in a direction toward the first light receiving unit R21.

For example, the first light incident on the first light receiving side optical member RRS21 in the direction indicated by arrow LT33 shown in FIG. 12 is refracted at a surface of a second light emitting side protruding region in the third direction A23 and travels in the direction indicated by arrow LT34. The direction indicated by arrow LT34 is an example of a direction toward the first light receiving unit R21. That is, the detection device 2 can refract the first light reflected in the skin of the person toward the first light receiving unit R21 using the first light receiving side optical member RRS21. As a result, the detection device 2 can increase the amount of light received by the first light receiving unit R21 in the first light reflected in the skin of the person. In addition, such an increase in the amount of received light leads to a reduction in the amount of the component that becomes stray light in the first light emitted from the first light emitting unit L21. As a result, the detection device 2 can reduce noise in pulse detection and improve the S/N ratio for pulse detection.

Also, the second light receiving side optical member RRS22 protrudes from the third opening H23 formed in the accommodating member CS2 in the third direction A23. In addition, a surface in the third direction A23 among surfaces included in the second light receiving side optical member RRS22 includes a curved surface having a positive gradient in the third direction A23. In the second embodiment, for convenience of description, the surface in the third direction A23 among surfaces included in the second light receiving side optical member RRS22 will be described as an upper surface of the second light receiving side optical member RRS22.

In the example shown in FIGS. 12 and 13, when viewed in the first direction A21, the second light receiving side optical member RRS22 is divided into a second light receiving side non-protruding region that overlaps the accommodating member CS2 and a second light receiving side protruding region that does not overlap the accommodating member CS2. In addition, in that case, a shape of the second light receiving side optical member RRS22 is a rectangular shape. In other words, in that case, a shape of a region that overlaps the third opening H23 among regions included in the second light receiving side optical member RRS22 is a rectangular shape. That is, in the detection device 2, the third opening H23 is completely filled with the resin forming the second light receiving side optical member RRS22 except for a gap unintentionally formed in the manufacturing process. For this reason, a contour of a cross-section of the second light receiving side optical member RRS22 along a virtual plane including the upper surface of the accommodating member CS2 coincides with a shape of an inner edge of the third opening H23 when viewed in the third direction A23. Thus, the detection device 2 can inhibit refraction of light in the third opening H23, and as a result, can inhibit generation of stray light.

On the other hand, in that case, the second light receiving side protruding region has an upwardly convex dome shape. The shape of the second light receiving side optical member RRS22 is a rectangular shape when viewed in the third direction A23, and the upper surface of the second light receiving side optical member RRS22 has a portion having the highest height from the accommodating member CS2 in the third direction A23 as a third vertex portion TP3. In addition, a height of the upper surface of the second light receiving side optical member RRS22 from the substrate BD2 increases from an end portion of the upper surface toward the third vertex portion TP3. In the example shown in FIG. 12, the upper surface of the second light receiving side optical member RRS22 further has a gradient that gradually becomes gentler from the end portion of the upper surface toward the third vertex portion TP3. The third vertex portion TP3 may be a point-like portion, a linearly extending portion, a band-like extending portion, or a planarly extending portion.

In the example shown in FIGS. 12 and 13, the third vertex portion TP3 extends in a band shape in the first direction A21 to couple both ends of the second light receiving side optical member RRS22 in the first direction A21. Also, in the example, when viewed in the first direction A21, the third vertex portion TP3 overlaps a third virtual line segment AX3 that passes through a center of a surface in the third direction A23 among surfaces included in the second light receiving unit R22 and extends in the third direction A23. Such a second light receiving side optical member RRS22 can refract some of light incident on the second light receiving side optical member RRS22 at the upper surface of the second light receiving side optical member RRS22 in a direction toward the second light receiving unit R22.

For example, each of the second light and the third light incident on the second light receiving side optical member RRS22 in the direction indicated by arrow LT35 shown in FIG. 12 is refracted at a surface of a third light emitting side protruding region in the third direction A23 and travels in the direction indicated by arrow LT36. The direction indicated by arrow LT36 is an example of the direction toward the second light receiving unit R22. That is, the detection device 2 can refract each of the second light and the third light reflected in the skin of the person toward the second light receiving unit R22 using the second light receiving side optical member RRS22. As a result, the detection device 2 can increase the amount of light received by the second light receiving unit R22 in each of the second light and the third light reflected in the skin of the person. In addition, such an increase in the amount of received light leads to a decrease in the amount of the component that becomes stray light in the light emitted from each of the second light emitting unit L22 and the third light emitting unit L23. As a result, the detection device 2 can reduce noise in detecting oxygen saturation and can improve the S/N ratio for detecting oxygen saturation.

As described above, in the detection device 2, the first light emitting side optical member LRS21 protrudes from the first opening H21 in the third direction A23, the first light receiving side optical member RRS21 protrudes from the second opening H22 in the third direction A23, and the second light receiving side optical member RRS22 protrudes from the third opening H23 in the third direction A23. For this reason, the detection device 2 can increase the amount of light received by each of the first light receiving unit R21 and the second light receiving unit R22 without providing each of the first opening H21, the second opening H22, and the third opening H23 with a condensing lens that is brought into close contact with the skin of the person. As a result, the size of the detection device 2 in the third direction A23 can be reduced by amounts corresponding to the condensing lens, a member for attaching the condensing lens to the detection device 2, and the like.

In addition, in the detection device 2, the condensing lens that is brought into close contact with the skin of the person is not provided in each of the first opening H21, the second opening H22, and the third opening H23, and thus by shortening a distance between each of the first light emitting unit L21, the second light emitting unit L22, and the third light emitting unit L23 and the skin of the person, it is possible to increase the intensity of the light emitted to the skin, as compared with a case in which the condensing lens is provided. This leads to a reduction in power consumption, which is useful. Further, for the same reason, the detection device 2 can reduce the number of components required for manufacturing and can inhibit an increase in manufacturing costs. Also, the detection device 2 may have a configuration in which the first light emitting side optical member LRS21 does not protrude from the first opening H21 in the third direction A23. In this case, the detection device 2 may have a configuration in which a condensing lens to be brought into close contact with the skin of the person is provided in the first opening H21.

Also, the detection device 2 may have a configuration in which the first light receiving side optical member RRS21 does not protrude from the second opening H22 in the third direction A23. In this case, the detection device 2 may have a configuration in which a condensing lens to be brought into close contact with the skin of the person is provided in the second opening H22. In addition, the detection device 2 may have a configuration in which the second light receiving side optical member RRS22 does not protrude from the third opening H23 in the third direction A23. In this case, the detection device 2 may have a configuration in which a condensing lens to be brought into close contact with the skin of the person is provided in the third opening H23.

Also, the heights of each of the first light emitting side protruding region, the second light emitting side protruding region, and the third light emitting side protruding region from the upper surface of the accommodating member CS2 when viewed in the first direction A21 are the same in order to improve adhesion to the skin of the person, except for differences due to manufacturing errors. In addition, the heights of each of the first light emitting side protruding region, the second light emitting side protruding region, and the third light emitting side protruding region from the upper surface of the accommodating member CS2 when viewed in the first direction A21 are equal to or higher than a first height satisfying a predetermined first condition and equal to or lower than a second height satisfying a predetermined second condition. For example, the first condition is a height at which contact with human skin is not reduced. In this case, the first height is, for example, about 0.2 [mm], but is not limited thereto. This is because an average thickness of the human epidermis is 0.2 [mm], and adhesion between the detection device 2 and the skin of the person increases as the heights of each of the first light emitting side protruding region, the second light emitting side protruding region, and the third light emitting side protruding region from the upper surface of the accommodating member CS2 are closer to the average thickness of the epidermis.

Also, the first condition may be another condition that can define a height at which the adhesion to the skin of the person does not decrease. Further, the second condition may be any condition as long as it is a condition that can define a height at which an amount of hemoglobin contained in blood vessels in the skin of the person does not change due to close contact between the detection device 2 and the skin of the person. For example, the second condition is a height at which capillary vessels in human dermis do not collapse. In this case, the second height is about 1.2 [mm], but is not limited thereto. This is because an average thickness of the human dermis is 2 [mm], and when the dermis is collapsed to the extent that a thickness of the dermis becomes half or less, capillary vessels in the dermis are collapsed.

Also, in the example shown in FIG. 13, a distance W7 between the first light emitting side optical member LRS21 and the first light receiving side optical member RRS21 in the second direction A22 is longer than a distance W8 between the first light receiving side optical member RRS21 and the second light receiving side optical member RRS22 in the second direction A22. In this case, the detection device 2 can reduce the amount of the first light that is reflected near the epidermis of the person and received by the first light receiving unit R21 in the first light emitted from the first light emitting unit L11. Since the first light is not reflected by hemoglobin in blood vessels, it is light that becomes noise in pulse detection. That is, the detection device 2 can reduce noise in pulse detection by making the distance W7 longer than the distance W8.

The detection device 2 having the above configuration can be manufactured, for example, by a manufacturing method as described below. First, the manufacturer of the detection device 2 provides the first light emitting unit L21, the second light emitting unit L22, the third light emitting unit L23, the first light receiving unit R21, and the second light receiving unit R22 at the upper surface of the substrate BD2 using die bonding and wire bonding. In the following description, for convenience of description, unless it is necessary to distinguish the first light emitting unit L21, the second light emitting unit L22, the third light emitting unit L23, the first light receiving unit R21, and the second light receiving unit R22 from each other, they will be collectively described as installed elements.

Figure 14:
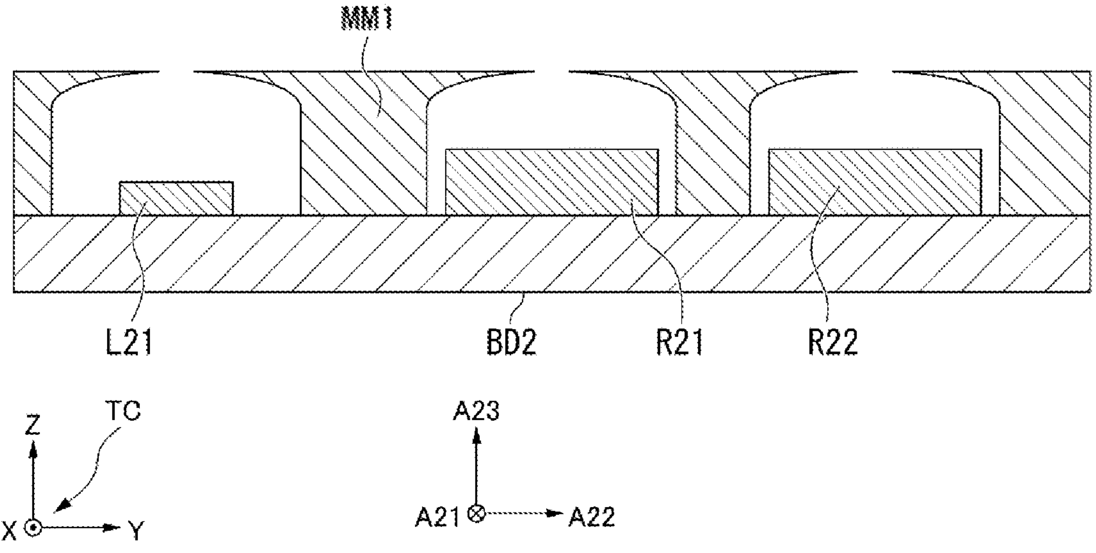
FIG. 14 is a cross-sectional view showing an example of a state in which a mold MM1 is placed on an upper surface of a substrate BD2.

After providing the installed elements at the upper surface of the substrate BD2, as shown in FIG. 14, the manufacturer uses a mold MM1 to fill and harden the resins forming each of the first light emitting side optical member LRS21, the first light receiving side optical member RRS21, and the second light receiving side optical member RRS22 at the upper surface of the substrate BD2. FIG. 14 is a cross-sectional view showing an example of a state in which the mold MM1 is placed at the upper surface of the substrate BD2. However, the cross-sectional view shown in FIG. 14 is a cross-sectional view of the substrate BD2 and the mold MM1 along a virtual plane orthogonal to the first direction A21 so that each of the first light emitting unit L21, the first light receiving unit R21, and the second light receiving unit R22 can be seen when viewed in the first direction A21.

The mold MM1 is a mold in which recessed portions having shapes to be fitted to each of the first light emitting side optical member LRS21, the first light receiving side optical member RRS21, and the second light receiving side optical member RRS22 are formed. In addition, holes for filling the resins are formed at upper surfaces of the recessed portions. When the mold MM1 is placed on a predetermined placement position at the upper surface of the substrate BD2, a position of the recessed portion corresponding to the first light emitting side optical member LRS21 among the recessed portions coincides with a predetermined position at which the first light emitting side optical member LRS21 is positioned at the upper surface of the substrate BD2. Further, in that case, a position of the recessed portion corresponding to the first light receiving side optical member RRS21 among the recessed portions coincides with a predetermined position at which the first light receiving side optical member RRS21 is positioned at the upper surface of the substrate BD2. Also, in that case, a position of the recessed portion corresponding to the second light receiving side optical member RRS22 among the recessed portions coincides with a predetermined position at which the second light receiving side optical member RRS22 is positioned at the upper surface of the substrate BD2.

Thus, by filling and hardening the resins in the three recessed portions formed in the mold MM1 after being placed at the upper surface of the substrate BD2, the manufacturer can form each of the first light emitting side optical member LRS21, the first light receiving side optical member RRS21, and the second light receiving side optical member RRS22 at the upper surface of the substrate BD2.

Figure 15:
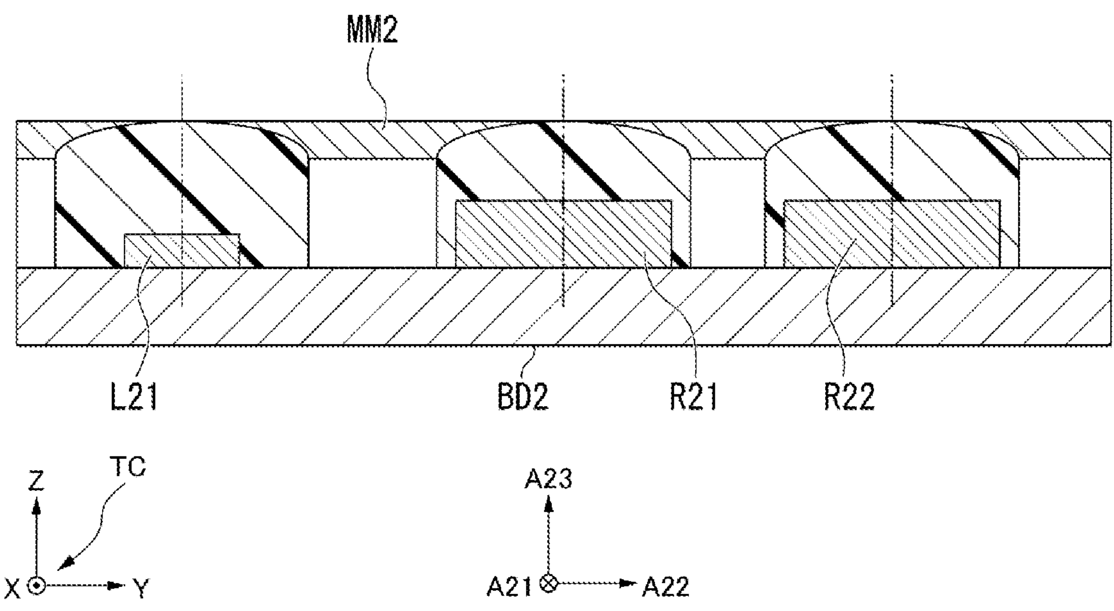
FIG. 15 is a cross-sectional view showing an example of a state in which a mold MM2 is placed at the upper surface of the substrate BD2.

Next, the manufacturer forms the accommodating member CS2 at the upper surface of the substrate BD2 using a mold MM2 as shown in FIG. 15. FIG. 15 is a cross-sectional view showing an example of a state in which the mold MM2 is placed at the upper surface of the substrate BD2. However, the cross-sectional view shown in FIG. 15 is a cross-sectional view of the substrate BD2 and the mold MM2 along a virtual plane orthogonal to the first direction A21 so that each of the first light emitting unit L21, the first light receiving unit R21, and the second light receiving unit R22 can be seen when viewed in the first direction A21.

The mold MM2 is a mold in which recessed portions that cover each of the first light emitting side protruding region, the first light receiving side protruding region, and the second light receiving side protruding region from above are formed when the mold MM2 is placed at upper surfaces of each of the first light emitting side optical member LRS21, the first light receiving side optical member RRS21, and the second light receiving side optical member RRS22. An outer shape of the mold MM2 is a rectangular parallelepiped shape as a whole. In addition, the mold MM2 does not cover side surfaces of each of the first light emitting side non-protruding region, the first light receiving side non-protruding region, and the second light receiving side non-protruding region. For this reason, the manufacturer can form the accommodating member CS2, for example, by filling and hardening the white resin between the mold MM2 and the substrate BD2. The manufacturer can manufacture the detection device 2 using the manufacturing method described above.

Figure 16:
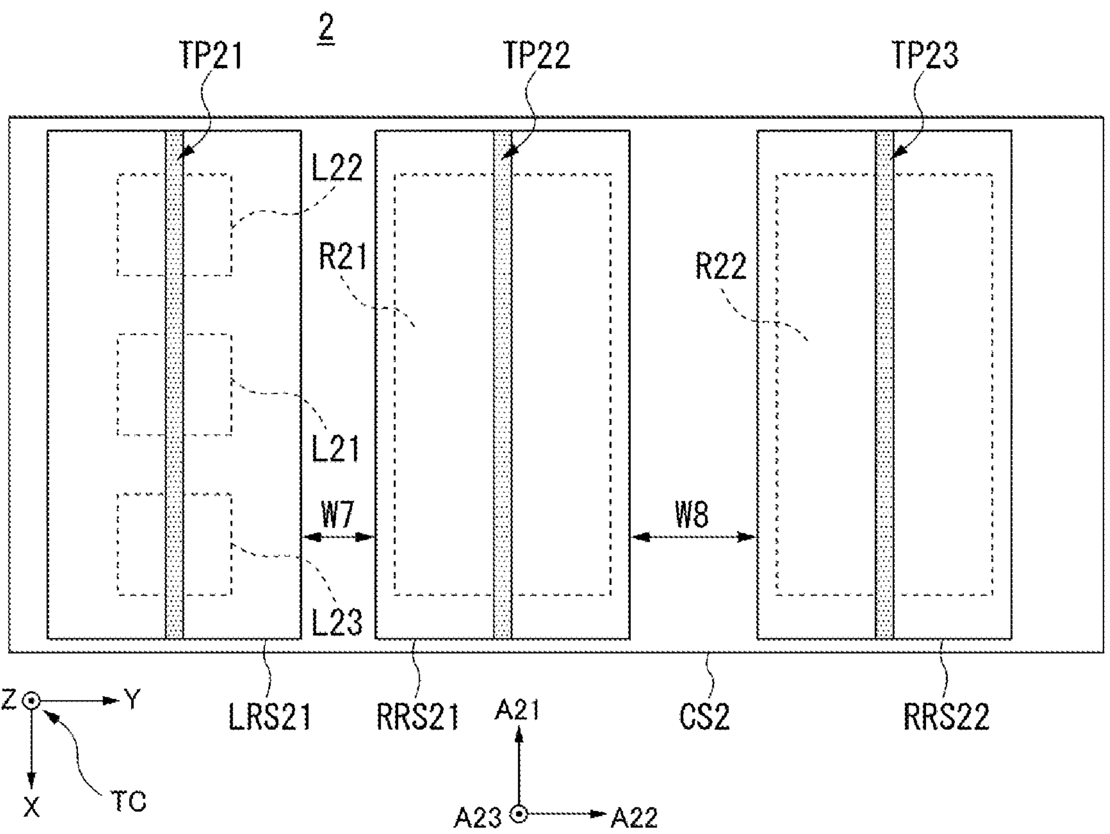
FIG. 16 is a top view showing a second configuration example of the detection device 2.

Also, the detection device 2 may have a configuration in which the distance W7 between the first light emitting side optical member LRS21 and the first light receiving side optical member RRS21 in the second direction A22 is shorter than the distance W8 between the first light receiving side optical member RRS21 and the second light receiving side optical member RRS22 in the second direction A22, as shown in FIG. 16. FIG. 16 is a top view showing a second configuration example of the detection device 2. Thus, in the detection device 2, the distance between the first light emitting unit L11 and the first light receiving unit R21 can be reduced, and as a result, the amount of light received by the first light receiving unit R21 in the first light reflected in the skin of the person can be increased.

Figure 17:
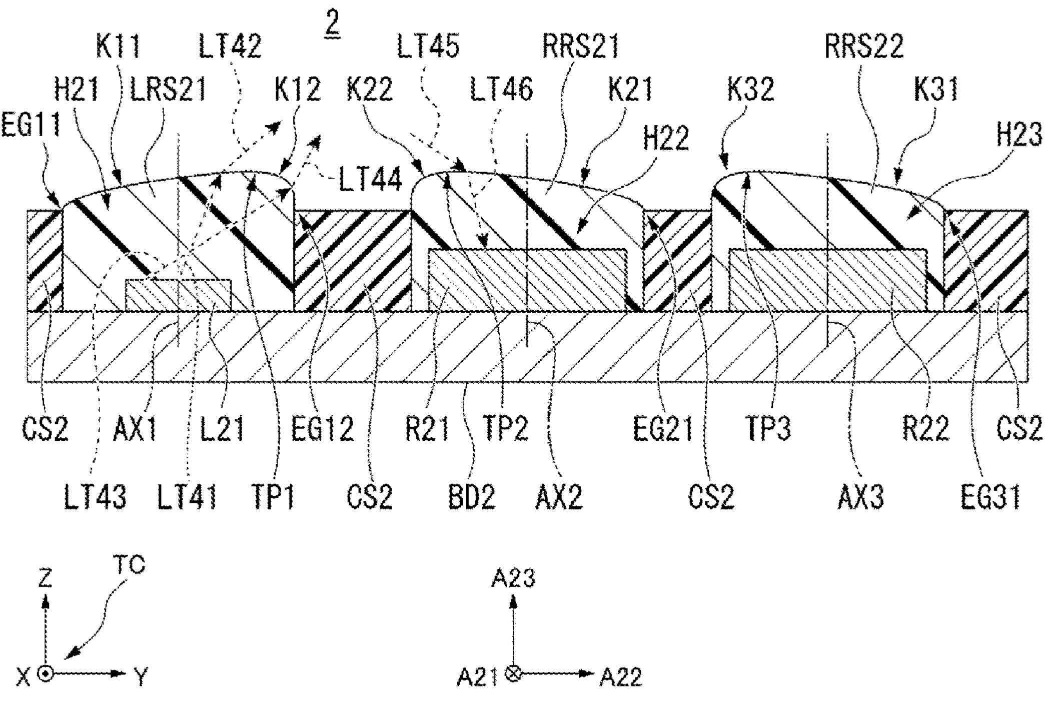
FIG. 17 is a cross-sectional view showing a third configuration example of the detection device 2.
Figure 18:
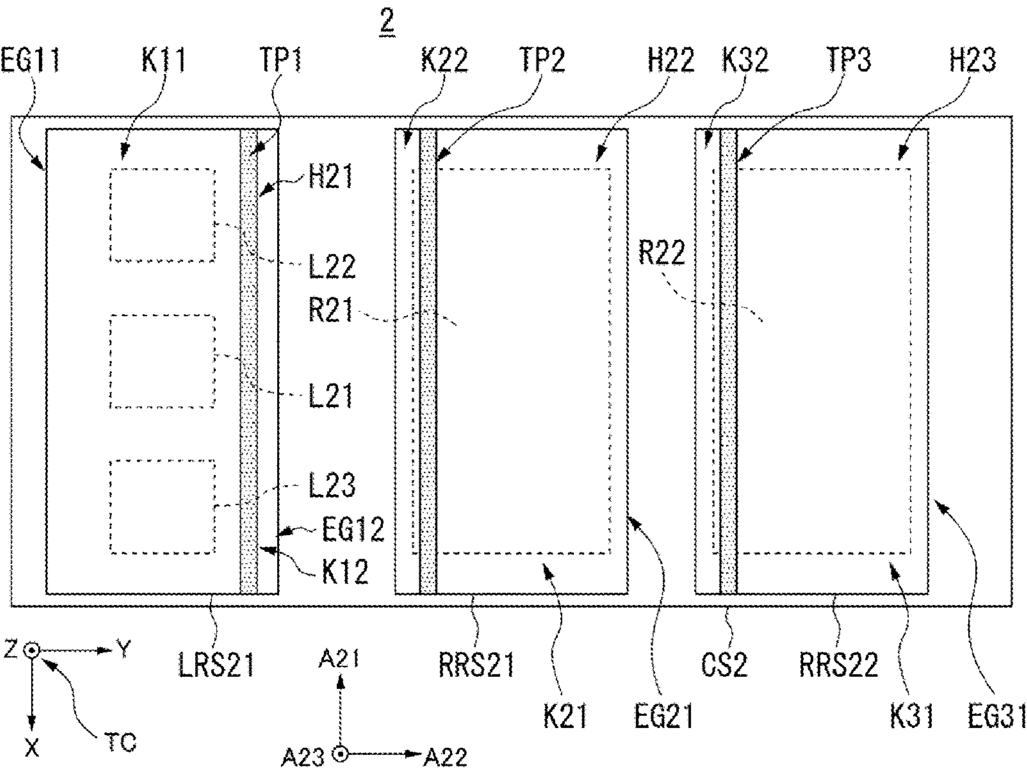
FIG. 18 is a top view of the detection device 2 shown in FIG. 17.

Here, the first light emitted from the first light emitting unit L21 is more likely to be received by the first light receiving unit R21 as the first light is reflected at a position closer to the first light receiving unit R21 in the skin of the person. Similarly, the second light emitted from the second light emitting unit L22 and the third light emitted from the third light emitting unit L23 are more likely to be received by the second light receiving unit R22 as they are reflected at positions closer to the second light receiving unit R22 in the skin of the person. Thus, when viewed in the first direction A21, as shown in FIGS. 17 and 18, the detection device 2 may have a configuration in which the first vertex portion TP1 does not overlap the first line segment AX1 and is closer to the first light receiving unit R21 than the first line segment AX1. FIG. 17 is a cross-sectional view showing a third configuration example of the detection device 2. However, the cross-sectional view shown in FIG. 17 is a cross-sectional view of the detection device 2 along a virtual plane orthogonal to the first direction A21 so that each of the first light emitting unit L21, the first light receiving unit R21, and the second light receiving unit R22 can be seen when viewed in the first direction A21. FIG. 18 is a top view of the detection device 2 shown in FIG. 17.

When the first vertex portion TP1 is located on a side of the first light emitting side optical member LRS21 closer to the first light receiving unit R21 with the first line segment AX1 as a reference, a surface K11 in a direction opposite to the second direction A22 from the first vertex portion TP1 among surfaces included in the upper surface of the first light emitting side optical member LRS21 is wider than a surface K12 on a side in the second direction A22 from the first vertex portion TP1 among the surfaces included in the upper surface. For this reason, most of the first light emitted from the first light emitting unit L21 is incident toward the surface K11.

When viewed in the first direction A21, the surface K11 is a curved surface having a positive gradient from an end portion EG11 in a direction opposite to the second direction A22 among end portions included in the surface K11 toward the first vertex portion TP1. In the example shown in FIG. 17, in that case, a height of the surface K11 from the substrate BD2 increases from the end portion EG11 toward the first vertex portion TP1, and a gradient thereof gradually becomes gentler from the end portion EG11 toward the first vertex portion TP1. In this case, when viewed in the first direction A21, the first light incident on the surface K11 of the first light emitted from the first light emitting unit L21 is refracted at the surface K11 so that its traveling direction is shifted toward the second direction A22.

For example, the first light emitted from the first light emitting unit L21 in the direction indicated by arrow LT41 shown in FIG. 17 is an example of the first light incident on the surface K11 in the first light emitted from the first light emitting unit L21 toward the surface K11. The first light emitted from the first light emitting unit L21 in the direction indicated by arrow LT41 is refracted at the surface K11 to travel in the direction indicated by arrow LT42. In addition, as shown in FIG. 17, the direction indicated by arrow LT42 is shifted from the direction indicated by arrow LT41 toward the second direction A22. Accordingly, when the first vertex portion TP1 is closer to the first light receiving unit R21 than the first line segment AX1, the detection device 2 can reflect the first light incident on the surface K11 in the first light emitted from the first light emitting unit L21 at a position closer to the first light receiving unit R21 among positions in the skin of the person. As a result, the detection device 2 can increase the amount of light received by the first light receiving unit R21 in the first light reflected in the skin of the person and can improve the S/N ratio for pulse detection by the detection device 2.

In addition, this situation also applies to the second light and the third light. That is, when the first vertex portion TP1 is closer to the first light receiving unit R21 than the first line segment AX1, the detection device 2 can reflect the second light incident on the surface K11 in the second light emitted from the second light emitting unit L22 at a position closer to the second light receiving unit R22 among the positions in the skin of the person, and can reflect the third light incident on the surface K11 in the third light emitted from the third light emitting unit L23 at a position closer to the second light receiving unit R22 among the positions in the skin of the person. As a result, the detection device 2 can increase the amount of light received by the second light receiving unit R22 in the second light and the third light reflected in the skin of the person, and can improve the S/N ratio for detection of the oxygen saturation by the detection device 2.

On the other hand, since the traveling direction of the first light incident on the surface K12 in the first light emitted from the first light emitting unit L21 is too close to the second direction A22, there is a high possibility of the first light becoming stray light. However, when viewed in the first direction A21, the surface K12 is also a curved surface having a positive gradient from an end portion EG12 in the second direction A22 among end portions of the surface K12 toward the first vertex portion TP1. In the example shown in FIG. 17, in that case, a height of the surface K12 from the substrate BD2 decreases from the first vertex portion TP1 toward the end portion EG12, and a gradient thereof becomes steeper from the first vertex portion TP1 toward the end portion EG12. In this case, when viewed in the first direction A21, the first light incident on the surface K12 in the first light emitted from the first light emitting unit L21 is refracted at the surface K12 so that the traveling direction is shifted toward the third direction A31.

For example, the first light emitted from the first light emitting unit L21 in the direction indicated by arrow LT43 shown in FIG. 17 is an example of the first light incident on the surface K12 in the first light emitted from the first light emitting unit L21 toward the surface K12. The first light emitted from the first light emitting unit L21 in the direction indicated by arrow LT43 is refracted at the surface K12 to travel in the direction indicated by arrow LT44. In addition, as shown in FIG. 17, the direction indicated by arrow LT44 is shifted from the direction indicated by arrow LT43 toward the third direction A23. Accordingly, when the first vertex portion TP1 is closer to the first light receiving unit R21 than the first line segment AX1, the detection device 2 can inhibit the first light incident on the surface K12 in the first light emitted from the first light emitting unit L21 from becoming stray light. As a result, the detection device 2 can increase the amount of light received by the first light receiving unit R21 in the first light reflected in the skin of the person and can improve the S/N ratio for pulse detection by the detection device 2.

In addition, this situation also applies to the second light and the third light. That is, when the first vertex portion TP1 is closer to the first light receiving unit R21 than the first line segment AX1, the detection device 2 can inhibit the second light incident on the surface K12 in the second light emitted from the second light emitting unit L22 from becoming stray light and can inhibit the third light incident on the surface K12 in the third light emitted from the third light emitting unit L23 from becoming stray light. As a result, the detection device 2 can increase the amount of light received by the second light receiving unit R22 in the second light and the third light reflected in the skin of the person and can improve the S/N ratio for detection of the oxygen saturation by the detection device 2.

Further, as shown in FIGS. 17 and 18, the detection device 2 may have a configuration in which, in the first light receiving side optical member RRS21, the second vertex portion TP2 does not overlap the second line segment AX2 and the second vertex portion TP2 is closer to the first light emitting unit L21 than the second line segment AX2. In this case, a shape of the upper surface of the first light emitting side optical member LRS21 when viewed in the first direction A21 is different from a shape of the upper surface of the first light receiving side optical member RRS21 when viewed in the first direction A21.

When the second vertex portion TP2 is closer to the first light emitting unit L21 than the second line segment AX2, a surface K21 in the second direction A22 from the second vertex portion TP2 among surfaces included in the upper surface of the first light receiving side optical member RRS21 is wider than a surface K22 in a direction opposite to the second direction A22 from the second vertex portion TP2 among the surfaces included in the upper surface. For this reason, most of the first light reflected in the skin of the person is incident toward the surface K21.

When viewed in the first direction A21, the surface K21 is a curved surface having a positive gradient from an end portion EG21 in the second direction A22 among end portions included in the surface K21 toward the second vertex portion TP2. In the example shown in FIG. 17, in that case, a height of the surface K21 from the substrate BD2 increases from the end portion EG21 toward the second vertex portion TP2, and a gradient thereof gradually becomes gentler from the end portion EG21 toward the second vertex portion TP2. In this case, when viewed in the first direction A21, the first light incident on the surface K21 in the first light reflected in the skin of the person is refracted at the surface K21 so that the traveling direction is shifted toward a direction opposite to the third direction A23.

For example, the first light incident on the surface K21 in the direction indicated by arrow LT45 shown in FIG. 17 is an example of the first light incident on the surface K21 in the first light reflected in the skin of the person. The first light incident on the surface K21 in the direction indicated by arrow LT45 is refracted at the surface K21 to travel in the direction indicated by arrow LT46. In addition, as shown in FIG. 17, the direction indicated by arrow LT46 is shifted from the direction indicated by arrow LT45 toward the third direction A23. Accordingly, when the second vertex portion TP2 is closer to the first light emitting unit L21 than the second line segment AX2, the detection device 2 can reflect the first light incident on the surface K21 in the first light reflected in the skin of the person toward the first light receiving unit R21. As a result, the detection device 2 can increase the amount of light received by the first light receiving unit R21 in the first light reflected in the skin of the person and can improve the S/N ratio in pulse detection by the detection device 2.

Also, this situation also applies to the second light and the third light. However, the second light and the third light have longer mean free paths in the skin of the person than the first light. For this reason, the amount of the second light and the third light incident on the first light receiving side optical member RRS21 is smaller than that of the first light. For this reason, in the second embodiment, description of the relationship between the upper surface of the first light receiving side optical member RRS21 and each of the second light and the third light will be omitted. In addition, the amount of the first light incident on the surface K22 in the first light reflected in the skin of the person is also smaller than the amount of the first light incident on the surface K21 in the first light reflected in the skin of the person. For this reason, in the second embodiment, description of the relationship between the surface K21 and the first light incident on the surface K21 will also be omitted.

Also, as shown in FIGS. 17 and 18, the detection device 2 may have a configuration in which the third vertex portion TP3 does not overlap the third line segment AX3 and the third vertex portion TP3 is closer to the first light emitting unit L21 than the third line segment AX3 in the second light receiving side optical member RRS22. In this case, a shape of the upper surface of the first light emitting side optical member LRS21 when viewed in the first direction A21 is different from a shape of the upper surface of the second light receiving side optical member RRS22 when viewed in the first direction A21.

When the third vertex portion TP3 is closer to the first light emitting unit L21 than the third line segment AX3, a surface K31 in the second direction A22 from the third vertex portion TP3 among surfaces included in the upper surface of the second light receiving side optical member RRS22 is wider than a surface K32 in the direction opposite to the second direction A22 from the third vertex portion TP3 among the surfaces included in the upper surface. For this reason, most of each of the second light and the third light reflected in the skin of the person is incident toward the surface K31.

When viewed in the first direction A21, the surface K31 is a curved surface having a positive gradient from an end portion EG31 in the second direction A22 among end portions included in the surface K31 toward the third vertex portion TP3. In the example shown in FIG. 17, in that case, a height of the surface K31 from the substrate BD2 increases from the end portion EG31 toward the third vertex portion TP3, and a gradient thereof gradually becomes gentler from the end portion EG31 toward the third vertex portion TP3. In this case, when viewed in the first direction A21, the second light incident on the surface K31 in the second light reflected in the skin of the person is refracted at the surface K31 so that the traveling direction is shifted toward the direction opposite to the third direction A23. This also applies to the third light.

In addition, such a refraction occurs for the same reason as the reason why the first light is refracted when the first light is incident on the surface K21 of the first light receiving side optical member RRS21 shown in FIG. 17. For this reason, in the second embodiment, descriptions of refraction of the second light when the second light is incident on the surface M31 and refraction of the third light when the third light is incident on the surface M31 will be omitted. When the third vertex portion TP3 is closer to the first light emitting unit L21 than the third line segment AX3, the detection device 2 can reflect the second light incident on the surface K31 in the second light reflected in the skin of the person toward the second light receiving unit R22. As a result, the detection device 2 can increase the amount of light received by the second light receiving unit R22 in the second light reflected in the skin of the person and can improve the S/N ratio for detection of the oxygen saturation by the detection device 2.

Further, when the third vertex portion TP3 is closer to the first light emitting unit L21 than the third line segment AX3, the detection device 2 can reflect the third light incident on the surface K31 in the third light reflected in the skin of the person toward the second light receiving unit R22. As a result, the detection device 2 can increase the amount of light received by the second light receiving unit R22 in the third light reflected in the skin of the person and can improve the S/N ratio for detection of the oxygen saturation by the detection device 2.

Also, the second light and the third light have longer mean free paths in the skin of the person than the first light, and thus they tend to be reflected in a deep layer of the skin of the person. For this reason, the traveling directions of the second light and the third light reflected in the skin of the person are often close to the direction opposite to the third direction A23. Thus, a distance between the third line segment AX3 and the third vertex portion TP3 in the second direction A22 may be configured to be shorter than the distance between the second line segment AX2 and the second vertex portion TP2 in the second direction A22. In this case, the shape of the upper surface of the first light receiving side optical member RRS21 when viewed in the first direction A21 is different from the shape of the upper surface of the second light receiving side optical member RRS22 when viewed in the first direction A21. Thus, the detection device 2 can increase the amount of each of the second light and the third light received by the second light receiving unit R22.

Figure 19:
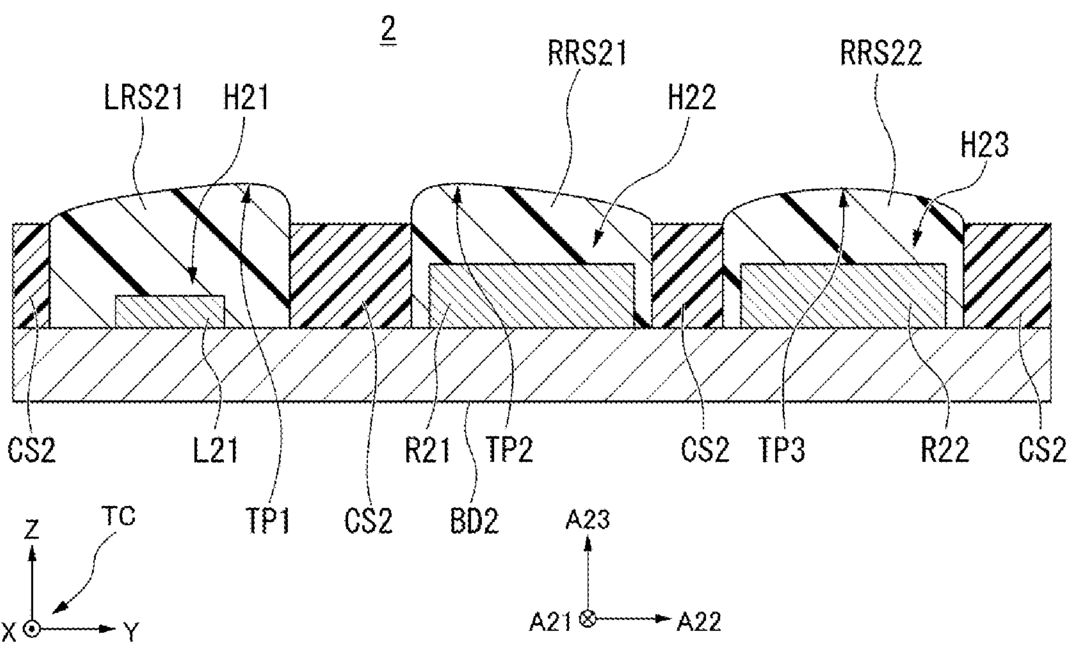
FIG. 19 is a cross-sectional view showing a fourth configuration example of the detection device 2.
Figure 20:
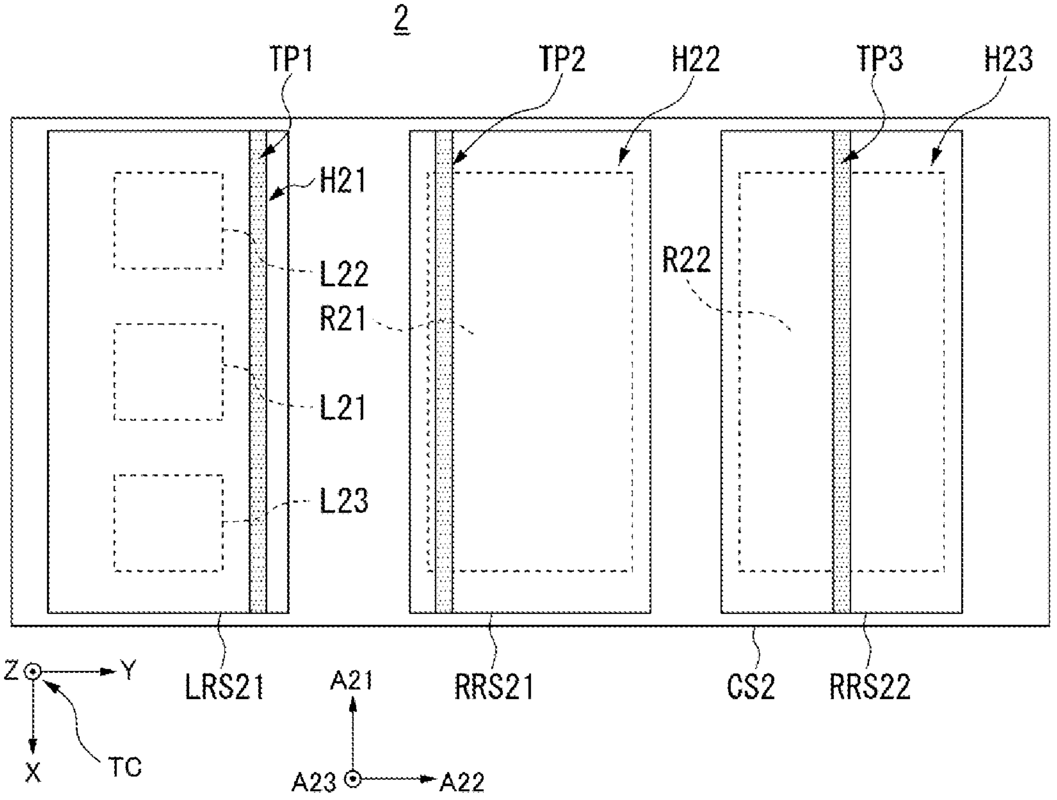
FIG. 20 is a top view of the detection device 2 shown in FIG. 19.

The configuration of the detection device 2 shown in FIGS. 19 and 20 is a configuration obtained by further modifying the above configuration. That is, in the detection device 2 shown in FIG. 17, the shape of the upper surface of the second light receiving side optical member RRS22 may be a shape in which the third vertex portion TP3 overlaps the third line segment AX3 when viewed in the first direction A21, as shown in FIGS. 19 and 20.

FIG. 19 is a cross-sectional view showing a fourth configuration example of the detection device 1. However, the cross-sectional view shown in FIG. 19 is a cross-sectional view of the detection device 2 along a virtual plane orthogonal to the first direction A21 so that each of the first light emitting unit L21, the first light receiving unit R21, and the second light receiving unit R22 can be seen when viewed in the first direction A21.

FIG. 20 is a top view of the detection device 2 shown in FIG. 19. Also in this case, the shape of the upper surface of the first light receiving side optical member RRS21 when viewed in the first direction A21 is different from the shape of the upper surface of the second light receiving side optical member RRS22 when viewed in the first direction A21.

The shape of the first light emitting side optical member LRS21 shown in FIGS. 19 and 20 is the same as the shape of the first light emitting side optical member LRS21 shown in FIGS. 17 and 18. In addition, the shape of the first light receiving side optical member RRS21 shown in FIGS. 19 and 20 is the same as the shape of the first light receiving side optical member RRS21 shown in FIGS. 17 and 18. On the other hand, the shape of the first light emitting side optical member LRS21 shown in FIGS. 19 and 20 is a shape in which the third vertex portion TP3 overlaps the third line segment AX3 when viewed in the first direction A21. In other words, the shape of the second light receiving side optical member RRS22 shown in FIGS. 19 and 20 is the same as the shape of the second light receiving side optical member RRS22 shown in FIGS. 12 and 13.

In this case, the second light and the third light incident in the direction opposite to the third direction A23 at a position not included in the third vertex portion TP3 among positions of the upper surface of the second light receiving side optical member RRS22 are refracted in the direction toward the second light receiving unit R22. That is, when viewed in the first direction A21, by forming the shape of the upper surface of the second light receiving side optical member RRS22 to be a shape that overlaps the third line segment AX3, the detection device 2 can increase the amount of light received by the second light receiving unit R22 in the second light and the third light reflected in the skin of the person.

Figure 21:
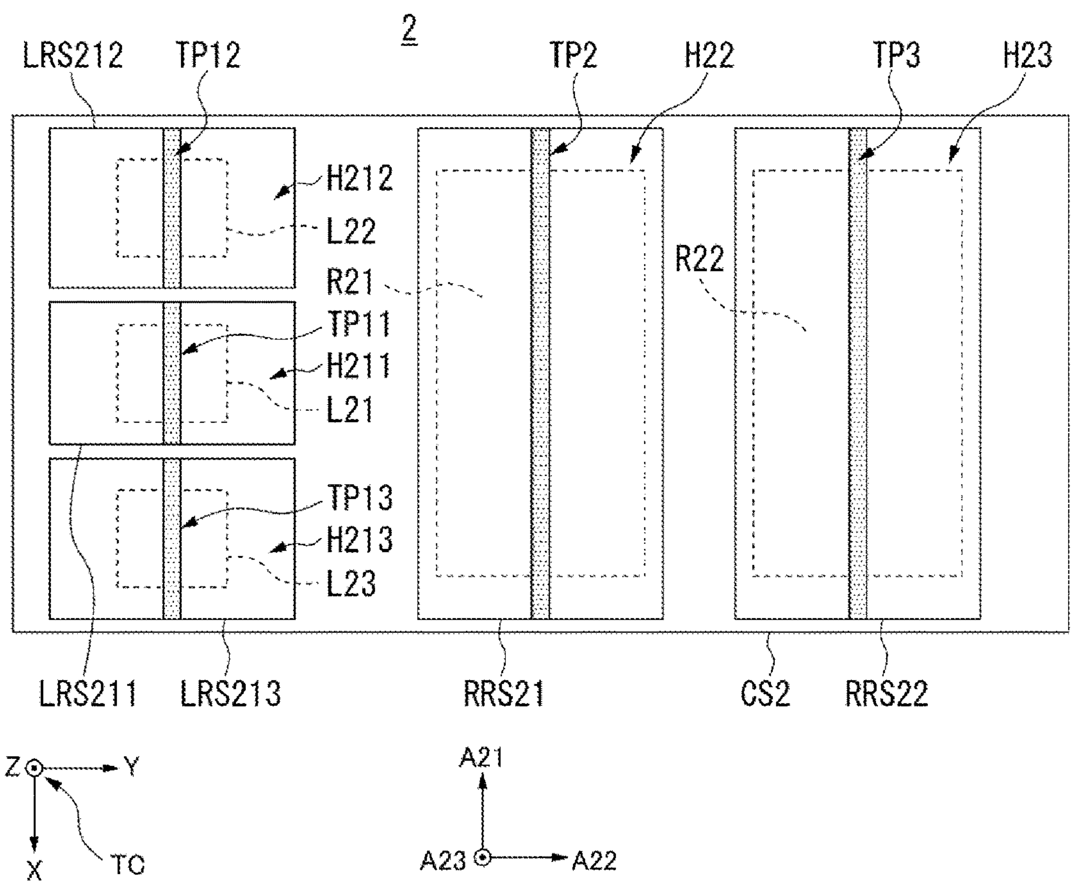
FIG. 21 is a top view showing a fifth configuration example of the detection device 2.

Also, in order to reduce the amount of the component that becomes stray light in the light emitted from each of the first light emitting unit L21, the second light emitting unit L22, and the third light emitting unit L23, as shown in FIG. 21, the detection device 2 may have a configuration in which the first light emitting side optical member LRS21 is divided into the three optical members. FIG. 21 is a top view showing a fifth configuration example of the detection device 2. In the example shown in FIG. 21, the first light emitting side optical member LRS21 is divided into three optical members, that is, a first light emitting side optical member LRS211 that covers the first light emitting unit L21 together with the substrate BD2, a second light emitting side optical member LRS212 that covers the second light emitting unit L22 together with the substrate BD2, and a third light emitting side optical member LRS213 that covers the third light emitting unit L23 together with the substrate BD2. For this reason, in the example shown in FIG. 21, three openings, that is, an opening H211, an opening H212, and an opening H213 are formed in the accommodating member CS2 instead of the first opening H21.

The opening H211 is a hole that penetrates the accommodating member CS2 in the third direction A23. The opening H211 is a hole in which the first light emitting unit L21 and the first light emitting side optical member LRS211 are accommodated at the upper surface of the substrate BD2. In the example shown in FIG. 21, a shape of a contour of the opening H211 is a rectangular shape when viewed in the first direction A21. In addition, in the example, the shape of the contour of the opening H211 is a rectangular shape when viewed in the third direction A23. That is, the shape of the opening H211 is a rectangular parallelepiped shape. Also, instead of the rectangular parallelepiped shape, the shape of the opening H211 may be another shape that can accommodate the first light emitting unit L21 and the first light emitting side optical member LRS211 at the upper surface of the substrate BD2. The other shape is, for example, a trapezoid, but is not limited thereto. The opening H212 is an example of the first opening.

The opening H212 is a hole that penetrates the accommodating member CS2 in the third direction A23. The opening H212 is a hole in which the second light emitting unit L22 and the second light emitting side optical member LRS212 are accommodated at the upper surface of the substrate BD2. In the example shown in FIG. 21, a shape of a contour of the opening H212 is a rectangular shape when viewed in the first direction A21. In addition, in the example, the shape of the contour of the opening H212 is a rectangular shape when viewed in the third direction A23. That is, the shape of the opening H212 is a rectangular parallelepiped shape. Also, instead of the rectangular parallelepiped shape, the shape of the opening H212 may be another shape that can accommodate the second light emitting unit L22 and the second light emitting side optical member LRS212 at the upper surface of the substrate BD2. The other shape is, for example, a trapezoid, but is not limited thereto. The opening H212 is an example of a fourth opening.

The opening H213 is a hole that penetrates the accommodating member CS2 in the third direction A23. The opening H213 is a hole in which the third light emitting unit L23 and the third light emitting side optical member LRS213 are accommodated at the upper surface of the substrate BD2. In the example shown in FIG. 21, a shape of a contour of the opening H213 is a rectangular shape when viewed in the first direction A21. In addition, in the example, the shape of the contour of the opening H213 is a rectangular shape when viewed in the third direction A23. That is, the shape of the opening H213 is a rectangular parallelepiped shape. Also, instead of the rectangular parallelepiped shape, the shape of the opening H213 may be another shape that can accommodate the third light emitting unit L23 and the third light emitting side optical member LRS213 at the upper surface of the substrate BD2. The other shape is, for example, a trapezoid, but is not limited thereto. The opening H213 is an example of the fourth opening.

Further, each of the first light emitting side optical member LRS211, the second light emitting side optical member LRS212, and the third light emitting side optical member LRS213 have a shape obtained by shortening a width of the first light emitting side optical member LRS21 in the first direction A21. For this reason, an upper surface of the first light emitting side optical member LRS211 corresponds to a part of the upper surface of the first light emitting side optical member LRS21 and includes a vertex portion TP11 corresponding to the first vertex portion TP1. Also, an upper surface of the second light emitting side optical member LRS212 corresponds to a part of the upper surface of the first light emitting side optical member LRS21 and includes a vertex portion TP12 corresponding to the first vertex portion TP1. Also, an upper surface of the third light emitting side optical member LRS213 corresponds to a part of the upper surface of the first light emitting side optical member LRS21 and includes a vertex portion TP13 corresponding to the first vertex portion TP1. Also, a shape of the upper surface of the first light emitting side optical member LRS211 when viewed in the second direction A22 is the same as a shape of the upper surface of the second light emitting side optical member LRS212 when viewed in the second direction A22. Also, the shape of the upper surface of the first light emitting side optical member LRS211 when viewed in the second direction A22 is the same as a shape of the upper surface of the third light emitting side optical member LRS213 when viewed in the second direction A22.

In such a detection device 2, for example, in the first light emitted from the first light emitting unit L21, the first light traveling toward a wall surface forming the opening H211 is reflected by the wall surface and travels upward from the opening H211. Thus, the detection device 2 can increase the amount of the first light incident on the skin of the person. This situation also applies to each of the second light and the third light. As a result, the detection device 2 can reduce the amount of the component that becomes stray light in the light emitted from each of the first light emitting unit L21, the second light emitting unit L22, and the third light emitting unit L23.

Figure 22:
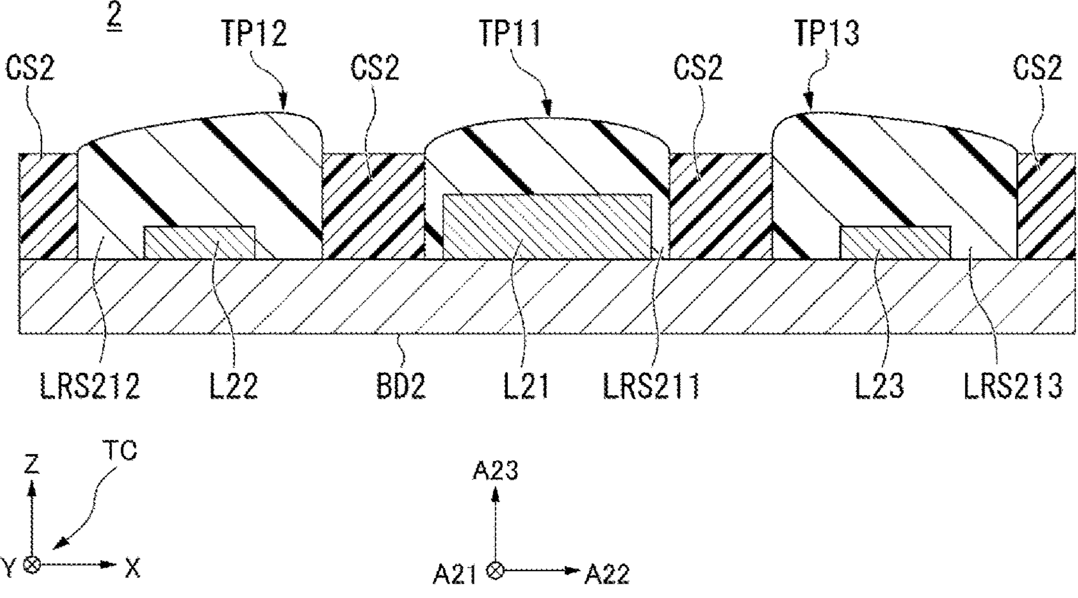
FIG. 22 is a cross-sectional view showing a sixth configuration example of the detection device 2.
Figure 23:
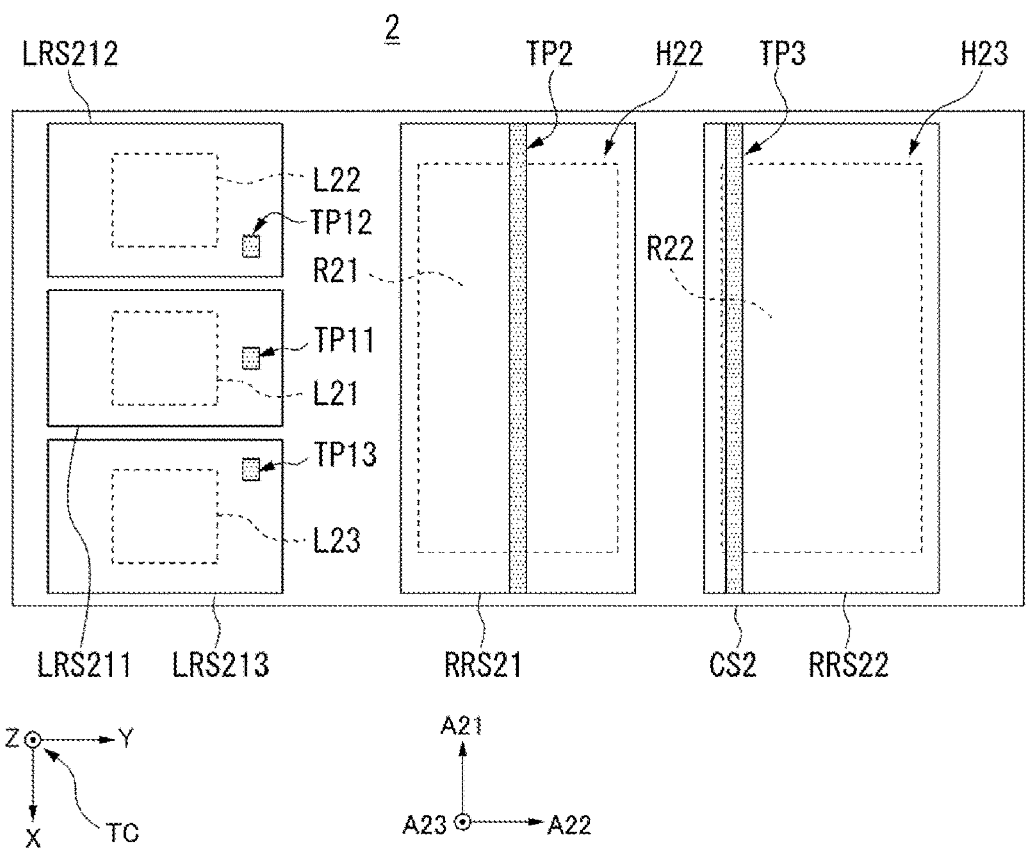
FIG. 23 is a top view of the detection device 2 shown in FIG. 22.

Also, in the detection device 2 shown in FIG. 21, each of the first light emitting side optical member LRS211, the second light emitting side optical member LRS212, and the third light emitting side optical member LRS213 may have a shape having a substantially point-like vertex portion as shown in FIGS. 22 and 23. FIG. 22 is a cross-sectional view showing a sixth configuration example of the detection device 2. However, the cross-sectional view shown in FIG. 22 is a cross-sectional view of the detection device 2 along a virtual plane orthogonal to the first direction A21 so that each of the first light emitting unit L21, the first light receiving unit R21, and the second light receiving unit R22 can be seen when viewed in the first direction A21. FIG. 23 is a top view of the detection device 2 shown in FIG. 22.

In the example shown in FIGS. 22 and 23, a shape of the vertex portion TP11 of the first light emitting side optical member LRS211 is a point-like shape or a substantially point-like shape. In the present disclosure, the substantially point-like shape is a shape that can be regarded as being substantially point-like and is a shape that slightly spreads in a circular shape, a rectangular shape, or the like. In addition, in the example, a position of the vertex portion TP11 at the upper surface of the first light emitting side optical member LRS211 is a position closer to the first light receiving unit R21 than a center of the first light emitting unit L21 when viewed in the third direction A23, and is a position of a center of the first light emitting side optical member LRS211 in the first direction A21 when viewed in the second direction A22. In this case, most of the first light emitted from the first light emitting unit L21 is refracted at the upper surface of the first light emitting side optical member LRS211 so that the traveling direction is shifted toward the second direction A22.

Thus, the detection device 2 can more reliably reduce the amount of the component that becomes stray light in the first light emitted from the first light emitting unit L21. As a result, the detection device 2 can more reliably increase the amount of light received by the first light receiving unit R21 in the first light reflected in the skin of the person.

Also, in the example shown in FIGS. 22 and 23, a shape of the vertex portion TP12 of the second light emitting side optical member LRS212 is a point-like shape or a substantially point-like shape. In addition, in the example, a position of the vertex portion TP12 at the upper surface of the second light emitting side optical member LRS212 is a position closer to the first light receiving unit R21 than a center of the second light emitting unit L22 when viewed in the third direction A23, and is a position closer to the first light emitting unit L21 than a center of the second light emitting side optical member LRS212 in the first direction A21 when viewed in the second direction A22.

In this case, the shape of the upper surface of the first light emitting side optical member LRS211 when viewed in the second direction A22 is different from the shape of the upper surface of the second light emitting side optical member LRS212 when viewed in the second direction A22. In addition, in this case, most of the second light emitted from the second light emitting unit L22 is refracted to be shifted toward a direction close to a fourth direction A24. The fourth direction A24 is a direction parallel to the upper surface of the substrate BD2 and is a direction from the center of the second light emitting unit L22 toward the vertex portion TP12 when viewed in the third direction A23. Thus, the detection device 2 can more reliably reduce the amount of the component that becomes stray light in the second light emitted from the second light emitting unit L22. As a result, the detection device 2 can more reliably increase the amount of light received by the second light receiving unit R22 in the second light reflected in the skin of the person.

Also, in the example shown in FIGS. 22 and 23, a shape of the vertex portion TP13 of the third light emitting side optical member LRS213 is a point-like shape or a substantially point-like shape. In addition, in the example, a position of the vertex portion TP13 at the upper surface of the third light emitting side optical member LRS213 is a position closer to the first light receiving unit R21 than a center of the third light emitting unit L23 when viewed in the third direction A23, and is a position closer to the first light emitting unit L21 than a center of the third light emitting side optical member LRS213 in the first direction A21 when viewed in the second direction A22.

In this case, the shape of the upper surface of the first light emitting side optical member LRS211 when viewed in the second direction A22 is different from the shape of the upper surface of the third light emitting side optical member LRS213 when viewed in the second direction A22. In addition, in this case, most of the third light emitted from the third light emitting unit L23 is refracted to be shifted toward a direction close to a fifth direction A25. The fifth direction A25 is a direction parallel to the upper surface of the substrate BD2 and is a direction from the center of the third light emitting unit L23 toward the vertex portion TP13 when viewed in the third direction A23. Thus, the detection device 2 can more reliably reduce the amount of the component that becomes stray light in the third light emitted from the third light emitting unit L23. As a result, the detection device 2 can more reliably increase the amount of light received by the second light receiving unit R22 in the third light reflected in the skin of the person.

As described above, the detection device 2 is provided are the substrate BD2, the first light emitting unit L21 that emits the first light and is provided at the substrate BD2, the first light receiving unit R21 that receives the first light, is parallel to the substrate BD2 when viewed in the first direction A21 parallel to the substrate BD2, and is provided at the substrate BD2 side by side with the first light emitting unit L21 in the second direction A22 orthogonal to the first direction A21, the first light emitting side optical member LRS21 that transmits the first light and covers the first light emitting unit L21 at the substrate BD2, the first light receiving side optical member RRS21 that transmits the first light and covers the first light receiving unit R21 at the substrate BD2, and the accommodating member CS2 formed with the first opening H21 that is provided at the substrate BD2 and accommodates the first light emitting unit L21 and the first light emitting side optical member LRS21, and the second opening H22 accommodating the first light receiving unit R21 and the first light receiving side optical member RRS21, wherein at least one optical member of the first light emitting side optical member LRS21 and the first light receiving side optical member RRS21 protrudes from the opening formed in the accommodating member CS2 in the third direction A23 intersecting the first direction A21 and the second direction A22.

Thus, the detection device 2 can increase the amount of light received by the first light receiving unit R21 by improving the contact with the skin of the person, and can reduce the size in the third direction A23, as compared with a case in which a lens for condensing the first light emitted from the first light emitting unit L21, a lens for condensing the reflected light of the first light toward the first light receiving unit R21, a member for attaching these lenses to the detection device 1, and the like are provided. That is, the detection device 2 can achieve reduction in size while inhibiting a decrease in the amount of light received by the first light receiving unit R21.

Also, the detection device 2 may be configured to include the coat member URS11 described in the first embodiment. In this case, the coat member URS11 covers at least a part of the upper surface of the detection device 2.

Third Embodiment

A third embodiment will be described below with reference to the drawings.

Overview of Detection Device of Third Embodiment

First, an overview of a detection device according to the third embodiment will be described.

The detection device according to the third embodiment includes a substrate, a first light emitting unit, a first light receiving unit, a first optical member, a second optical member, and an accommodating member. The first light emitting unit emits first light and is provided at the substrate. The first light receiving unit receives the first light and is provided at the substrate side by side with the first light emitting unit in a second direction orthogonal to a first direction among directions parallel to the substrate when viewed in the first direction parallel to the substrate. The first optical member transmits the first light and covers the first light emitting unit at the substrate. The second optical member transmits the first light and covers the first light receiving unit at the substrate. The accommodating member is provided at the substrate and has a first opening in which the first light emitting unit and the first optical member are accommodated and a second opening in which the first light receiving unit and the second optical member are accommodated. Here, the first optical member protrudes from the first opening of the accommodating member in a third direction orthogonal to the first direction and the second direction. Also, the second optical member protrudes from the second opening of the accommodating member in the third direction.

Further, the accommodating member includes a wall portion provided between the first optical member and the second optical member. In addition, a first distance in the second direction from the first light emitting unit to the wall portion is a distance that satisfies a predetermined condition. The condition is that a first value having a negative correlation with an intensity of noise of light received by the first light receiving unit among values that change depending on the first distance is equal to or greater than a predetermined threshold.

Thus, the detection device can increase the amount of light received by the first light receiving unit by improving the contact with the skin of the person, and can reduce the size in the third direction, as compared with a case in which a lens for condensing the first light emitted from the first light emitting unit, a lens for condensing the reflected light of the first light toward the first light receiving unit, a member for attaching these lenses to the detection device 1, and the like are provided. Also, as a result, the detection device can shorten a distance between the first light emitting unit and the wall portion to reduce the intensity of the noise of light received by the first light receiving unit, and can increase an amount of a component directed in the third direction in the first light emitted from the first light emitting unit. That is, the detection device can achieve reduction in size while inhibiting a decrease in the amount of light received by the light receiving unit.

In the following description, the configuration of the detection device according to the third embodiment will be described in detail.

Configuration of Detection Device of Third Embodiment

The third embodiment is a modified example of the second embodiment. For this reason, in the third embodiment, the same constituent parts as in the second embodiment will be denoted by the same reference numerals, and description thereof will be omitted. Also, in the following description, the configuration of the detection device according to the third embodiment will be described using a detection device 3 as an example. In addition, in the third embodiment, for convenience of description, when the detection device 3 is viewed while facing in a certain direction, it will be described as the detection device 2 being viewed in that direction. Further, the configuration of the detection device 2 according to the third embodiment may be combined in any manner with each of the configuration of the detection device 1 according to the first embodiment and the configuration of the detection device 3 according to the second embodiment.

Figure 24:
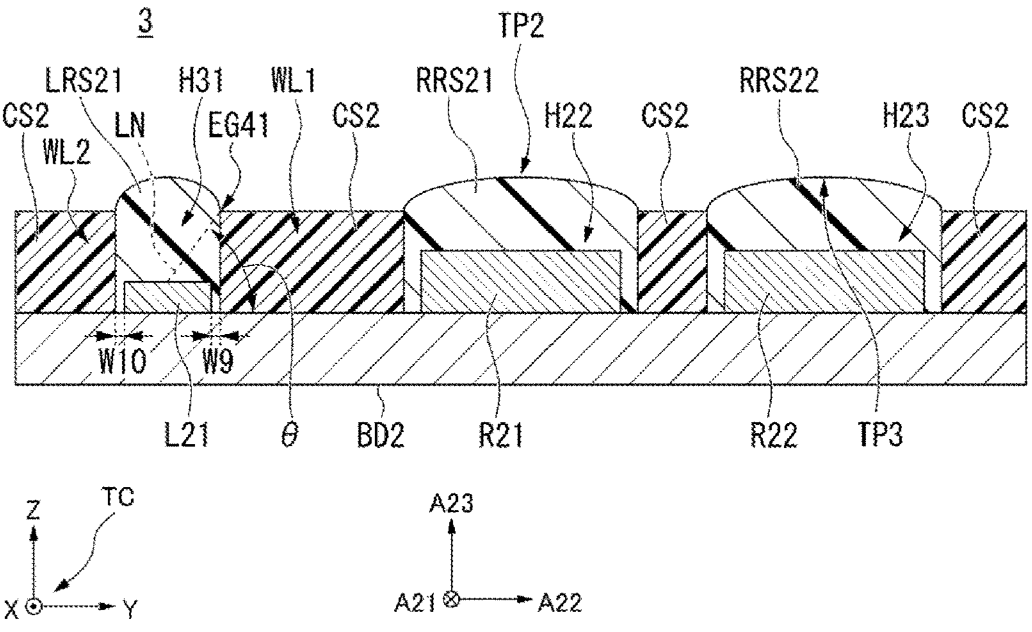
FIG. 24 is a cross-sectional view showing a first configuration example of a detection device 3.

FIG. 24 is a cross-sectional view showing a first configuration example of the detection device 3. However, the cross-sectional view shown in FIG. 24 is a cross-sectional view of the detection device 3 along a virtual plane orthogonal to the first direction A21 so that each of the first light emitting unit L21, the first light receiving unit R21, and the second light receiving unit R22 can be seen when viewed in the first direction A21.

As shown in FIG. 24, the detection device 3 includes, for example, the substrate BD2, the first light emitting unit L21, the second light emitting unit L22, the third light emitting unit L23, the first light receiving unit R21, the second light receiving unit R22, the first light emitting side optical member LRS21, the first light receiving side optical member RRS21, the second light receiving side optical member RRS22, and an accommodating member CS3. That is, the detection device 3 shown in FIG. 24 is a modified example of the detection device 2 shown in FIGS. 12 and 13. Also, the configuration of the detection device 3 shown in FIG. 24 may be applied to each detection device 2 shown in FIGS. 14 to 23. However, in the third embodiment, the third direction A23 is a direction orthogonal to the substrate BD2.

The accommodating member CS3 is provided at the upper surface of the substrate BD2. The accommodating member CS3 is a member that forms the outer shape of the detection device 3 together with the substrate BD2. In the following description, in order to simplify the description, as an example, a case in which the outer shape of the accommodating member CS2 is a rectangular parallelepiped shape as a whole except for various openings formed in the accommodating member CS3, distortions due to manufacturing errors, and the like will be described.

In this case, an upper surface of the accommodating member CS3 is a surface parallel to the substrate BD2. Also, the upper surface of the accommodating member CS3 may be a surface that is not parallel to the substrate BD2. Further, a height of the upper surface of the accommodating member CS3 from the substrate BD2 is determined to be higher than the height of any of the first light emitting unit L21, the second light emitting unit L22, and the third light emitting unit L23 from the substrate BD1.

The accommodating member CS3 is made of, for example, an opaque resin with a high light reflectance, a transparent resin mixed with metal powder, a metal, or the like. In the third embodiment, as an example, a case in which the accommodating member CS3 is made of a white resin will be described.

Here, a first opening H31, the second opening H22, and the third opening H23 are formed in the accommodating member CS3.

The first opening H31 is a hole that penetrates the accommodating member CS3 in the third direction A23 orthogonal to the substrate BD2. The first opening H31 is a hole in which the first light emitting unit L21, the second light emitting unit L22, the third light emitting unit L23, and the first light emitting side optical member LRS21 are accommodated at the upper surface of the substrate BD2. In the example shown in FIG. 24, a shape of a contour of the first opening H31 is a rectangular shape when viewed in the first direction A21. Further, in the example, the shape of the contour of the first opening H31 is a rectangular shape when viewed in the third direction A23. That is, the shape of the first opening H31 is a rectangular parallelepiped shape.

Here, as shown in FIG. 24, the accommodating member CS3 includes a wall portion WL1 provided between the first light emitting side optical member LRS21 and the first light receiving side optical member RRS21. Also, as shown in FIG. 24, when viewed in the first direction A21, the accommodating member CS3 includes a wall portion WL2 on a side opposite to the wall portion WL1 of two wall portions in contact with the first light emitting side optical member LRS21.

As each of a first distance W9 from the first light emitting unit L21 to the wall portion WL1 in the second direction A22 and a second distance W10 from the first light emitting unit L21 to the wall portion WL2 in the second direction A22 is shortened, the detection device 3 can increase an amount of a component directed upward from the first light emitting side optical member LRS21 in the light emitted from each of the first light emitting unit L21, the second light emitting unit L22, and the third light emitting unit L23. This is because, as each of the first distance W9 and the second distance W10 becomes narrower, the light emitted from each of the first light emitting unit L21, the second light emitting unit L22, and the third light emitting unit L23 is more likely to be reflected by each of the wall portion WL1 and the wall portion WL2. Also, the second distance W10 may be the same as the first distance W9, or may be different from the first distance W9. In FIG. 24, as an example, a case in which the second distance W10 is the same as the first distance will be described.

The first distance W9 is determined, for example, as a distance that satisfies a predetermined third condition. The third condition is that, among values that change depending on the first distance W9, a first value that has a negative correlation with the intensity of the noise of light received by the first light receiving unit R21 is equal to or greater than a predetermined threshold. In addition, the intensity of noise is an intensity of stray light received by the first light receiving unit R21. Also, the first value is, for example, an inclination angle θ between a line segment LN and the substrate BD2. Here, when viewed in the first direction A21, the line segment LN is a virtual line segment that couples a position of a center on a surface in the third direction A23 included in the first light emitting unit L21 and an end portion EG41 in the third direction of an inner wall on a side closer to the first light receiving unit R21 among inner walls of the first opening H21.

In this case, as the inclination angle θ serving as the first value increases, the amount of the component directed upward from the first light emitting side optical member LRS21 in the light emitted from each of the first light emitting unit L21, the second light emitting unit L22, and the third light emitting unit L23 increases. This is because increasing the inclination angle θ indicates that each of the first distance W9 and the second distance W10 is shortened. Also, the third condition is an example of the predetermined condition.

Here, the first distance W9 is a distance determined in accordance with the height of the upper surface of each of the first light emitting unit L21, the second light emitting unit L22, and the third light emitting unit L23 from the substrate BD2, the height of the upper surface of the accommodating member CS3 from the substrate BD2, and the first value. For example, the manufacturer of the detection device 3 determines an allowable intensity as an intensity of noise of light received by the first light receiving unit R21, thereby determining the first value having a negative correlation with the intensity of the noise. After that, the manufacturer selects LEDs to be used for the first light emitting unit L21, the second light emitting unit L22, and the third light emitting unit L23.

Thus, the manufacturer can determine the height of the upper surface of each of the first light emitting unit L21, the second light emitting unit L22, and the third light emitting unit L23 from the substrate BD2 and the height of the upper surface of the accommodating member CS3 from the substrate BD2. In addition, the manufacturer can determine each of the first distance W9 and the second distance W10 based on the determined two heights and the determined first value.

As described above, the accommodating member CS3 is provided at the upper surface of the substrate BD2 so that the first distance W9 and the second distance W10 satisfy the above-described third condition. In the example shown in FIG. 24, the predetermined threshold for the inclination angle θ serving as the first value is 45°. For this reason, in the detection device 3 shown in FIG. 24, the first distance W9 and the second distance W10 can be made shorter than the first distance W9 and the second distance W10 in the detection device 2 shown in FIGS. 12 and 13. As a result, the detection device 3 can increase the amount of the component directed upward from the first light emitting side optical member LRS21 in the light emitted from each of the first light emitting unit L21, the second light emitting unit L22, and the third light emitting unit L23. That is, the detection device 3 can shorten the first distance W9 and the second distance W10 to reduce the intensity of the noise of light received by the first light receiving unit R21 and can increase the amount of the component directed in the third direction A23 in the first light emitted from the first light emitting unit L21.

Also, in this case, in the detection device 3, the gradient of the curved surface included in the upper surface of the first light emitting side optical member LRS21 is greater than the gradient of the curved surface included in the upper surface of the first light receiving side optical member RRS21. This is because, although the length of the first light emitting side optical member LRS21 in the second direction A22 is shorter than the length of the first light receiving side optical member RRS21 in the second direction A22, the height of the upper surface of the first light emitting side optical member LRS21 from the substrate BD2 is the same as the height of the upper surface of the first light receiving side optical member RRS21 from the substrate BD2. In addition, the detection device 3 also has the features of the detection device 2 shown in FIGS. 12 and 13. For this reason, the detection device 3 can also reduce the size in the third direction A23. That is, the detection device 3 can achieve reduction in size while inhibiting a decrease in the amount of light received by the first light receiving unit R21 and the second light receiving unit R22.

Also, instead of the inclination angle θ, the first value may be another value that has a negative correlation with the intensity of the noise of light received by the first light receiving unit R21 among values that change depending on the first distance W9. In addition, the inner wall is a surface facing the first light emitting unit L21 among surfaces of the wall portion WL1. Further, the predetermined threshold may be an angle smaller than 45° or may be an angle greater than 45°.

Figure 25:
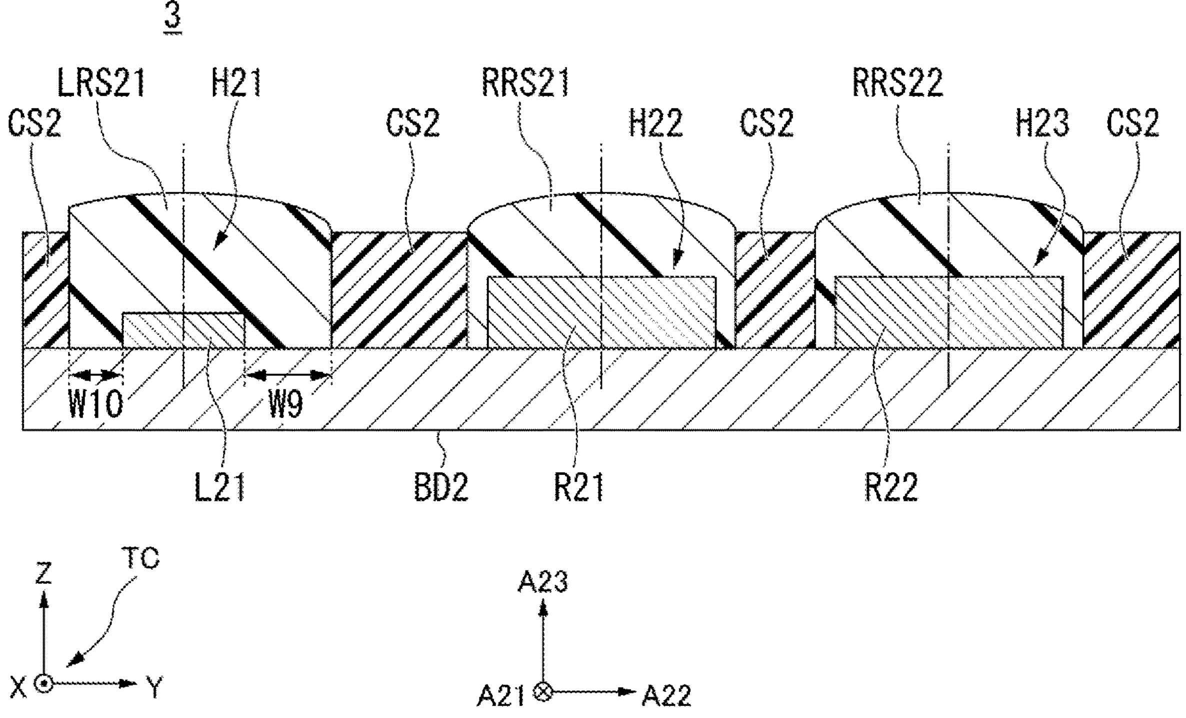
FIG. 25 is a cross-sectional view showing a second configuration example of the detection device 3.

Also, as shown in FIG. 25, the detection device 3 shown in FIG. 24 may have a configuration in which the second distance W10 is shorter than the first distance W9. FIG. 25 is a cross-sectional view showing a second configuration example of the detection device 3. However, the cross-sectional view shown in FIG. 25 is a cross-sectional view of the detection device 3 along a virtual plane orthogonal to the first direction A21 so that each of the first light emitting unit L21, the first light receiving unit R21, and the second light receiving unit R22 can be seen when viewed in the first direction A21.

In the detection device 3 shown in FIG. 25, the second distance W10 is shorter than the first distance W9. In this case, for example, the first distance W9 is determined as a distance that satisfies the third condition as described above. In addition, the second distance W10 may be any distance as long as it is shorter than the first distance W9. In the detection device 3 shown in FIG. 25, when viewed in the first direction A21, traveling directions of the light emitted from each of the first light emitting unit L21, the second light emitting unit L22, and the third light emitting unit L23 after being refracted at the upper surface of the first light emitting side optical member LRS21 are shifted toward directions close to the second direction A22. This is because the light emitted toward the wall portion WL2 of the light emitted from each of the first light emitting unit L21, the second light emitting unit L22, and the third light emitting unit L23 is reflected toward a direction close to the second direction A22.

Thus, as compared with the detection device 2 shown in FIGS. 12 and 13, the detection device 3 shown in FIG. 25 can more reliably reduce the amount of the component that becomes stray light in the light emitted from each of the first light emitting unit L21, the second light emitting unit L22, and the third light emitting unit L23. As a result, the detection device 3 can achieve reduction in size while inhibiting a decrease in the amount of light received by the first light receiving unit R21 and the second light receiving unit R22.

As described above, the detection device 3 includes the substrate BD2, the first light emitting unit L21 that emits the first light and is provided at the substrate BD2, the first light receiving unit R21 that receives the first light and is provided at the substrate BD2 side by side with the first light emitting unit L21 in the second direction A22 orthogonal to the first direction A21 among directions parallel to the substrate BD2 when viewed in the first direction A21 parallel to the substrate BD2, the first light emitting side optical member LRS21 that transmits the first light and covers the first light emitting unit L21 at the substrate BD2, the first light receiving side optical member RRS21 that transmits the first light and covers the first light receiving unit R21 at the substrate BD2, and the accommodating member CS2 that is provided at the substrate BD2 and is formed with the first opening H21 in which the first light emitting unit L21 and the first light emitting side optical member LRS21 are accommodated, and the second opening H22 in which the first light receiving unit R21 and the first light receiving side optical member RRS21 are accommodated, wherein the first light emitting side optical member LRS21 protrudes from the first opening H21 of the accommodating member CS2 in the third direction A23 orthogonal to the first direction A21 and the second direction A22, the first light receiving side optical member RRS21 protrudes from the second opening H22 of the accommodating member CS2 in the third direction A23, the accommodating member CS2 includes the wall portion WL1 provided between the first light emitting side optical member LRS21 and the first light receiving side optical member RRS21, the first distance W9 in the second direction A22 from the first light emitting unit L21 to the wall portion WL1 is a distance that satisfies a predetermined third condition, and the third condition is that, among the values that change depending on the first distance W9, the first value that has a negative correlation with the intensity of the noise of light received by the first light receiving unit R21 is equal to or greater than a predetermined threshold.

Thus, the detection device 3 can shorten the first distance W9 to reduce the intensity of the noise of light received by the first light receiving unit R21, and can increase the amount of the component directed in the third direction A23 of the first light emitted from the first light emitting unit L21. In addition, the detection device 3 also has the features of the detection device 2 shown in FIGS. 12 and 13. For this reason, the detection device 3 can also reduce the size in the third direction A23. That is, the detection device 3 can achieve reduction in size while inhibiting a decrease in the amount of light received by the first light receiving unit R21 and the second light receiving unit R22.

Also, the matters described above may be combined in any manner.

In addition, the positions of the second light emitting unit L12 and the third light emitting unit L13 described above may be exchanged at the upper surface of the substrate BD1.

Also, the positions of the second light emitting unit L22 and the third light emitting unit L23 described above may be exchanged at the upper surface of the substrate BD2.

Further, the upper surfaces of some or all of the first light emitting side optical member LRS21, the first light emitting side optical member LRS211, the second light emitting side optical member LRS212, the third light emitting side optical member LRS213, the first light receiving side optical member RRS21, and the second light receiving side optical member RRS22 described above may not include a curved surface.

Also, the first light receiving side optical member RRS21 described above may be configured integrally with the second light receiving side optical member RRS22. In this case, the second opening H22 is coupled to the third opening H23.

APPENDIX 1

[1]

A detection device including a substrate, a first light emitting unit that emits first light and is provided at the substrate, a first light receiving unit that receives the first light, is parallel to the substrate when viewed in a first direction parallel to the substrate, and is provided at the substrate side by side with the first light emitting unit in a second direction orthogonal to the first direction, a first optical member that transmits the first light and covers the first light emitting unit at the substrate, a second optical member that transmits the first light and covers the first light receiving unit at the substrate, and an accommodating member that is provided at the substrate and formed with an opening accommodating the first light emitting unit, the first optical member, the first light receiving unit, and the second optical member, wherein at least a part of a space between the first optical member and the second optical member in the second direction is a gap.

[2]

The detection device according to [1] further including a coat member that is provided in at least a part of a first surface opposite to a surface in contact with the substrate among surfaces included in the second optical member, and makes a transmittance of the first light incident at an angle smaller than a first angle on the first surface higher than a transmittance of the first light incident at an angle equal to or greater than the first angle on the first surface.

[3]

The detection device according to [1] or [2], wherein a length of the gap in the second direction increases as a distance from the substrate increases in a third direction orthogonal to both the first direction and the second direction.

[4]

The detection device according to any one of [1] to [3] further including a second light emitting unit that emits second light in a wavelength band different from a wavelength band of the first light and is provided at the substrate side by side with the first light emitting unit in the first direction, a second light receiving unit that receives the second light and is provided at the substrate side by side with the first light receiving unit in the second direction, a third optical member that transmits the second light and covers the second light emitting unit at the substrate, and a fourth optical member that transmits the second light and covers the second light receiving unit at the substrate, wherein the opening accommodates the second light emitting unit, the third optical member, the second light receiving unit, and the fourth optical member together with the first light emitting unit, the first optical member, the first light receiving unit, and the second optical member, a space between the second optical member and the fourth optical member is a gap, and a space between the first optical member and the third optical member is a gap.

[5]

The detection device according to [4], wherein a length of the gap between the first optical member and the third optical member in the first direction is longer than a length of a gap between the third optical member and the fourth optical member in the second direction.

[6]

The detection device according to any one of [1] to [5] further including a fifth optical member that covers the first light emitting unit at the substrate between the first optical member and the first light emitting unit in a third direction orthogonal to both the first direction and the second direction, wherein a refractive index of the fifth optical member is greater than a refractive index of the first optical member, and the first optical member covers the first light emitting unit by covering the fifth optical member at the substrate.

[7]

The detection device according to [6], wherein a surface on a side opposite to the substrate among surfaces included in the fifth optical member includes a curved surface having a positive gradient in the third direction.

[8]

The detection device according to any one of [1] to [7], wherein when viewed in the second direction, a part of the gap between the first optical member and the second optical member overlaps each of the first light emitting unit and the first light receiving unit.

[9]

The detection device according to any one of [1] to [8], wherein the substrate has a recessed portion at a position overlapping the gap.

APPENDIX 2

[1]

A detection device including a substrate, a first light emitting unit that emits first light and is provided at the substrate, a first light receiving unit that receives the first light, is parallel to the substrate when viewed in a first direction parallel to the substrate, and is provided at the substrate side by side with the first light emitting unit in a second direction orthogonal to the first direction, a first optical member that transmits the first light and covers the first light emitting unit at the substrate, a second optical member that transmits the first light and covers the first light receiving unit at the substrate, and an accommodating member that is provided at the substrate and formed with a first opening accommodating the first light emitting unit and the first optical member and a second opening accommodating the first light receiving unit and the second optical member, wherein at least one optical member of the first optical member and the second optical member protrudes from an opening formed in the accommodating member in a third direction intersecting the substrate.

[2]

The detection device according to [1], wherein a surface in the third direction among surfaces included in the accommodating member is orthogonal to the third direction, and a surface in the third direction among surfaces included in the at least one optical member includes a curved surface having a positive gradient in the third direction.

[3]

The detection device according to [1] or [2], wherein a surface in the third direction among surfaces included in the accommodating member is orthogonal to the third direction, the first optical member protrudes from the first opening of the accommodating member in the third direction, the second optical member protrudes from the second opening of the accommodating member in the third direction, a surface in the third direction among surfaces included in the first optical member includes a curved surface having a positive gradient in the third direction, and a surface in the third direction among surfaces of the second optical member includes a curved surface having a positive gradient in the third direction.

[4]

The detection device according to [3], wherein, when viewed in the first direction, a shape of the surface in the third direction among the surfaces included in the first optical member and a shape of the surface in the third direction among the surfaces included in the second optical member are different from each other.

[5]

The detection device according to any one of [1] to [4], wherein a surface in the third direction among surfaces included in the accommodating member is orthogonal to the third direction, a surface in the third direction among surfaces of the first optical member has a portion having the highest height from the accommodating member in the third direction as a first vertex portion, and when viewed in the first direction, a first virtual line segment that passes through a center of the surface in the third direction among the surfaces included in the first light emitting unit and extends in the third direction overlaps the first vertex portion.

[6]

The detection device according to [5], wherein, when viewed in the first direction, the first vertex portion is closer to the first light receiving unit than the first line segment in the second direction.

[7]

The detection device according to any one of [1] to [6], wherein a surface in the third direction among surfaces included in the accommodating member is orthogonal to the third direction, a surface in the third direction among surfaces included in the second optical member has a portion having the highest height from the accommodating member in the third direction as a second vertex portion, and when viewed in the first direction, a second virtual line segment that passes through a center of a surface in the third direction among surfaces included in the first light receiving unit and extends in the third direction does not overlap the second vertex portion.

[8]

The detection device according to [7], wherein, when viewed in the first direction, the second vertex portion is closer to the first light emitting unit than the second line segment in the second direction.

[9]

The detection device according to any one of [1] to [8], wherein a surface in the third direction among surfaces included in the accommodating member is orthogonal to the third direction, and a height in the third direction from the accommodating member to a surface in the third direction among surfaces included in the at least one optical member is a height equal to or higher than a first height that satisfies a predetermined first condition and equal to or lower than a second height that satisfies a predetermined second condition.

[10]

The detection device according to [9], wherein the first condition is a height at which contact with human skin is not reduced.

[11]

The detection device according to [10], wherein the first height is 0.2 mm.

[12]

The detection device according to any one of [9] to [11], wherein the second condition is a height at which capillary vessels in human dermis do not collapse.

[13]

The detection device according to [12], wherein the second height is 1.2 mm.

[14]

The detection device according to any one of [1] to [13], wherein a surface in the third direction among surfaces included in the accommodating member is orthogonal to the third direction, a contour of a cross-section of the first optical member along a virtual plane including the surface in the third direction among the surfaces included in the accommodating member coincides with a shape of an inner edge of the first opening when viewed in the third direction, and a contour of a cross-section of the second optical member along a virtual plane including the surface in the third direction among the surfaces included in the accommodating member coincides with a shape of an inner edge of the second opening when viewed in the third direction.

[15]

The detection device according to [14], wherein the third direction is orthogonal to the substrate, a shape of a region that overlaps the first opening among regions included in the first optical member is a rectangular shape when viewed in the first direction, and a shape of a region that overlaps the second opening among regions included in the second optical member is a rectangular shape when viewed in the first direction.

[16]

The detection device according to any one of [1] to further including a second light emitting unit that emits second light having a wavelength band different from a wavelength band of the first light and is provided at the substrate side by side with the first light emitting unit in the first direction, a second light receiving unit that receives the second light and is provided at the substrate side by side with the first light receiving unit in the second direction, a third optical member that transmits the second light and covers the second light emitting unit at the substrate, and a fourth optical member that transmits the second light and covers the second light receiving unit at the substrate, wherein the accommodating member is formed with a fourth opening in which the second light receiving unit and the fourth optical member are accommodated, the first opening accommodates the second light emitting unit and the third optical member together with the first optical member, and the first optical member is configured integrally with the third optical member.

[17]

The detection device according to [16], wherein, when viewed in the first direction, a shape of a surface in the third direction among surfaces included in the second optical member and a shape of a surface in the third direction among surfaces included in the fourth optical member are different from each other.

[18]

The detection device according to [17], wherein a surface in the third direction among surfaces included in the accommodating member is orthogonal to the third direction, the surface in the third direction among the surfaces included in the second optical member has a portion having the highest height from the accommodating member in the third direction as a second vertex portion, the surface in the third direction among the surfaces included in the fourth optical member has a portion having the highest height from the accommodating member in the third direction as a fourth vertex portion, when viewed in the first direction, a distance in the second direction between the second vertex portion and a second virtual line segment that passes through a center of a surface in the third direction among surfaces included in the first light receiving unit and extends in the third direction is shorter than a distance in the second direction between the fourth vertex portion and a fourth virtual line segment that passes through a center of a surface in the third direction among surfaces included in the second light receiving unit and extends in the third direction, when viewed in the first direction, the second vertex portion is closer to the first light emitting unit than the second line segment in the second direction, and when viewed in the first direction, the fourth vertex portion is closer to the first light emitting unit than the fourth line segment in the second direction.

[19]

The detection device according to any one of to [18], wherein a distance between the first optical member and the second optical member in the second direction is longer than a distance between the second optical member and the fourth optical member in the second direction.

[20]

The detection device according to any one of to [18], wherein a distance between the first optical member and the second optical member in the second direction is shorter than a distance between the second optical member and the fourth optical member in the second direction.

[21]

The detection device according to any one of [1] to [15] further including a second light emitting unit that emits second light having a wavelength band different from a wavelength band of the first light and is provided at the substrate side by side with the first light emitting unit in the first direction, a second light receiving unit that receives the second light and is provided at the substrate side by side with the first light receiving unit in the second direction, a third optical member that transmits the second light and covers the second light emitting unit at the substrate, and a fourth optical member that transmits the second light and covers the second light receiving unit at the substrate, wherein the accommodating member is formed with a third opening in which the second light emitting unit and the third optical member are accommodated and a fourth opening in which the second light receiving unit and the fourth optical member are accommodated.

[22]

The detection device according to [21], wherein a surface in the third direction among surfaces included in the accommodating member is orthogonal to the third direction, and when viewed in the second direction, a shape of a surface in the third direction among surfaces included in the first optical member and a shape of a surface in the third direction among surfaces included in the third optical member are different from each other.

APPENDIX 3

[1]

A detection device including a substrate, a first light emitting unit that emits first light and is provided at the substrate, a first light receiving unit that receives the first light and is provided, when viewed in a first direction parallel to the substrate, at the substrate side by side with the first light emitting unit in a second direction orthogonal to the first direction among directions parallel to the substrate, a first optical member that transmits the first light and covers the first light emitting unit at the substrate, a second optical member that transmits the first light and covers the first light receiving unit at the substrate, and an accommodating member that is provided at the substrate and formed with a first opening accommodating the first light emitting unit and the first optical member and a second opening accommodating the first light receiving unit and the second optical member, wherein the first optical member protrudes from the first opening of the accommodating member in a third direction orthogonal to the first direction and the second direction, the second optical member protrudes from the second opening of the accommodating member in the third direction, the accommodating member includes a wall portion provided between the first optical member and the second optical member, a first distance in the second direction from the first light emitting unit to the wall portion is a distance that satisfies a predetermined condition, and the condition is that, among values that change depending on the first distance, a first value that has a negative correlation with an intensity of noise of light received by the first light receiving unit is equal to or greater than a predetermined threshold.

[2]

The detection device according to [1], wherein the intensity of the noise is an intensity of stray light received by the first light receiving unit, a surface in the third direction among surfaces included in the accommodating member is parallel to the substrate, and the first value is, when viewed in the first direction, an inclination angle between the substrate and a line segment coupling a position of a center of a surface in the third direction included in the first light emitting unit and an end portion in the third direction of an inner wall closer to the first light receiving unit among inner walls of the first opening.

[3]

The detection device according to [2], wherein the first distance is a value determined in accordance with a length of the first light emitting unit in the third direction, a length of the accommodating member in the third direction, and the first value.

[4]

The detection device according to any one of [1] to [3], wherein the accommodating member is provided at the substrate such that the first distance is a distance satisfying the condition.

[5]

The detection device according to any one of [1] to [4], wherein a surface in the third direction among surfaces included in the accommodating member is parallel to the substrate, and a surface in the third direction among surfaces included in the first optical member includes a curved surface having a positive gradient in the third direction.

[6]

The detection device according to [5], wherein a surface in the third direction among surfaces included in the second optical member includes a curved surface having a positive gradient in the third direction, and a curvature of a curved surface included in the surface in the third direction among surfaces included in the first optical member is smaller than a curvature of the curved surface included in the surface in the third direction among the surfaces included in the second optical member.

[7]

The detection device according to any one of [1] to [6], wherein a surface in the third direction among surfaces included in the accommodating member is parallel to the substrate, and a height in the third direction to a surface in the third direction among surfaces included in the first optical member from the accommodating member is equal to or higher than a first height satisfying a predetermined first condition and equal to or lower than a second height satisfying a predetermined second condition.

[8]

The detection device according to [7], wherein the first condition is a height at which capillary vessels in human dermis do not collapse.

[9]

The detection device according to [8], wherein the first height is 0.2 mm.

[10]

The detection device according to any one of [7] to [9], wherein the second condition is a height at which capillary vessels in human dermis do not collapse.

[11]

The detection device according to [10], wherein the second height is 1.2 mm.

[12]

The detection device according to any one of [1] to [11], wherein a surface in the third direction among surfaces included in the accommodating member is parallel to the substrate, a shape of a region overlapping the first opening among regions included in the first optical member is a rectangular shape when viewed in the second direction, and a shape of a region overlapping the second opening among regions included in the second optical member is a rectangular shape when viewed in the second direction.

[13]

The detection device according to any one of [1] to [12] further including a second light emitting unit that emits second light having a wavelength band different from a wavelength band of the first light and is provided at the substrate side by side with the first light emitting unit in the first direction, a second light receiving unit that receives the second light and is provided at the substrate side by side with the first light receiving unit in the second direction, a third optical member that transmits the second light and covers the second light emitting unit at the substrate, and a fourth optical member that transmits the second light and covers the second light receiving unit at the substrate, wherein the accommodating member is formed with a fourth opening in which the second light receiving unit and the fourth optical member are accommodated, the first opening accommodates the second light emitting unit and the third optical member together with the first optical member, and the first optical member is configured integrally with the third optical member.

[14]

The detection device according to any one of [1] to [13], wherein a width of the first opening in the second direction is the same as a width of the second opening in the second direction.

[15]

The detection device according to any one of [1] to [13], wherein a width of the first opening in the second direction is shorter than a width of the second opening in the second direction.

[16]

The detection device according to any one of to [15], wherein a distance between the first optical member and the second optical member in the second direction is longer than a distance between the second optical member and the fourth optical member in the second direction.

[17]

The detection device according to any one of to [15], wherein a distance between the first optical member and the second optical member in the second direction is shorter than a distance between the second optical member and the fourth optical member in the second direction.

[18]

The detection device according to any one of to [17], wherein a shape of a surface in the third direction among surfaces included in the second optical member and a shape of a surface in the third direction among surfaces included in the fourth optical member are different from each other when viewed in the first direction.

[19]

The detection device according to any one of [1] to further including a second light emitting unit that emits second light having a wavelength band different from a wavelength band of the first light and is provided at the substrate side by side with the first light emitting unit in the first direction, a second light receiving unit that receives the second light and is provided at the substrate side by side with the first light receiving unit in the second direction, a third optical member that transmits the second light and covers the second light emitting unit at the substrate, and a fourth optical member that transmits the second light and covers the second light receiving unit at the substrate, wherein the accommodating member is formed with a third opening in which the second light emitting unit and the third optical member are accommodated, and a fourth opening in which the second light receiving unit and the fourth optical member are accommodated.

[20]

The detection device according to [19], wherein when viewed in the second direction, a shape of a surface in the third direction among surfaces included in the first optical member is the same as a shape of a surface in the third direction among surfaces included in the third optical member.

[21]

The detection device according to [19], wherein when viewed in the second direction, a shape of a surface in the third direction among surfaces included in the first optical member is different from a shape of a surface in the third direction among surfaces included in the third optical member.

These are detailed description of the embodiment according to the present disclosure with reference to the drawings. However, specific configurations are not limited to this embodiment, and may be modified, replaced, deleted, or the like, provided that these do not depart from the main point of the present disclosure.

What is claimed is:

1. A detection device comprising:

a substrate;

a first light emitting unit that emits first light and is provided at the substrate;

a first light receiving unit that receives the first light, is parallel to the substrate when viewed in a first direction parallel to the substrate, and is provided at the substrate side by side with the first light emitting unit in a second direction orthogonal to the first direction;

a first transparent resin that transmits the first light and covers the first light emitting unit at the substrate;

a second transparent resin that transmits the first light and covers the first light receiving unit at the substrate; and an accommodating member that is provided at the substrate and formed with a first opening accommodating the first light emitting unit and the first transparent resin and a second opening accommodating the first light receiving unit and the second transparent resin, wherein at least one of the first transparent resin and the second transparent resin protrudes from an opening formed in the accommodating member in a third direction intersecting the first direction and the second direction, the third direction being directed from the substrate toward the first light emitting unit, the first transparent resin includes a curved surface having a positive gradient in the third direction, the curved surface has a first vertex portion, a height of the first vertex portion from the accommodating member in the third direction being higher than a height of other portions of the curved surface, and when viewed in the first direction, a distance between the first vertex portion and the first light receiving unit is shorter than a distance between a center of the first transparent resin and the first light receiving unit.

2. The detection device according to claim 1, wherein a surface in the third direction among surfaces included in the accommodating member is orthogonal to the third direction, and a surface in the third direction among surfaces included in the second transparent resin includes a curved surface having a positive gradient in the third direction.

3. The detection device according to claim 1, wherein a surface in the third direction among surfaces included in the accommodating member is orthogonal to the third direction, the first transparent resin protrudes from the first opening of the accommodating member in the third direction, the second transparent resin protrudes from the second opening of the accommodating member in the third direction, and a surface in the third direction among surfaces included in the second transparent resin includes a curved surface having a positive gradient in the third direction.

4. The detection device according to claim 3, wherein, when viewed in the first direction, a shape of the surface in the third direction among the surfaces included in the first transparent resin and a shape of the surface in the third direction among the surfaces included in the second transparent resin are different from each other.

5. The detection device according to claim 1, wherein a surface in the third direction among surfaces included in the accommodating member is orthogonal to the third direction, a surface in the third direction among surfaces included in the second transparent resin has a portion having the highest height from the accommodating member in the third direction as a second vertex portion, and, when viewed in the first direction, the second vertex portion is closer to the first light emitting unit than a second virtual line segment that passes through a center of a surface in the third direction among surfaces included in the first light receiving unit and extends in the third direction.

6. The detection device according to claim 1, wherein a surface in the third direction among surfaces included in the accommodating member is orthogonal to the third direction, and a height in the third direction from the accommodating member to a surface in the third direction among surfaces included in at least one of the first transparent resin and the second transparent resin is a height equal to or higher than a first height that satisfies a predetermined first condition and equal to or lower than a second height that satisfies a predetermined second condition.

7. The detection device according to claim 6, wherein the first condition is a height at which contact with human skin is not reduced.

8. The detection device according to claim 7, wherein the first height is 0.2 mm.

9. The detection device according to claim 6, wherein the second condition is a height at which capillary vessels in human dermis do not collapse.

10. The detection device according to claim 9, wherein the second height is 1.2 mm.

11. The detection device according to claim 1, wherein a surface in the third direction among surfaces included in the accommodating member is orthogonal to the third direction, a contour of a cross-section of the first transparent resin along a virtual plane including the surface in the third direction among the surfaces included in the accommodating member coincides with a shape of an inner edge of the first opening when viewed in the third direction, and a contour of a cross-section of the second transparent resin along a virtual plane including the surface in the third direction among the surfaces included in the accommodating member coincides with a shape of an inner edge of the second opening when viewed in the third direction.

12. The detection device according to claim 11, wherein the third direction is orthogonal to the substrate, when viewed in the first direction, a shape of a region that overlaps the first opening among regions included in the first transparent resin is a rectangular shape, and, when viewed in the first direction, a shape of a region that overlaps the second opening among regions included in the second transparent resin is a rectangular shape.

13. The detection device according to claim 1 further comprising:

a second light emitting unit that emits second light having a wavelength band different from a wavelength band of the first light and is provided at the substrate side by side with the first light emitting unit in the first direction;

a second light receiving unit that receives the second light and is provided at the substrate side by side with the first light receiving unit in the second direction;

a third transparent resin that transmits the second light and covers the second light emitting unit at the substrate; and a fourth transparent resin that transmits the second light and covers the second light receiving unit at the substrate, wherein the accommodating member is formed with a fourth opening in which the second light receiving unit and the fourth transparent resin are accommodated, the first opening accommodates the second light emitting unit and the third transparent resin together with the first transparent resin, and the first transparent resin is configured integrally with the third transparent resin.

14. The detection device according to claim 13, wherein, when viewed in the first direction, a shape of a surface in the third direction among surfaces included in the second transparent resin and a shape of a surface in the third direction among surfaces included in the fourth transparent resin are different from each other.

15. The detection device according to claim 14, wherein an upper surface in the third direction among the surfaces included in the second transparent resin has a portion having the highest height from the accommodating member in the third direction, as a second vertex portion, an upper surface in the third direction among the surfaces included in the fourth transparent resin has a portion having the highest height from the accommodating member in the third direction, as a fourth vertex portion, when viewed in the first direction, a distance in the second direction between the second vertex portion and a second virtual line segment is shorter than a distance in the second direction between the fourth vertex portion and a fourth virtual line segment, wherein the second virtual line segment passes through a center of a surface in the third direction among surfaces included in the first light receiving unit and extends in the third direction, and the fourth virtual line segment passes through a center of a surface in the third direction among surfaces included in the second light receiving unit and extends in the third direction, when viewed in the first direction, the second vertex portion is closer to the first light emitting unit than the second virtual line segment in the second direction, and, when viewed in the first direction, the fourth vertex portion is closer to the first light emitting unit than the fourth virtual line segment in the second direction.

16. The detection device according to claim 13, wherein a distance between the first transparent resin and the second transparent resin in the second direction is longer than a distance between the second transparent resin and the fourth transparent resin in the second direction.

17. The detection device according to claim 13, wherein a distance between the first transparent resin and the second transparent resin in the second direction is shorter than a distance between the second transparent resin and the fourth transparent resin in the second direction.

18. The detection device according to claim 1 further comprising:

a second light emitting unit that emits second light having a wavelength band different from a wavelength band of the first light and is provided at the substrate side by side with the first light emitting unit in the first direction;

a second light receiving unit that receives the second light and is provided at the substrate side by side with the first light receiving unit in the second direction;

a third transparent resin that transmits the second light and covers the second light emitting unit at the substrate; and a fourth transparent resin that transmits the second light and covers the second light receiving unit at the substrate, wherein the accommodating member is formed with a third opening in which the second light emitting unit and the third transparent resin are accommodated and a fourth opening in which the second light receiving unit and the fourth transparent resin are accommodated.

19. The detection device according to claim 18, wherein a surface in the third direction among surfaces included in the accommodating member is orthogonal to the third direction, and, when viewed in the second direction, a shape of a surface in the third direction among surfaces included in the first transparent resin and a shape of a surface in the third direction among surfaces included in the third transparent resin are different from each other.

* * * * *